US006388168B1

(12) United States Patent
Maliga et al.

(10) Patent No.: US 6,388,168 B1
(45) Date of Patent: May 14, 2002

(54) DNA CONSTRUCTS AND METHODS FOR STABLY TRANSFORMING PLASTIDS OF MULTICELLULAR PLANTS AND EXPRESSING RECOMBINANT PROTEINS THEREIN

(75) Inventors: Pal Maliga; Zora Svab Maliga, both of East Brunswick, NJ (US); Jeffrey M. Staub, Wildwood, MO (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 09/193,853

(22) Filed: Nov. 18, 1998

Related U.S. Application Data

(62) Division of application No. 08/189,256, filed on Jan. 31, 1994, now Pat. No. 5,877,402, which is a continuation-in-part of application No. 08/111,398, filed on Aug. 25, 1993, now Pat. No. 5,451,513, which is a continuation of application No. 07/518,763, filed on May 1, 1990, now abandoned.

(51) Int. Cl.$^7$ .......................... C12N 15/29; C12N 15/31; C12N 15/33; C12N 15/82
(52) U.S. Cl. ....................... 800/278; 800/287; 800/288; 536/23.6; 536/23.7; 536/23.72; 536/24.1; 435/69.1; 435/320.1; 435/468
(58) Field of Search ................................. 800/278, 287, 800/288; 536/23.6, 23.7, 23.72, 24.1; 435/468, 320.1, 69.1

(56) References Cited

FOREIGN PATENT DOCUMENTS

| EP | 0251654 | | 1/1988 |
|---|---|---|---|
| EP | 251654 | * | 1/1998 |

OTHER PUBLICATIONS

Sun et al. Mol. Cell. Biol. 9(12): 5650–5659, Dec. 1989.*
Blowers et al. Plant Cell No. 11 2: 1059–1070, Nov. 1990.*
Daniell et al. Plant Cell Reports 9(11): 615–619, 1991.*
Staub et al. EMBO J 12(2): 601–606, 1993.*
Ye et al. Plant Mol. Biol. 15: 809–819, 1990.*
Aldrich et al., Curr. Genet., 14: 137–46, (1988).
Barkan, EMBO J., 7: 2637–44, (1988).
Beck et al., Gene, 19: 327–336, (1982).
Bendich, BioEssays, 6: 279–82, (1987).
Benfey et al., EMBO J., 8: 2195–2202, (1989).
Berg et al., PNAS, 72: 3628–32, (1975).
Berry et al., Plant Cell, 2: 795–803, (1990).
Blowers et al., Plant Cell, 1: 123–132, (1989).
Bonham–Smith and Bourque, Nucleic Acid Res., 17: 2057–78, (1989).
Boynton et al., Science, 240: 1534–1537, (1988).
Cannon et al., Plant Cell Reports, 4: 41–45, (1985).
Carey et al., J. Mol. Biol., 209: 423–432, (1989).
Carrer et al., Mol. Gen. Genet., 241: 49–56, (1993).

Carrer et al., Plant Mol. Biol., 17: 301–303, (1991).
Carillo and Bogorad Nucl. Acids res., 11: 5603–20, (1988).
Chinault et al., Plasmid, 15: 119–131, (1986).
Christopher et al., Plant Cell, 4: 785–89, (1992).
Cornelissen and Vandewiele, Nucleic Acid Res., 17: 19–28, (1989).
Coruzzi et al., J. Biol. Chem., 258: 1399–1402, (1983).
Cseplo et al., Mol. Gen. Genet., 200: 508–510, (1985).
Cseplo et al., Mol. Gen. Genet., 214: 295–99, (1988).
Cseplo and Maliga, Mol. Gen. Genet., 196: 407–412, (1984).
Czernylowski e al., DNA, 5: 101–103, (1986).
Daniell et al., Proc. Natl. Acad. Sci., 84: 6349–6353, (1987).
De Block et al., EMBO vol. 4, No. 6: 1367–1372, (1985).
Deng and Gruissem, Cell, 49: 379–387, (1988).
Deng and Gruissem, EMBO J, 7: 3301–08, (1988).
Durbin and Uchytil, Biochem. Genet., 15: 1143–45, (1977).
Erickson et al., Science, 288: 204–07, (1985).
Etzold et al., FEBS Lett., 219: 343–46, (1987).
Fejes et al., Theor. App. Genet., 79: 28–32, (1990).
Fromm et al., Nature, 319: 791–793, (1986).
Fromm et al., Plant Mol. Biol., 12: 499–505, (1989).
Fromm et al., EMBO, 6, No. 11: 3233–3237, (1987).
Gatenbay et al., EMBO J., 7: 1307–14, (1988).
Goldschmidt–Clermont, Nuc. Acids Res., 19: 4083–4089, (1991).

(List continued on next page.)

Primary Examiner—David T. Fox
(74) Attorney, Agent, or Firm—Dann, Dorfman, Herrell and Skillman

(57) ABSTRACT

DNA constructs are provided for stable transformation of plastids of multicellular plants and expression of foreign proteins in plastids. The DNA constructs comprise a transforming DNA which is targeted to a pre-determined location on the plastid genome and inserted into the plastid genome by homologous recombination with targeting segments comprising DNA sequences homologous to the pre-determined region of the plastid genome. The transforming DNA contains a non-lethal selectable marker gene which confers a selectable phenotype on cells having plastids in which substantially all of the genomes therein contain the transforming DNA (i.e., homoplasmic cells or tissues). The transforming DNA further comprises at least one insertion site 4 for an additional DNA segment, such as a gene encoding a protein for improving a characteristic of the transformed plant. The non-lethal selectable marker gene is preferably provided as a chimeric gene by assembly from an expression cassette comprising 5' and 3' regulatory segments, preferably derived from plastid genes. A coding segment encoding the non-lethal selectable marker is inserted between the 5' and 3' regulatory segments to form the chimeric gene. The non-lethal selectable marker coding segment preferred in the present invention is the coding region of aadA from bacteria, which encodes aminoglycoside 3"-adenylyltransferase to confer spectinomycin and streptomycin resistance.

19 Claims, 47 Drawing Sheets

OTHER PUBLICATIONS

Greenberg et al., EMBO J., 6: 2865–69, (1987).
Gruissem, Cell, 56: 161–70, (1989).
Gruissem & Tonkyn, Critical Review in Plant Sciences, 12: 19–55, (1993).
Harris et al., Genetics, 123: 281–92, (1989).
Horsch et al., Science, 227: 1229–1231, (1985).
Jefferson et al., EMBO J., 6: 3901–3907, (1987).
Kanevski et al., Plant J., 2: 457–63, (1992).
Kanno et al., Theor. Appl. Genet., 86: 579–84, (1993).
Kindle et al., J. Cell. Biol., 108: 2589–2601, (1989).
Klein et al., Bio/Technology, 6: 559–63, (1988).
Klein et al., J. Cell Biol., 106: 289–301, (1988).
Klein and Mullet, J. Biol. Chem., 261: 11138–45, (1986).
Klein et al., PNAS, 85: 8502–05, (1988).
Koncz et al., PNAS, 86: 8467–71, (1989).
Krens et al., Nature, 296: 72–74, (1982).
Kunkel, PNAS, 88: 488–92, (1985).
Maliga et al., Nature (London) New Biol., 244: 29–30, (1973).
Maliga et al., Nature, 255: 401–02, (1973).
Maliga et al., Mol. Gen. Genet., 214: 456–59, (1973).
Maliga, TIB Tech, 11: 101–07, (1993).
Medgyesy et al., PNAS, 82: 6990–64, (1985).
Melancon et al., Nucl. Acids Res., 16: 9631–39, (1988).
Montandon et al., EMBO J., 5: 3705–08, (1986).
Mullet, Plant Physiol., 103, 309–13, (1993).
Negrutiu et al., Plant Mol. Biol., 8: 363–73, (1987).
Palmer, Ann. rev. Genet., 19: 325–54, (1985).
Palmer et al., TIG, 6: 115–120, (1990).
Pay et al., Nucl. Acid Res., 16: 8176, (1988).
Piorier et al., Science, 256: 520–523, (1992).
Ramesh and Osborne, Anal. Biochem., 193: 316–318, (1991).
Rapp et al., J. Biol. Chem., 267: 21404–11, (1992).
Rochaix, Ann. Rev. Cell Biol., 8: 128, (1992).
Sakamoto et al., PNAS, 90: 497–501, (1993).
Sato et al., Mol. Gen. Genet., 214: 358–60, (1988).
Schmidt and Mishkind, PNAS, 80: 2632–36, (1983).
Shinozaki et al., Gene, 24: 147–55, (1983).
Shinozaki and Sugiura, Gene, 20: 91–102, (1982).
Shinozaki et al., EMBO, 5 no. 9: 2043–49, (1986).
Sigmund et al., Nucl. Acids Res., 11: 4653–63, (1984).
Stern & Gruissem, Cell, 51: 1145–1157, (1987).
Staub et al., EMBO, 12, No. 2: 601–605, (1993).
Sugita and Sugiura, Molec. Gen. Genet., 195: 308–313, (1984).
Sugiura Plant Mol. Biol., 19: 149–168, (1992).
Sun et al., Mol. Cell Bio., 9: 5650–59, (1989).
Svab et al., Plant Mol. Biol., 14: 197–205, (1990).
Svab et al., Proc. Natl. Acad. Sci., 87: 8526–8530, (1990).
Svab and Maliga, Mol. Gen. Genet., 228: 316–19, (1991).
Svab et al., Mol. Gen. Genetl., 228: 316–19, (1991).
Svab et al., Proc. Natl. Acad. Sci., 90: 913–917, (1993).
Thanh and Medgyesy, Plant Mol. Biol., 12: 87–93, (1989).
Thomas and Rose, Planta, 158: 329–38, (1983).
Timmermans et al., J. Biotechnol., 14: 333–344, (1990).
Viera and Messing, Meth. Enzymol., 153: 3–11, (1987).
Viera and Messing, Gene, 19: 259–68, (1982).
Weising et al., Ann. Rev. Genet., 22: 421–477, (1988).
Yanisch–Perron et al., Gene, 33: 103–119, (1985).
Yasuda et al., Planta, 174: 235–41, (1988).
Jefferson, pp. 247–263, Genetic Engineering, J.K. Settlow, ed.; Plenum Press, NY, vol. 10, 1988.
Harris, p. 354, The Clamydomonas Sourcebook, Academic Press, San Diego, CA 1989.
Maliga, pp. 133–143, *Perspectives in Genetic and Biochemical Regulation of Photosynthesis*, I. Zeitlich, ed., Alan R. Liss, NY, 1990.
Maliga, pp. 552–562, *Cell Culture and Somatic Cell Genetics in Plants*, vol. I I.K. Vasil, ed., Academic Press, Orlando, 1984.
Boynton et al., pp. 509–516, *Current Research on Photosynthesis*, M. Baltsheffsky, ed., 1990.
Daniell et al. Proc. Natl. Acad. Sci. USA 87: 88–92, Jan. 1990.*
Golds et al. Bio/Technology 11: 95–97, Jan. 1993.*
Gossen et al. TIBTech 12: 58–62, Feb. 1994.*
Staub et al. Plant Cell 4: 39–45, Jan. 1992.*

* cited by examiner

```
                                                               cpt1
  1  GCTCCCCCGC CGTCGTTCAA TGAGAATGGA TAAGAGGCTC GTGGGATTGA
                           cpt2
 51  CGTGAGGGGG CAGGGATGGC TATATTTCTG GGAGCGAACT CCGGGCGAAT
                                 RBS
101  AcGAAGCGCt TGGATACagt tgtagggagg gatttATGGC AGAAGCGGTG
```

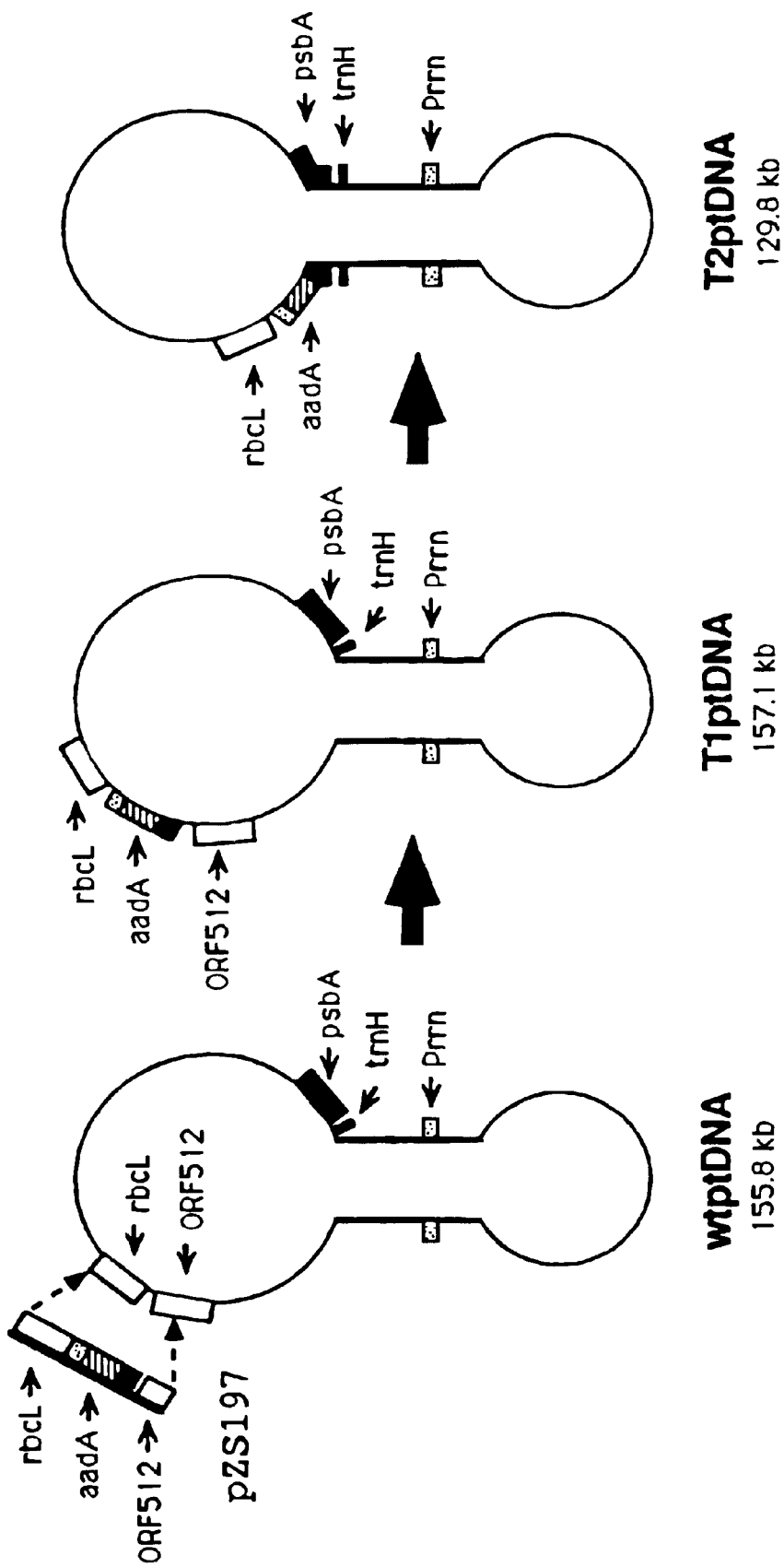

138,448

```
   1 AATTCACCGC CGTATGGCTG ACCGGCGATT ACTAGCGATT CCGGCTTCAT
  51 GCAGGCGAGT TGCAGCCTGC AATCCGAACT GAGGACGGGT TTTTGGGGTT
 101 AGCTCACCTC GCGGGATCGC GACCCTTTGT CCCGGCCATT GTAGCACGTG
 151 TGTCGCCCAG GGCATAAGGG GCATGATGAC TTGACGTCAT CCTCACCTTC
 201 CTCCGGCTTA TCACCGGCAG TCTGTTCAGG GTTCCAAACT CAACGATGGC
 251 AACTAAACAC GAGGGTTGCG CTCGTTGCGG GACTTAACCC AACACCTTAC
 301 GGCACGAGCT GACGACAGCC ATGCACCACC TGTGTCCGCG TTCCCGAAGG
 351 CACCCCTCTC TTTCAAGAGG ATTCGCGGCA TGTCAAGCCC TGGTAAGGTT
 401 CTTCGCTTTG CATCGAATTA AACCACATGC TCCACCGCTT GTGCGGGCCC
 451 CCGTCAATTC CTTTGAGTTT CATTCTTGCG AACGTACTCC CCAGGCGGGA
 501 TACTTAACGC GTTAGCTACA GCACTGCACG GGTCGATACG CACAGCGCCT
 551 AGTATCCATC GTTTACGGCT AGGACTACTG GGGTATCTAA TCCCATTCGC
 601 TCCCCTAGCT TTCGTCTCTC AGTGTCAGTG TCGGCCCAGC AGAGTGCTTT
 651 CGCCGTTGGT GTTCTTTCCG ATCTCTACGC ATTTCACCGC TCCACCGGAA
 701 ATTCCCTCTG CCCCTACCGT ACTCCAGCTT GGTAGTTTCC ACCGCCTGTC
 751 CAGGGTTGAG CCCTGGGATT TGACGGCGGA CTTAAAAAGC CACCTACAGA
 801 CGCTTTACGC CCAATCATTC CGGATAACGC TTGCATCCTC TGTATTACCG
 851 CGGCTGCTGG CACAGAGTTA GCCGATGCTT ATTCCCCAGA TACCGTCATT
 901 GCTTCTTCTC CGGGAAAAGA AGTTCACGAC CCGTGGGCCT TCTACCTCCA
 951 CGCGGCATTG CTCCGTCAGC TTTCGCCCAT TGCGGAAAAT TCCCCACTGC
1001 TGCCTCCCGT AGGAGTCTGG GCCGTGTCTC AGTCCCAGTG TGGCTGATCA
1051 TCCTCTCGGA CCAGCTACTG ATCATCGCCT TGGTAAGCTA TTGCCTCACC
1101 AACTAGCTAA TCAGACGCGA GCCCCTCCTC GGGCGGATTC CTCCTTTTGC
1151 TCCTCAGCCT ACGGGGTATT AGCAGCCGTT TCCAGCTGTT GTTCCCCTCC
1201 CAAGGGCAGG TTCTTACGCG TTACTCACCC GTCCGCCACT GGAAACACCA
1251 CTTCCCGTCC GACTTGCATG TGTTAAGCAT GCCGCCAGCG TTCATCCTGA
1301 GCCAGGATCG AACTCTCCAT GAGATTCATA GTTGCATTAC TTATAGCTTC
1351 CTTGTTCGTA GACAAAGCGG ATTCGGAATT GTCTTTCATT CCAAGGCATA
1401 ACTTGTATCC ATGCGCTTCA TATTCGCCCG GAGTTCGCTC CCAGAAATAT
                                                        -10
1451 AGCCATCCCT GCCCCTCAC GTCAATCCCA CGAGCCTCTT ATCCATTCTC
                          -35
```

↑ 16S RNA

FIG. 16A

```
                 139,968    StuI       139,974
1501  ATTGAACGAC GGCGGGGGAG CtttcgaggactcgAAATCC AACTAGAAAA
1551  ACTCACATTG GGCTTAGGGA TAATCAGGCT CGAACTGATG ACTTCCACCA
1601  CGTCAAGGTG ACACTCTACC GCTGAGTTAT ATCCCTTCCC CGCCCCATCG
1651  AGAAATAGAA CTGACTAATC CTAAGTCAAA GGGTCGAGAA ACTCAACGCC
                        -10                        -35
1701  ACTATTCTTG AACAACTTGG AGCCGGGCCT TCTTTTCGCA CTATTACGGA
                              140,215              ScaI      140,224
1751  TATGAAAATA ATGGTCAAAA TCGGATTCAA TTGTCaaagt acttAACTG
1801  CCCCTATCGG AAATAGGATT GACTACCGAT TCCGAAGGAA CTGGAGTTAC
1851  ATCTCTTTTC CATTCAAGAG TTCTTATGCG TTTCCACGCC CCTTTGAGAC
1901  CCCGAAAAAT GGACAAATTC CTTTTCTTAG AACACATAC AAGATTCGTC
1951  ACTACAAAAA GGATAATGGT AACCCTACCA TTAACTACTT CATTTATGAA
                                          -35
2001  TTTCATAGTA ATAGAAATAC ATGTCCTACC GAGACAGAAT TTGGAACTTG
      -10
2051  CTATCCTCTT GCCTAGCAGG CAAAGATTTA CCTCCGTGGA AAGGATGATT
2101  CATTCGGATC GACATGAGAG TCCAACTACA TTGCCAGAAT CCATGTTGTA
2151  TATTTGAAAG AGGTTGACCT CCTTGCTTCT CTCATGGTAC ACTCCTCTTC
2201  CCGCCGAGCC CCTTTTCTCC TCGGTCCACA GAGACAAAAT GTAGGACTGG
2251  TGCCAACAAT TCATCAGACT CACTAAGTCG GGATCACTAA CTAATACTAA
2301  TCTAATATAA TAGTCTAATA TATCTAATAT AATAGAAAAT ACTAATATAA
2351  TAGAAAAGAA CTGTCTTTTC TGTATACTTT CCCCGGTTCC GTTGCTACCG
2401  CGGGCTTTAC GCAATCGATC GGATTAGATA GATATCCCTT CAACATAGGT
2451  CATCGAAAGG ATCTCGGAGA CCCACCAAAG TACGAAAGCC AGGATCTTTC
2501  AGAAAACGGA TTCCTATTCA AAGAGTGCAT AACCGCATGG ATAAGCTCAC
2551  ACTAACCCGT CAATTTGGGA TCCAAATTCG AGATTTTCCT TGGGAGGTAT
2601  CGGGAAGGAT TTGGAATGGA ATAATATCGA TTCATACAGA AGAAAAGGTT
2651  CTCTATTGAT TCAAACACTG TACCTAACCT ATGGGATAGG GATCGAGGAA
2701  GGGGAAAAAC CGAAGATTTC ACATGGTACT TTTATCAATC TGATTTATTT
2751  CGTACCTTTC GTTCAATGAG AAAATGGGTC AAATTCTACA GGATCAAACC
2801  TATGGGACTT AAGGAATGAT ATAAAAAAAA GAGAGGGAAA ATATTCATAT
2851  TAAATAAATA TGAAGTAGAA GAACCCAGAT TCCAAATGAA CAAATTCAAA
2901  CTTGAAAAGG ATCTTCCTTA TTCTTGAAGA ATGAGGGGCA AAGGGATTGA
            141,366
2951  TCAAGAAAGA TC
```

FIG. 16B

```
  1 GCTCCCCCGC CGTCGTTCAA TGAGAATGGA TAAGAGGCTC GTGGGATTGA
                                                        -35
 51 CCTCAGGGGG CAGGGATGGC TATATTTCTG GGAGCGAACT CCGGGCGAAT
                          -10
101 ACGAAGCGCT TGGATACagt tgtagggagg gatttatgtc accacaaaca
                                  RBS
151 gaggggggaag cggtg
```

SEQUENCE I.D. NO 4 pPRV100A

```
         140,215
                      EcoRI         KpnI           BamHI            SalI
    1781 TTGTCaaagt GAATTCGAGC TCGGTACCCG GGGATCCTCT AGAGTCGACC
         SphI                  SacI            SmaI         XbaI
                                                       140,224
    1831 TGCAGGCATG CAAGCTTact ttAACTG
         PstI       HindIII
```

FIG. 20A pPRV100B

```
         140,215
                      HindIII         PstI           XbaI            SmaI
    1781 TTGTCaaagt AAGCTTGCAT GCCTGCAGGT CGACTCTAGA GGATCCCCGG
                    SphI              SalI                   BamHI
                                                       140,224
    1831 GTACCGAGCT CGAATTCact ttAACTG
         KpnI       SacI    EcoRI
```

FIG. 20B pPRV111B

```
         140,215
1781  TTGTCaaagt GATCCCCCAT GAATAAATGC AAGAAAATAA CCTCTCCTTC
1831  TTTTTCTATA ATGTAAACAA AAAAGTCTAT GTAAGTAAAA TACTAGTAAA
1881  TAAATAAAAA GAAAAAAAGA AAGGAGCAAT AGCACCCTCT TGATAGAACA
1931  AGAAAATGAT TATTGCTCCT TTCTTTTCAA AACCTCCTAT AGACTAGGCC
1981  AGGATCGCTC TAGCTAGACA TTATTTGCCG ACTACCTTGG TGATCTCGCC
2031  TTTCACGTAG TGGACAAATT CTTCCAACTG ATCTGCGCGC GAGGCCAAGC
2081  GATCTTCTTC TTGTCCAAGA TAAGCCTGTC TAGCTTCAAG TATGACGGGC
2131  TGATACTGGG CCGGCAGGCG CTCCATTGCC CAGTCGGCAG CGACATCCTT
2181  CGGCGCGATT TGCCGGTTA CTGCGCTGTA CCAAATGCGG GACAACGTAA
2231  GCACTACATT TCGCTCATCG CCAGCCCAGT CGGGCGGCGA GTTCCATAGC
2281  GTTAAGGTTT CATTTAGCGC CTCAAATAGA TCCTGTTCAA GAACCGGATC
2331  AAAGAGTTCC TCCGCCGCTG GACCTACCAA GGCAACGCTA TGTTCTCTTG
2381  CTTTTGTCAG CAAGATAGCC AGATCAATGT CGATCGTGGC TGGCTCGAAG
2431  ATACCTGCAA GAATGTCATT GCGCTGCCAT TCTCCAAATT GCAGTTCGCG
2481  CTTAGCTGGA TAACGCCACG GAATGATGTC GTCGTGCACA ACAATGGTGA
2531  CTTCTACAGC GCGGAGAATC TCGCTCTCTC CAGGGGAAGC CGAAGTTTCC
2581  AAAAGGTCGT TGATCAAAGC TCGCCGCGTT GTTTCATCAA GCCTTACGGT
2631  CACCGTAACC AGCAAATCAA TATCACTGTG TGGCTTCAGG CCGCCATCCA
2681  CTGCGGAGCC GTACAAATGT ACGGCCAGCA ACGTCGGTTC GAGATGGCGC
2731  TCGATGACGC CAACTACCTC TGATAGTTGA GTCGATACTT CGGCGATCAC
2781  CGCTTCCCTC ATGGTAAAAT CTTGGTTTAT TAATCATCA GGGACTCCCA
2831  AGCACACTAG TTTTCTACAA ATCAAAATAG AAAATAGAAA ATGGAAGGCT
2881  TTTTATTCAA CAGTATAACA TGACTTATAT ACTCGTGTCA ACCAAGGTGT
                             EcoRI
2931  ATGTAGATCG GGAATTCGAG CTCGGTACCC GGGGATCCTC TAGAGTCGAC
2981  CTGCAGGCAT GCAAGCTTCG AGactttAAC TG
              HindIII             140,224
```

FIG. 20C pPRV121A

```
         140,215           EcoRI
1781  TTGTCaaagt CTCGGAATTC GAGCTCGGTA CCCGGGGATC CTCTAGAGTC
1831  GACCTGCAGG CATGCAAGCT TCCGATCTAC ATACACCTTG GTTGACACGA
                      HindIII
1881  GTATATAAGT CATGTTATAC TGTTGAATAA AAAGCCTTCC ATTTTCTATT
1931  TTCTATTTTG ATTTGTAGAA AACTAGTGTG CTTGGGAGTC CCTGATGATT
1981  AAATAAACCA AGATTTTACC ATGAGGGAAG CG.................
      .....................GGCGAGAT CACCAAGGTA
2781  GTCGGCAAAT AATGTCTAGC TAGAGCGATC CTGGCCTAGT CTATAGGAGG
2831  TTTTGAAAAG AAAGGAGCAA TAATCATTTT CTTGTTCTAT CAAGAGGGTG
2881  CTATTGCTCC TTTCTTTTTT TCTTTTTATT TATTTACTAG TATTTTACTT
2951  ACATAGACTT TTTTGTTTAC ATTATAGAAA AAGAAGGAGA GGTTATTTTC
2981  TTGCATTTAT TCATGGGGGA TCactttAAC TG
                                      140,224
``` psbA 5' → aadA → psbA 3' →

FIG. 20D pPRV112A

```
         140,215
1781  TTGTCaaagt AGCTTGAATT AATTCAATGG AAGCAATGAT AAAAAAATAC
1831  AAATAGAAAA GGAAAGGGAG GAAATACAAA AAAATAGAAG AGAAAAGTCA
1881  TACAAAGTTA TATACAAATG ACTACCCCCC TTTTTGTATT TCCTTAATTT
1931  ATTTCCTTAA TTGAATTTCT CTAGCTAGAC ATTATTTGCC GACTACCTTG
1981  GTGATCTCGC C..................................
2781  .......... CGCTTCTGC CATAAATCCC TCCCTACAAC TGTATCCAAG
2831  CGCTTCGTAT TCGCCCGGAG TTCGCTCCCA GAAATATAGC CATCCCTGCC
2881  CCCTCACGTC AATCCCACGA GCCTCTTATC CATTCTCATT GAACGACGGC
                                      EcoRI
2931  GGGGGAGCTT TGGGAATTCG AGCTCGGTAC CCGGGGATCC TCTAGAGTCG
2981  ACCTGCAGGC ATGCAAGCTT CGAGactttA ACTG
                 HindIII                 140,224
``` rps16 3' ← aadA ← Prrn ←

FIG. 20E pPRV113A

```
       140,215
1781  TTGTCaaagt AGCTTGAATT AATTCAATGG AAGCAATGAT AAAAAAATAC
1831  AAATAGAAAA GGAAAGGGAG GAAATACAAA AAAATAGAAG AGAAAAGTCA
1881  TACAAAGTTA TATACAAATG ACTACCCCCC TTTTTGTATT TCCTTAATTT
1931  ATTTCCTTAA TTGAATTTCT CTAGCTAGAC ATTATTTGCC GACTACCTTG
1981  GTGATCTCGC C..............................
              .......... CGCTTCCCC CATGGCATTC CTCTAAGAAC CGGTCTGGAA
2831  TTGATTCAAT TATGGAATCA TGAATAGTCA TTGGTTGGGC TGATGTATAA
2881  ACACCATAAT CTATACTTTG TTCTATATCT ATATACTATA GAGATAGGTG
2931  GATAAATATT TTTCTTTAGT AAGACCCCAT CGCTAATATT AATTTATCTA
2981  ACATATTAAT TAATATTTAA TATATAAATA TATATAGAAA TAATAATAAA
3031  TAAGAATAAT AATAAATAAG ACGAATAAAT GAGTTCTTTT TGATTCTGCA
3081  TCTTCACGTG ACTCAATAGG AGAGATTGAC CTATTTCAGA CTTCTTCAAA
3131  TAGCAAAGAT TCCGCTTATA AGGAATGATT AAAACTATTT ATATTTCTAA
3181  ATTTAGAAAG TTCCCTTTTC GACATCATTA TTTGAAGAAA ATTTGATAGT
3231  TAAAGATCAC TTTTGATCCC GAATTGGGAA TTCGAGCTCG GTACCCGGGG
3281  ATCCTCTAGA GTCGACCTGC AGGCATGCAA GCTTCGAGac tttAACTG
                                        HindIII         140,224
```

FIG. 20F

5'-CGAAAGGTTAGAAATCAACAAAAGA
AAAAGTAAGTGGACCTGACCTA<u>TTGAAT</u>
                        -35
CATGACTATATCCGC<u>TATTCT</u>GATATTAA
              -10
AATTCGATAGAGATGAATTGGAGCtctaga
attcagttgtagggagggatcc<u>atg</u>g-3'

PpabA(L)
```
                    1,819
  1 gaattcgagc tcggtacccG GGCAACCCAC TAGCATATCG AAAGGCTAAT
 51 TTTCTGTAGA GAAGTCCGTA TTTTTCCAAT CAACTTCATT AAAAATTTGA
101 ATAGATCTAC ATACACCTTG GTTGACACGA GTATATAAGT CATGTTATAC
151 TGTTGAATAA AAAGCCTTCC ATTTTCTATT TTCTATTTTG ATTTGTAGAA
                                                    1,596
201 AACTAGTGTG CTTGGGAGTC CCTGATGATT AAATAAACCA AGATTTTACC
251 atgg
```
FIG. 23A

PpabA(S)
```
                    1,735
  1 gaattcgagc tcggtacccG ATCTACATAC ACCTTGGTTG ACACGAGTAT
 51 ATAAGTCATG TTATACTGTT GAATAAAAAG CCTTCCATTT TCTATTTTCT
101 ATTTTGATTT GTAGAAAACT AGTGTGCTTG GGAGTCCCTG ATGATTAAAT
             1,596
151 AAACCAAGAT TTTACCatgg
```
FIG. 23B

PrbcL
```
       57,319
  1 gtcgacTAGT CAGGTATTTC CATTTCAAAA AAAAAAAAAG TAAAAAAGAA
 51 AAATTGGGTT GCGCTATATA TATGAAAGAG TATACAATAA TGATGTATTT
101 GGCAAATCAA ATACCATGGT CTAATAATCA AACATTCTGA TTAGTTGATA
151 ATATTAGTAT TAGTTGGAAA TTTTGTGAAA GATTCCTATG AAAGTTTCA
201 TTAACACGGA ATTCGTGTCG AGTAGACCTT GTTGTTGTGA GAATTCTTAA
                               57,584
251 TTCATGAGTT GTAGGGAGGG ATccatgg
```
FIG. 23C

Prps16
```
       6,656
  1 gaattcggGA TCAAAAGTGA TCTTTAACTA TCAAATTTTC TTCAAATAAT
 51 GATGTCGAAA AGGGAACTTT CTAAATTTAG AAATATAAAT AGTTTTAATC
101 ATTCCTTATA AGCGGAATCT TTGCTATTTG AAGAAGTCTG AAATAGGTCA
151 ATCTCTCCTA TTGAGTCACG TGAAGATGCA GAATCAAAAA GAACTCATTT
201 ATTCGTCTTA TTTATTATTA TTCTTATTTA TTATTATTTC TATATATATT
251 TATATATTAA ATATTAATTA ATATGTTAGA TAAATTAATA TTAGCGATGG
301 GGTCTTACTA AAGAAAAATA TTTATCCACC TATCTCTATA GTATATAGAT
351 ATAGAACAAA GTATAGATTA TGGTGTTTAT ACATCAGCCC AACCAATGAC
401 TATTCATGAT TCCATAATTG AATCAATTCC AGACCGGTTC TTAGAGGAAT
      6,214
451 Gccatgg
```
FIG. 23D

PtrnVrbcL(S)
```
                         102,310
  1 gaattcgagc tcggtagcca ctttGACAAT TGAATCCGAT TTTGACCATT

51 ATTTTCATAT CCGTAATAGT GCGAAAAGAA GGCCCGGCTC CAAGTTGTTC

101 AAGAATAGTG GCGTTGAGTT TCTCGACCCT TTGACTTAGG ATTAGTCAGT
              57,569               57,584
151 TCTATTTCTC GAatacAGTT GTAGGGAGGG ATccatgg
         102,447
```
FIG. 23E Prrn(L) rbcL(S)
```
                        102,561
  1 gaattcgagc tcggtaccca aaGCTCCCCC GCCGTCGTTC AATGAGAATG 51 GATAAGAGGC TCGTGGGATT GACGTGAGGG GGCAGGGATG GCTATATTTC
                                                    57,569
101 TGGGAGCGAA CTCCGGGCGA ATAcGAAGCG CtTGGATACA GTTGTAGGGA
         57,584                              102,677
151 GGGATccatg g
```
FIG. 23F Prrn(S) rbcL(S)
```
                   102,561
  1 gagctcggta cccaaaGCTC CCCCGCCGTC GTTCAATGAG AATGGATAAC 51 AGGCTCGTGG GATTGACGTG AGGGGGCAGG GATGGCTATA TTTCTGGGAG
                      57,569
101 CGAACTCCGG GCGAATtcAG TTGTAGGGAG GGATccatgg
        102,660                      57,584
```
FIG. 23G TpabA(L)
```
      533
  1 tctagagcGA TCCTGGCCTA GTCTATAGGA GGTTTTGAAA ACAAAGGAGC

51 AATAATCATT TTCTTGTTCT ATCAAGAGGG TGCTATTGCT CCTTTCTTTT

101 TTTCTTTTTA TTTATTTACT AGTATTTTAC TTACATAGAC TTTTTTGTTT

151 ACATTATAGA AAAAGAAGGA GAGGTTATTT TCTTGCATTT ATTCATGATT

201 GAGTATTCTA TTTTGATTTT GTATTTGTTT AAATTGTGAA ATAGAACTTG

251 TTTCTCTTCT TGCTAATGTT ACTATATCTT TTTGATTTTT TTTTTCCAAA

301 AAAAAAATCA AATTTTGACT TCTTCTTATC TCTTATCTTT GAATATCTCT
                                                142
351 TATCTTTGAA ATAATAATAT CATTGAAATA AGAAAGAAGA GCTATATTCG 401 acctgcaggc atgcaagctt
```
FIG. 23H TpabA(S)
```
      533
  1 tctagagcGA TCCTGGCCTA GTCTATAGGA GGTTTTGAAA AGAAAGGAGC

51 AATAATCATT TTCTTGTTCT ATCAAGAGGG TGCTATTGCT CCTTTCTTTT

101 TTTCTTTTTA TTTATTTACT AGTATTTTAC TTACATAGAC TTTTTTGTTT
                                                      345
151 ACATTATAGA AAAAGAAGGA GAGGTTATTT TCTTGCATTT ATTCATGggg 201 gatcctctag agtcgacctg caggcatgca agctt
```
FIG. 23I

TrbcL
```
        59,028
  1  tctagagtAG ACATTAGCAG ATAAATTAGC AGGAAATAAA GAAGGATAAC

51  GAGAAAGAAC TCAAGTAATT ATCCTTCGTT CTCTTAATTG AATTGCAATT

101  AAACTCGGCC CAATCTTTTA CTAAAAGGAT TGAGCCGAAT ACAACAAAGA

151  TTCTATTGCA TATATTTTGA CTAAGTATAT ACTTACCTAG ATATACAAGA
                         59,238
201  TTTGAAATAC AAAATCTAGc aagctt
```

FIG. 23J

Trps16
```
        5,087
  1  tctagaGAAA TTCAATTAAG GAAATAAATT AAGGAAATAC AAAAAGGGGG

51  GTAGTCATTT GTATATAACT TTGTATGACT TTTCTCTTCT ATTTTTTTGT

101  ATTTCCTCCC TTTCCTTTTC TATTTGTATT TTTTTATCAT TGCTTCCATT
                         4,939
151  GAATTaattc aagctt
```

FIG. 23K pTNH7

```
   1  gaattcgagc tcggtaccca aaGCTCCCCC GCCGTCGTTC AATGAGAATG
  51  GATAAGAGGC TCGTGGGATT GACGTGAGGG GGCAGGGATG GCTATATTTC
 101  TGGGAGCGAA CTCCGGGCGA ATACGAAGCG CTTGGATACA GTTGTAGGGA
 151  GGGATTTATG TCACCACAAA CAGAGGGGAT TGAACAAGAT GGATTGCACG
 201  CAGGTTCTCC GGCCGCTTGG GTGGAGAGGC TATTCGGCTA TGACTGGGCA
 251  CAACAGACAA TCGGCTGCTC TGATGCCGCC GTGTTCCGGC TGTCAGCGCA
 301  GGGGCGCCCG GTTCTTTTTG TCAAGACCGA CCTGTCCGGT GCCCTGAATG
 351  AACTCCAGGA CGAGGCAGCG CGGCTATCGT GGCTGGCCAC GACGGGCGTT
 401  CCTTGCGCAG CTGTGCTCGA CGTTGTCACT GAAGCGGGAA GGGACTGGCT
 451  GCTATTGGGC GAAGTGCCGG GCAGGATCT CCTGTCATCT CACCTTGCTC
 501  CTGCCGAGAA AGTATCCATC ATGGCTGATG CAATGCGGCG GCTGCATACG
 551  CTTGATCCGG CTACCTGCCC ATTCGACCAC CAAGCGAAAC ATCGCATCGA
 601  GCGAGCACGT ACTCGGATGG AAGCCGGTCT TGTCGATCAG GATGATCTGG
 651  ACGAAGAGCA TCAGGGGCTC GCGCCAGCCG AACTGTTCGC CAGGCTCAAG
 701  GCGCGCATGC CCGACGGCGA GGATCTCGTC GTGACACATG GCGATGCCTG
 751  CTTGCCGAAT ATCATGGTGG AAAATGGCCG CTTTTCTGGA TTCATCGACT
 801  GTGGCCGGCT GGGTGTGGCG GACCGCTATC AGGACATAGC GTTGGCTACC
 851  CGTGATATTG CTGAAGAGCT TGGCGGCGAA TGGGCTGACC GCTTCCTCGT
 901  GCTTTACGGT ATCGCCGCTC CCGATTCGCA GCGCATCGCC TTCTATCGCC
 951  TTCTTGACGA GTTCTTCTGA GCGGGACTGT CGGGTTCGGA TCGATCCtct
1001  agaGCGATCC TGGCCTAGTC TATAGGAGGT TTTGAAAAGA AAGGAGCAAT
1051  AATCATTTTC TTGTTCTATC AAGAGGGTGC TATTGCTCCT TTCTTTTTTT
1101  CTTTTTATTT ATTTACTAGT ATTTACTTA CATAGACTTT TTTGTTTACA
1151  TTATAGAAAA AGAAGGAGAG GTTATTTTCT TGCATTTATT CATGATTGAG
1201  TATTCTATTT TGATTTTGTA TTTGTTTAAA TTGTGAAATA GAACTTGTTT
1251  CTCTTCTTGC TAATGTTACT ATATCTTTTT GATTTTTTTT TTCCAAAAAA
1301  AAAATCAAAT TTTGACTTCT TCTTATCTCT TATCTTTGAA TATCTCTTAT
1351  CTTTGAAATA ATAATATCAT TGAAATAAGA AAGAAGAGCT ATATTCGAcc
1401  tgcaggcatg caagctt
```

Prrn(L) rbcL(S)
← kan
← TpsbA

FIG. 28A pBC85

```
   1  gaattcgagc tcggtaccca aaGCTCCCCC GCCGTCGTTC AATGAGAATG
  51  GATAAGAGGC TCGTGGGATT GACGTGAGGG GGCAGGGATG GCTATATTTC
 101  TGGGAGCGAA CTCCGGGCGA ATACGAAGCG CTTGGATACA GTTGTAGGGA
 151  GGGATccATG GGGATTGAAC AAGATGGATT GCACGCAGGT TCTCCGGCCG
 201  CTTGGGTGGA GAGGCTATTC GGCTATGACT GGGCACAACA GACAATCGGC
 251  TGCTCTGATG CCGCCGTGTT CCGGCTGTCA GCGCAGGGGC GCCCGGTTCT
 301  TTTTGTCAAG ACCGACCTGT CCGGTGCCCT GAATGAACTC CAGGACGAGG
 351  CAGCGCGGCT ATCGTGGCTG GCCACGACGG GCGTTCCTTG CGCAGCTGTG
 401  CTCGACGTTG TCACTGAAGC GGGAAGGGAC TGGCTGCTAT TGGGCGAAGT
 451  GCCGGGGCAG GATCTCCTGT CATCTCACCT TGCTCCTGCC GAGAAAGTAT
 501  CCATCATGGC TGATGCAATG CGGCGGCTGC ATACGCTTGA TCCGGCTACC
 551  TGCCCATTCG ACCACCAAGC GAAACATCGC ATCGAGCGAG CACGTACTCG
 601  GATGGAAGCC GGTCTTGTCG ATCAGGATGA TCTGGACGAA GAGCATCAGG
 651  GGCTCGCGCC AGCCGAACTG TTCGCCAGGC TCAAGGCGCG CATGCCCGAC
 701  GGCGAGGATC TCGTCGTGAC ACATGGCGAT GCCTGCTTGC CGAATATCAT
 751  GGTGGAAAAT GGCCGCTTTT CTGGATTCAT CGACTGTGGC CGGCTGGGTG
 801  TGGCGGACCG CTATCAGGAC ATAGCGTTGG CTACCCGTGA TATTGCTGAA
 851  GAGCTTGGCG GCGAATGGGC TGACCGCTTC CTCGTGCTTT ACGGTATCGC
 901  CGCTCCCGAT TCGCAGCGCA TCGCCTTCTA TCGCCTTCTT GACGAGTTCT
 951  TCTGAGCGGG ACTCTGGGGT TCGATCGAT CCtctagaGT AGACATTAGC
1001  AGATAAATTA GCAGGAAATA AAGAAGGATA AGGAGAAAGA ACTCAAGTAA
1051  TTATCCTTCG TTCTCTTAAT TGAATTGCAA TTAAACTCGG CCCAATCTTT
1101  TACTAAAAGG ATTGAGCCGA ATACAACAAA GATTCTATTG CATATATTTT
1151  GACTAAGTAT ATACTTACCT AGATATACAA GATTTGAAAT ACAAAATCTA
1201  Gc aagctt
```

→ Prrn(L) rbcL(S)
← kan
← TrbcL

FIG. 28B

DNA CONSTRUCTS AND METHODS FOR STABLY TRANSFORMING PLASTIDS OF MULTICELLULAR PLANTS AND EXPRESSING RECOMBINANT PROTEINS THEREIN

This application is a divisional of application Ser. No. 08/189,256 filed Jan. 31, 1994, now U.S. Pat. No. 5,877,402, which is a continuation-in-part of U.S. Ser. No. 08/111,398, filed Aug. 25, 1993, now U.S. Pat. No. 5,451,513, which is a continuation of U.S. Ser. No. 07/518,763, filed May 1, 1990, now abandoned.

Pursuant to 35 U.S.C. §202(c), it is hereby acknowledged that the U.S. Government has certain rights in the invention described herein, which was made in part with funds from the National Science Foundation.

FIELD OF THE INVENTION

This invention relates to the field of plant genetic engineering. In particular, this invention provides DNA constructs and methods for stably transforming plastids of multicellular plants and expressing recombinant proteins in transformed plastids.

BACKGROUND OF THE INVENTION

Transgenic plants are useful to study nuclear gene function and regulation and to improve agronomically important crop plants. Routine application of transgenic technology is made feasible by the alternative methods developed for transformation of nuclear genomes of higher plants. However, transgenic technology has not yet been applied to the genomes of the cytoplasmic organelles (i.e., plastids and mitochondria) of higher plants.

The size of plastid DNA (ptDNA) in higher plants is in the range of 120 kb to 160 kb (Palmer, Ann. Rev. Genet., 19: 325–54, 1985), and encodes the genes involved in plastid maintenance and photosynthesis. By now, three plastid genomes have been sequenced, including that of *Nicotania tabacum* (Shinozaki et al., EMBO J., 5: 2043–49, 1986). In addition to photosynthesis, plastids serve as a compartment for amino acid and lipid biosynthesis. Most if not all the genes involved in these functions are encoded by the nucleus. The enzymes encoded by nuclear genes are synthesized on cytoplasmic ribosomes, and are subsequently transported into the plastids. Expression and accumulation of nuclear gene products and of plastid gene products is coordinated (Gruissem, Cell, 56: 161–70, 1989).

Formation of stably transformed plastid genomes requires integration of the transforming DNA by recombination. That recombination is a mechanism contributing to the evolution of plastid genome is evident when comparing genomes of different plant species. Also, continued recombination through the plastid inverted repeat has been described (Palmer, 1985, supra). It has also been shown that intergenomic plastid recombination occurs in heteroplastidic cells obtained by protoplast fusion (Thanh & Medgyesy, Plant Mol. Biol. 12: 87–93, 1989), and is extensive (Fejes et al., Theor. App. Genet. 79: 28–32, 1990).

Introduction and stable integration of exogenous DNA has been reported recently in the plastid genome of a unicellular alga, *Chlamydomonas reinhardtii* (Boynton et al., Science 240: 1534–38, 1988; Blowers et al., Plant Cell 1: 123–32, 1989). Initial success in transforming the plastid genome of Chlamydomonas by Boynton et al. was made possible by the development of a microprojectile DNA delivery system based on a particle gun that delivers DNA-coated tungsten microprojectiles into the cell. In addition, a powerful selection scheme was applied that relied on complementing nonphotosynthetic deletion mutants. Subsequently, Blowers et al. showed that the Chlamydomonas plastid genome can be expanded by integrating the coding sequence of an *E. coli* enzyme, neomycin phosphotransferase. Transformation of the psbA gene encoding the D1 reaction center polypeptide of photosystem II, and of the 16s rRNA gene conferring resistance to streptomycin and spectinomycin was reported by Boynton et al., p.p. 509–16 in *Current Research in Photosynthesis*, M. Baltsheffsky, ed., 1990.

In higher plant chloroplasts, only transient expression of introduced DNA has been reported. DNA uptake and transient expression by isolated cucumber etioplasts of the large and small subunits of ribulose bisphosphate carboxylase/ oxygenase of *Anacystis nidulans*, or of the *E. coli* enzyme, chloramphenicol acetyltransferase (CAT), has been reported (Daniell and McFadden, Proc. Natl. Acad. Sci. USA 84: 6349–53, 1987). The 5' end of the psbA (pea), and rbcL (maize) plastid genes were fused with the CAT gene. Transient expression of the constructs in chloroplasts of cultured tobacco cells has been reported by Daniell et al., Proc. Natl. Acad. Sci. USA 87: 88–92 (1990) after biolistic delivery. Some of the vectors contained replication origins from ptDNA. CAT activity was sustained longer when the replicon origins were present. CAT activity, however, was not shown to be localized in chloroplasts. CAT activity, therefore, could have been the result of expression in the nucleus, since plastid gene promoters are known to support transcription initiation in the nucleus (Cornelissen and Vandewiele, Nucleic Acids Res. 17: 19–28, 1989).

European Application No. 87305573.5, filed Jun. 23, 1987, by M. C. Cannon and F. C. Cannon, describes a method for producing a plant whose cells express a desired gene by inserting the desired gene into the plastid genome of a plant cell. However, this application does not suggest a method for stably transforming plastids using nonlethal selection, nor does it provide any evidence suggesting that stable transformation was, or could be, achieved.

Transformation of plastids in higher plants was claimed after Agrobacterium-mediated transformation of *N. tabacum* (DeBlock et al., EMBO J. 4: 1367–72, 1985). A CAT gene was engineered for expression in the nucleus, and transgenic clones were selected for resistance to 10 μg/ml chloramphenicol. The authors claim that there was fortuitous integration of the CAT gene into the ptDNA and expression from a plastid promoter. The line was reportedly unstable, and the authors' claims have not been confirmed.

There are several differences between the Chlamydomonas system and higher plants that may be relevant for successful transformation of plastids. Two of these are discussed below. First, the number of plastids, and the number of plastid genomes per cell is much lower in Chlamydomonas than in Nicotiana. Chlamydomonas contains a single plastid, which carries up to 80 identical plastid genomes (Harris, *The Chlamydomonas Sourcebook*, p. 354, Academic Press, San Diego, 1989). In contrast, *Nicotiana tabacum* cells contain a variable number of plastids, about 100 in leaf cells, and 12 to 14 in meristematic cells and dedifferentiated tissue culture cells (Thomas & Rose, Planta 158: 329–38, 1983). In a study with cultured cells the number of plastid genome copies was estimated to be 3,000 to 12,000 per cell (Cannon et al., Plant Cell Reports 4: 41–45, 1985; Yasuda et al., Planta 174: 235–41, 1988).

Another important difference is that Chlamydomonas cells are grown photoautotrophically which allows stringent selection for photosynthetic ability, that is, functional plastids. This facilitates transformation by all proven methods, including Agrobacterium-mediated transformation (Weising et al., Ann. Rev. Genet. 22: 421–77, 1988), electroporation (Fromm et al., Nature 319: 791–93, 1986), calcium phosphate coprecipitation (Krens et al., Nature 296: 72–74, 1982), transformation by high-velocity microprojectiles (Klein et al., Proc. Natl. Acad. Sci. USA 85: 8502–05, 1988), and polyethylene glycol treatment (Negrutiu et al., Plant Mol. Biol. 8: 363–73, 1987). In contrast, higher plants are cultured photoheterotrophically, which reduces the stringency of selection for functional plastids.

Given the large number of plastid genomes in plant cells, the ability to select for the transformed genome in culture is a key element in achieving plastid transformation. Selection markers have been identified by screening culture plant cells for mutants resistant to various substances, such as antibiotics and herbicides. Since most of the selectable plastid genome markers have been developed through cell culture, it is not surprising that most are derived from *Nicotania tabacum* and *Nicotiana plumbaginifolia*, two species that are easy to grow in cell culture and to subsequently regenerate into plants. Resistance to inhibitors of plastid protein synthesis, conferred by mutation in the plastid 16S rRNA and 23S rRNA genes, are the most readily available markers. Other markers include resistance to streptomycin (Maliga et al., Nature 255: 401–02, 1973; Etzold et al., FEBS Lett. 219: 343–46, 1987; Fromm et al., Plant Mol. Biol. 12: 499–505, 1989), spectinomycin (Fromm et al., EMBO J. 6: 3233–37, 1987) and lincomycin (Cseplo & Maliga, Mol. Gen. Genet. 196: 407–12, 1984; Cseplo et al., Mol. Gen. Genet. 214: 295–99, 1988) which are the equivalent rRNA gene mutation used for transformation in Chlamydomonas (Harris et al., 1989, supra).

Plastid genome mutants resistant to triazine herbicides, have also been obtained in cultured Nicotiana cells. Triazine herbicides inhibit photosynthesis by interruption of electron flow at the acceptor of photosystem II. Selection was made feasible in Nicotiana cultures by lowering the concentration of sucrose in the medium, thereby making cellular proliferation partially dependent on photosynthesis (photomyxotrophic cultures; Cseplo et al., Mol. Gen. Genet. 200: 508–10, 1985; Sato et al., Mol. Gen. Genet. 214: 358–60, 1988). Selection for resistance to this class of herbicides is also a nonlethal color selection, resistant mutants being identified by their green color (Cseplo et al., 1985, supra). A mutation in two of the lines was localized to the psbA gene (Pay et al., Nucleic Acids Res. 16: 8176, 1988; Sato et al., 1988, supra). Similar mutant have been found in higher plants under field conditions (Maliga et al., p.p. 133–143 in Perspectives in Genetic and Biochemical Regulation of Photosynthesis, I. Zeitlich, ed., Alan R. Liss, N.Y., 1990), and isolated in Chlamydomonas (Erickson et al., Science 228: 204–07, 1985).

Naturally occurring resistance to tentoxin is also encoded on the plastic genome (Durbin & Uchytil, Biochem. Genet. 15: 1143–45, 1977). Pigment deficiency caused by plastome mutation is frequent, but does not appear to be a useful marker in culture. Pigment mutation in combination with antibiotic resistance mutations, however, have proved important in recovering a recombinant plastid genome (Medgyesy et al., Proc. Natl. Acad. Sci. USA 82: 6960–64, 1985).

The present invention provides a method for stable transformation of the plastids of higher plants. Others have attempted to obtain stable plastic transformation in higher plants, but without success. The present invention also provides efficient and versatile DNA constructs to accomplish stable transformation of plastid genomes and expression of foreign proteins in transformed plastids. These methods and constructs, heretofore unavailable, will enable improvement of useful plant species by genetic engineering of the plastid genome.

SUMMARY OF THE INVENTION

This invention provides DNA constructs and methods for stably transforming plastids of multicellular plants. The DNA constructs of the invention further enable high frequency stable plastid transformation and expression of foreign genes in plastids.

According to one aspect of the present invention, a DNA construct for stably transforming plastids of multicellular plants is provided. The DNA construct contains a transforming DNA, which comprises a targeting segment, a selectable marker gene and at least one cloning site adapted for insertion of an additional DNA segment. The targeting segment comprises a DNA sequence substantially homologous to a pre-determined plastid genomic sequence of a genome within a plastid to be transformed. The targeting segment is of sufficient size to promote homologous recombination with the pre-determined plastid genomic sequence, thereby replacing that sequence in the genome of the transformed plastid. The selectable marker gene is disposed within the targeting segment and confers a non-lethal selectable phenotype to cells containing plastids transformed with the DNA construct. The cloning sites for insertion of additional DNA segments are disposed within the targeting segment relative to the selectable marker gene so as not to interfere with the gene's ability to confer the non-lethal selectable phenotype to the cells containing the transformed plastid.

According to another aspect of the present invention, a DNA construct for high frequency stable transformation of plastids of multicellular plants is provided. This DNA construct includes a targeting segment comprising a DNA sequence substantially homologous to a pre-determined plastid genomic sequence, as described above, of sufficient size to promote homologous recombination with the pre-determined plastid genomic sequence, thereby replacing that sequence in the transformed plastid genome. The transforming DNA further comprises a chimeric selectable marker gene disposed within the targeting segment at a position relative to each terminus of the targeting segment so as not to disrupt the homologous recombination. The chimeric selectable marker gene comprises a selectable marker coding segment encoding a gene product that confers a non-lethal selectable phenotype to cells containing plastids transformed with the DNA construct. The chimeric gene further comprises a 5' regulatory segment, positioned relative to the selectable marker coding segment in the 5' direction to promote expression of the selectable marker coding segment in the plastid. The chimeric gene also comprises a 3' regulatory segment, positioned relative to the selectable marker coding segment in the 3' direction to promote stability of mRNA produced during the expression of the selectable marker coding segment in the plastid. The target segment further comprises at least one cloning site for insertion of additional DNA segments, the cloning sites being disposed within the targeting segment relative to the chimeric selectable marker gene so as not to interfere with the ability of that gene to confer the non-lethal selectable phenotype to cells containing the transformed plastids.

In a preferred embodiment, the additional DNA segments added to the target segment are also chimeric genes, comprising (1) a coding segment encoding a gene product; (2) a 5' regulatory segment positioned relative to the coding segment in the 5' direction to promote expression of the coding segment in plastids; and (3) a 3' regulatory segment positioned relative to the coding segment in the 3' direction to promote stability of mRNA produced during expression of the coding segment in plastids.

According to another aspect of the present invention, a DNA construct is provided for stably transforming plastids of multicellular plants and expressing a gene product within the transformed plastids. This DNA construct comprises a transforming DNA having a targeting segment as described above. The transforming DNA further comprises a selectable marker gene disposed within the targeting segment, which confers a non-lethal selectable phenotype to cells containing plastids transformed with the DNA construct. The construct also contains at least one expressible DNA segment disposed within the targeting segment at a position that does not disrupt homologous recombination with the pre-determined plastid genomic region. The expressible DNA is also positioned relative to the selectable marker gene so as not to interfere with its ability to confer the non-lethal selectable phenotype to cells containing transformed plastids. The expressible DNA segment comprises (1) a coding segment encoding a gene product; (2) a 5' regulatory segment positioned relative to the coding segment in the 5' direction to promote expression of the coding segment in plastids; and (3) a 3' regulatory segment, positioned relative to the coding segment in the 3' direction to promote stability of mRNA produced during expression of the coding segment in the plastids.

In a preferred embodiment of the present invention, the DNA constructs described above are disposed within autonomously replicating vectors. These vectors are preferably of a type that facilitate manipulation of DNA segments contained therein by recombinant DNA techniques.

According to another aspect of the present invention, an expression cassette for producing a chimeric gene for expression in stably transformed plastids having genomes containing that gene is provided. The expression cassette comprises (1) a 5' regulatory segment for controlling expression of a coding segment in plastids; (2) a 3' regulatory segment for promoting stability of mRNA produced during expression of the coding segment in plastids; and (3) a cloning segment connecting the 5' regulatory segment and the 3' regulatory segment, and being adapted for insertion of a coding segment, such that expression of the inserted coding segment is controlled by the 5' regulatory segment and the mRNA produced during that expression is stabilized by the 3' regulatory segment.

In a preferred embodiment of the invention, the cloning segment of the aforementioned expression cassette further includes a stuffer segment. The stuffer segment is excised and replaced by a coding segment, to produce a chimeric gene for expression in plastids.

According to another aspect of the present invention, a 5' regulatory segment for expressing a coding segment in plastids is provided. The 5' regulatory segment controls expression of a coding segment in plastids when it is positioned relative to the coding segment in the 5' direction to promote such expression. The 5' regulatory segment comprises a promoter region and a 5' untranslated region, with the promoter region being positioned immediately adjacent to the 5' untranslated region in the 5' direction. The 5' untranslated region comprises a DNA sequence that encodes a ribosome binding site, and may also comprise other regulatory sequences. The 5' untranslated region is also referred to herein as a "leader sequence."

In a preferred embodiment, the 5' regulatory segment described above further comprises a 5' translated region positioned immediately adjacent to the 5' untranslated region in the 3' direction. This translated region comprises a translational start codon positioned in translational reading frame with the coding segment whose expression is controlled by the 5' regulatory segment.

According to another aspect of the present invention, multicellular plant cells and plants having stably-transformed plastids may be obtained through the use of a DNA construct comprising a transforming DNA having a targeting segment, a selectable marker gene disposed within the targeting segment and at least one cloning site adapted for insertion of additional DNA segments, as described above. The transforming DNA is delivered into the plastid by one of several means known in the art, thereby enabling integration of the transforming DNA without interfering with the normal function of the plastid genome. Cells or tissues containing the potentially transformed plastids are placed on a non-lethal selection medium in which transformed plastids having the non-lethal selectable phenotype are preferentially maintained, while non-transformed plastids are lost. Cells or tissues are maintained on the selection medium until they have reached a homoplasmic condition, in which substantially all of the plastids of the cell or tissue have been transformed. The cells or tissues expressing the non-lethal selectable phenotype are selected, and thereafter may be regenerated to obtain plants.

BRIEF DESCRIPTION OF THE DRAWINGS

(FIG. 1A): transforming DNA comprises targeting segment (TS) in which is disposed a selectable marker gene (SMG). Possible locations for cloning sites (CS) are indicated. (FIG. 1B): transforming DNA comprises target segment (TS) into which is inserted a chimeric gene comprising a 5' regulatory segment (5' RS), a selectable marker coding segment (SMCS) and a 3' regulatory segment (3' RS). Possible locations for cloning sites (CS) are indicated.

(FIG. 3C): Physical map of the probed region of wild-type (wt) and transgenic (T) ptDNA and the relative position of the probe and of the 16S rDNA (highlighted) in plasmid pZS148. Expected sizes of hybridizing fragments are listed. Restriction endonucleases: RV, EcoRV; H, HindIII; P, PstI; S, SacI.

(FIG. 4A): PstI fragment pattern of ptDNA. λ DNA digested with HindIII or HindIII/EcoRI were size standards. Sizes of PstI fragments in the Nt(pbg) recipient are given. The 18.8-kb and 18.9-kb fragments do not separate and are marked as a doublet. The 4.4-kb, 14.4-kb and 19.3-kb fragments in the Nt(pbg*)T2D ptDNA are marked with asterisks. (FIG. 4B): PstI map of ptDNA derived from data shown in (A). The circular map was linearized at base pair 1388 to include complete PstI fragments. Junctions of base pair 1 and base pair 155,844 are given in parentheses. Sizes of fragments are given in kilobase pairs. The filled bars indicate repeated regions. The map position of the 3.7-kb 16S rDNA fragment, contained in plastid vector pZS148, is shown. The 23.7- and 18.8-kb Nt(pbg) fragments disappear due to integration of the PstI linker; new 4.4-, 14.4-, and 19.3-kb fragments that form as the result are marked (*).

(FIG. 6C): DNA probes. (FIG. 6D): T1ptDNA formed by recombination (dashed lines) via rbcL and ORF512 sequences. (FIG. 6E): Lineup of regions of donor DNA and of the wild-type plastid genome involved in forming T2ptDNA by recombination via rbcL and psbA 3'-end sequences. The bold line in T2ptDNA indicates the sequence in the repeated region. Restriction endonuclease recognition sites: RI, EcoRI; RV, ECORV; NI, NcoI; SII, SacII; XI, XbaI. Maps are to scale.

FIGS. 7A–7C—Wild-type (A) and transformed (B and C) plastid genomes. (FIG. 7A): Recombination sites between homologous flanks in pZS197 and the wild-type plastid genome (wtpDNA) are shown by arrows. (FIG. 7B): T1ptDNA is the product of recombination shown in A. (FIG. 7C): T2ptDNA has a 26-kb deletion and duplication of the psbA 3' region and trnH. Note that the 5'-end of psbA is distal to trnH. Inverted repeat sequences are paired so that the large and small single-copy regions form loops. Genomes are not drawn to scale. psbA, trnH, rbcL, and ORF512 are plastid genes.

(FIG. 9A): Total cellular DNA was digested with EcoRI and EcoRV restriction endonucleases for which there are no sites in plasmid pTNH32. Blots were probed with the targeting plastid DNA fragment encoding the rbcL and ORF512 genes (P1 in FIG. 9D). Lanes contain DNA from wild-type tobacco (wt); P70 and P107 callus; P70A, P70B, P107A and P107B from leaves of transplastomic subclones; N4, N19, N46, N47, N92 and N115 from leaves of nuclear transformants. (FIG. 9B): Same as (A), except that the blot was probed with the kan coding region (P2 in FIG. 9D). (FIG. 9C): Confirmation of homoplasmy in P70A seedlings (second seed generation) and wild-type (wt) seedlings by probing with the targeting sequences (probe P1 in FIG. 9D). (FIG. 9D): DNA probes. (FIG. 9E): Transplastome (T-ptDNA) formed by recombination (dashed lines) via rbcL and ORF512 sequences. Donor DNA is plastid targeting sequence with chimeric kan in vector PTNH32; ptDNA is a segment of the wild-type plastid DNA. Abbreviations for restriction endonuclease recognition sites: RI, EcoRI; RV, ECORV; NI, NcoI; SII, SacII; XI, XbaI. The EcoRV site in plasmid PTNH32 that was eliminated during cloning is in brackets. Maps are to scale.

(FIG. 11A): The PT92 plastid genome (PT92 DNA). The region of pJS80 DNA integrated into the repeat region (heavy arcs) by two homologous recombination events (broken lines) is shown beneath the diagram of PT92. The chimeric uidA gene was cloned into the DraI site of pJS75 between the trnV and 16SrDNA genes. The 16SrDNA gene encodes the selected spectinomycin resistance (spcr) mutation. Location of single copy psbA gene is also shown. Arrows indicate sites of initiation and direction of transcription. (FIG. 11B): Southern hybridization to confirm maternal inheritance of the uidA gene in crosses. Data is shown for five seedlings each, obtained by selfing (S) or from crosses using PT92 as female parent (F1), or from reciprocal crosses where PT92 was used as pollen parent (RF1). Total cellular DNA digested with HindIII and DraI enzymes was probed with the 6-kb wild-type DNA fragment containing the trnV and 16SrDNA genes. The PT92 line contains two hybridizing bands (4.4 and 3.8 kb) due to the presence of the DraI site in the 3'-end of the chimeric gene. Wild-type plastid genome copies are absent in PT92 selfs and F1 seedlings.

(FIG. 12A): Accumulation of plastid uidA (2 kb) and psbA (1.2 kb) mRNAs in leaves and roots. Northern blot of total cellular RNA from leaf (1 µg) or roots (20 µg) was hybridized with mixed uidA and psbA coding region probes. mRNA of the 35SuidA nuclear gene is visible only in the root RNA sample. Higher molecular weight RNA species in PT92 represent read-through transcription. (FIG. 12B): GUS (68 kDa) and D1 (32 kDa) protein accumulation in leaves and roots (100 µg total protein per lane). The immunoblot was probed with GUS (1:600 dilution) and subsequently with D1 (1:800 dilution) protein antisera. A dilution series of PT920 leaf sample, and a GUS standard (0.1 µg; lane C) are also shown.

(FIG. 13A): GUS activity. (FIG. 13B): Accumulation of uidA mRNA. Northern blots with 5 µg total cellular RNA per lane (with the exception of lane 11 days/10 h which contained 2.5 µgRNA) were probed with the uidA coding region. Dilution series (1:2, 1:5 and 1:10) were prepared from 11-day old seedlings illuminated for 24 h.

(FIG. 14A): GUS activity in PT92 seedlings. (FIG. 14B): Immunoblot analysis of GUS and D1 accumulation (10 µg total protein per lane). The immunoblot was probed with GUS (1:800 dilution) and subsequently with D1 (1:800 dilution) protein antisera. A dilution series from the light grown PT 92 sample and a GUS standard (50 ng; lane C) are also shown. Note accumulation of a primary D1 degradation product (d) in illuminated samples (Greenberg et al., EMBO J., 6: 2865–69, 1987) (FIG. 14C): Accumulation of uidA and psbA mRNAs. Northern blot with total cellular RNA (5 µg per lane) was hybridized with mixed uidA and psbA coding region probes. Dilution series is from the PT92-L sample.

(FIG. 15A): Separation of radioactive polypeptides in 10% SDS-PAGE after immunoprecipitation with D1 or GUS antisera from protein extracts containing equal amounts of acid-insoluble radioactivity ($2\times10^5$ d.p.m. per sample). Pulse-labeling was carried out by incubating cotyledons with [$^{35}$S] methionine for 2 h in the light (1, 10,000 1×) or after a shift into dark for 2 or 4 h (2–4D and 4–6D, respectively). In addition, cotyledons that had been pulse-labeled in the light were chased with 10 mM non-radioactive methionine in the dark for 4 h (L/4D). Nt-L is a sample from light-grown, non-transformed seedlings. MW denotes position of molecular weight markers. (FIG. 15B): PsbA and uidA mRNA levels. Samples were treated as for FIG. 15A, except that 10 mM non-radioactive methionine was used for the pulse. Northern blot (5 µg total cellular RNA per lane) was hybridized with mixed uidA and psbA coding region probes.

FIG. 16—The plastid targeting fragment in plasmid pPRV1 (Sequence I.D. No. 3). The first and last nucleotides correspond to nucleotides 138,448 and 141,386 of tobacco ptDNA. The coding regions of the 16SrRNA and trnV genes, and of ORF70B and ORF131 are framed. Nucleotides derived from the ptDNA are in capital letters; those inserted during vector construction are in lower case. The StuI and ScaI cloning sites, and the −10 and −35 promoter elements for the ribosomal RNA operon, trnV and the rps7/12 operon are underlined. The horizontal arrow indicates the mapped transcription initiation sites for the rps12/7 operon.

FIGS. 17SA–17C—Integration of aadA by homologous recombination in the ptDNA. Total cellular DNA was isolated from non-transformed tobacco leaves (wt), and from leaves of plants transformed with plasmids;.pOVZ12 (Nt-pOVZ12), pOVZ13 (Nt-pOVZ13) and pOVZ15 (Nt-pOVZ15). The DNA was digested with the EcoRI and EcoRV restriction endonucleases, and the DNA gel blots were probed with.

FIGS. 18A–18C—Transplastomes with promoters as short, direct repeat DNA elements. (FIG. 18A): The Prrn sequence (Sequence I.D. No. 4; identical in part to Sequence I.D. Nos. 1 and 2) forms a 117 nucleotide direct repeat; (FIG. 18B): and the PtrnV sequence (Sequence I.D. No. 5) forms a 137 nucleotide direct repeat in ptDNA of plants transformed with plasmids pZS208 and pZS209, respectively. Location of repeats is marked by arrows. DNA sequence of the chimeric promoters is given below the maps. Nucleotides derived from the ptDNA are in upper case. The −10 and −35 regulatory elements and sequences encoding the ribosome binding site (GGUGG) and translational initiation codon (AUG) are underlined.

FIGS. 20A–20F—DNA sequence of the selectable marker genes and MCS in the pPRV vectors. For pPRV100, sequence of MCS is given for pPRV100A (FIG. 20A, Sequence I.D. No. 6) and pPRV100B (FIG. 20B, Sequence I.D. No. 7). Sequence for the following vectors is given in one orientation: pPRV111A (FIG. 20C, Sequence I.D. No. 8), pPRV121A (FIG. 20D, Sequence I.D. No. 9), pPRV112A (FIG. 20E, Sequence I.D. No. 10), pPRV113A (FIG. 20F, Sequence I.D. No. 11). The entire aadA coding region is included in the pPRV111A sequence, and partial aadA sequence is given for the rest of the vectors. Nucleotides derived from the ScaI restriction site (FIG. 16) are in bold face. Sequence of aadA and the linked MCS in plasmid pPRV211A is identical with that in pPRV111A, except that it has been inserted into the StuI site of pPRV1.

(FIG. 21A): The map of transplastomes with the LRP-5'/uidA/rps16-3' reporter gene introduced in both orientations. Black boxes indicate the LRP sequence, horizontally striped boxes depict the rps16-3' end. Wavy horizontal lines represent transcripts derived from the transgene promoters. (FIG. 21B): DNA sequence of the chimeric LRP 5'-region (Sequence I.D. No. 12). The nucleotides encompassing the LRP are shown in uppercase (nucleotides 33,477–33,583); the synthetic leader sequence is shown in lower case. The putative −10 and −35 elements, and the translational initiation codon (AUG) are underlined. (FIG. 21C): Light-induced mRNA accumulation from the LRP in tobacco plastids. RNA gel blots were probed with the uidA coding sequence. Note accumulation of mRNA in light-grown plants (L), and absence of mRNA plants dark-adapted for 3 days (D). Only monocistronic message is present in the pLAA35A plants in which uidA is oriented towards the rps 12/7 operon. The blot was stripped and probed with a 16SrDNA probe to control for amounts of RNA loaded.

(FIG. 22A): The uidA genes carried in plasmids pLAA23, pLAA24 and pIK100 are inserted between the trnV gene and rps12/7 operon. (FIG. 22B): The uidA gene from plasmid pJS80 is inserted between the trnV gene and the rrn operon. (FIG. 22C): uidA transgenes in plasmids pJS95, pJS94, pJS118, pJS127, pJS93, pJS125 and pJS139 are linked to aadA and targeted to the intergenic region between rbcL and accD. Transforming plasmids are listed below the maps with the respective 5' and 3' regulatory segments. Wavy horizontal lines represent uidA-containing transcripts derived from the transgene promoters; arrows indicate the direction of transcription. Percentages listed next to the transcripts refer to proportion of total uidA-containing messages. Open boxes represent coding regions for the indicated genes; hatched and filled boxes represent regulatory segments. The selectable marker gene aadA, and plastid genes rps12, trnV, 16SrDNA, rbcL and accD are shown.

FIG. 23—DNA sequences of 5'- and 3'-regulatory segments in plastid expression cassettes. 5'-regulatory regions are designated by P for promoter, and the name of the gene from which they derive. In the case of chimeric 5'-regulatory regions, the gene which is the source of the promoter is listed first, the source of leader sequence second. If multiple constructs are available, versions are distinguished by (S) for short and (L) for long. The 3'-regulatory regions are designated by T for terminators of transcription (however inefficient) and the name of the gene from which they are derived. Nucleotides derived from the ptDNA are in capital letters, those added or modified during construction are in lower case. The numbers indicate position of the first and last nucleotides in the ptDNA sequence (according to Shinozaki et al., 1986). For promoters, note EcoRI and/or SacI cloning sites upstream of promoters and the NcoI site downstream (encompassing the translational initiation codon). The only exception is PrbcL, which may be isolated as a SalI/NcoI fragment. Terminators are engineered as XbaI/HindIII fragments. Coding regions of bacterial genes may be inserted in the cassettes as NcoI/XbaI fragments. PpsbA(L) is Sequence I.D. No. 13; PpsbA(S) is Sequence I.D. No. 14; PrbcL is Sequence I.D. No. 15; Prps16 is Sequence I.D. No. 16; PtrnVrbcL(S) is Sequence I.D. No. 17; Prrn(L)rbcL(S) is Sequence I.D. No. 18; Prrn(S)rbcL(S) is Sequence I.D. No. 19; TpsbA(S) is Sequence I.D. No. 20; TpsbA(S) is Sequence I.D. No. 21; TrbcL is Sequence I.D. No. 22; and Txps16 is Sequence I.D. No. 23. Sources of the regulatory regions are the following plasmids: pJS25 for PpsbA(L) and TpsbA(L); pOVZ20 for PpsbA(S) and TpsbA(S); pIK100 for PrbcL and TrbcL; pHC61 for Prps16; pZS195 for Prrn(L)rbcL(S); pZS177 for Prrn(S)rbcL(S); pZS196 for PtrnVrbcL(S).

(FIG. 24A): Steady-state mRNA levels for uidA. For constructs pLAA23, pLAA24 and pIK100 two transcripts are detected by the uidA coding region probe. These correspond to a monocistronic uidA and a dicistronic uidA/aaadA mRNA, as diagrammed in FIG. 22A. Constructs pJS94, pJS118 and pJS95, targeted downstream of the rbcL gene in the single copy region, give rise to multiple uidA-containing transcripts, as diagrammed in FIG. 22C. (FIG. 24B): GUS activities measured in duplicate in leaves of transgenic plants. Data are shown for the constructs listed in FIG. 22A and B, and for a subset of the constructs depicted in FIG. 22C. Activities are graphed using a logarithmic scale.

(FIG. 25A): Steady-state mRNA levels for uidA. Multiple uidA-containing transcripts are detected by the uidA coding region probe. Transcript origins are depicted in FIG. 22C. (FIG. 25B): GUS activities. Data area shown for a subset of constructs listed in FIG. 22C. GUS activities are graphed using a linear scale.

(FIG. 27A): Steady-state mRNA levels for uidA. To the left are shown RNA from plants transgenic for constructs targeted to the repeat region, giving rise to two uidA-containing transcripts (see FIG. 22A). To the right are shown RNAs for transgenic plants containing constructs inserted in the single copy region downstream of rbcL. Mono and polycistronic transcript origins are depicted in FIG. 22C. (FIG. 27B): GUS activities from leaves of transgenic plants, plotted on a linear scale.

FIG. 28—DNA sequence of the engineered kan genes expressed in plastids. (FIG. 28A): The Prrn(L)rbcL(S)/kan/TpsbA(L) construct in plasmid pTNH7 (Sequence I.D. No. 27), that was used to generated plasmid pTNH32 (Carrer et al., 1993). In bold around the ATG are 36 nucleotides that are a perfect match with the rbcL sequence. Note that the coding region is translationally fused with the first 5 amino acids of the Rubisco large subunit. (FIG. 28B): Prrn(L)rbcL(S)/kan/TrbcL construct in plasmid pHC85 (Sequence I.D. No. 28). In bold are the 16 nucleotides upstream of the ATG which are identical to the rbcL leader.

(FIG. 29A): Immunoblot confirms accumulation of NPTII in roots and leaves. Lanes contain protein extracts from the leaves (L; 0.5 μg) and roots (R; 5 μg) wild-type plants (wt), and plants transformed with plasmids pTNH32 (70) and pHC85 (85-6). Purified NPTII standard, and a dilution series of both the 70 leaf sample and NPTII (1:10; 1:50) are shown. Note that NPTII accumulates to 1% of total cellular protein in the NtpTNH32–70 leaf sample. (FIG. 29B): Steady-state mRNA levels in leaves. The kan probe in RNA gel blots detected a monocistronic (lower band) and dicistronic (upper band) mRNAs. The kan gene in pTNH32 and pHC85 transformants is inserted between the rbcL/accD, and trnv/rps12/7 genes, respectively.

(FIG. 30A): Map of the region containing the uidA gene, with the sequence below (Sequence I.D. No. 29) of the rbcL stop codon and the nucleotide (arrow) where the rbcL(S) leader of the promoterless uidA gene (in plasmid pJS139, a 3' portion of Sequence I.D. No. 25), or the promoter-containing uidA (Prrn(S)rbcL(S)) (Sequence I.D. No. 25 with a different 5' restriction site); in plasmid pJS118)) is fused with the rbcL 3' UTR. Unfilled boxes represent the coding regions of transgenes uidA, aadA, and plastid genes rbcL and accD. Filled boxes depict transgene 5' and 3' regulatory regions. Horizontal arrows diagram the expected transcripts originating from the rbcL and uidA transgene promoters. Note for the promoterless test construct, pJS139, the absence of transcripts originating from the uidA 5' region. Capital letters mark ptDNA sequences, lower case represent engineered nucleotides. The RBS in each leader is boxed. Bold letters constitute the rbcL(S) sequence. (FIG. 30B): RNA gel blot of plants transformed with plasmids pJS139 and pJS118, probed with the uidA coding region. Note lack of monocistronic mRNAs in plants transformed with the promoterless construct in pJS139.

DETAILED DESCRIPTION OF THE INVENTION

Figure 1A:
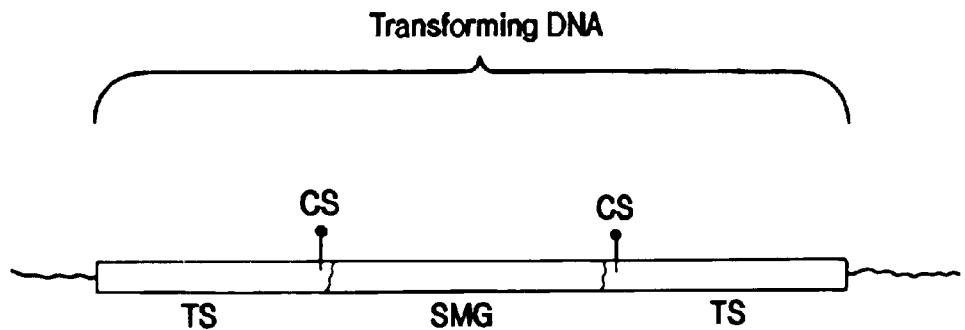
FIGS. 1A–1B—Schematic diagrams of two DNA constructs of the invention. Bracket indicates region comprising transforming DNA; wavy lines indicate vector DNA.

In accordance with the present invention, methods and DNA constructs are provided to effect stable transformation of plastids of multicellular plants. The methods of the invention rely on the use of a non-lethal selection means, which imparts a selectable phenotype to cells containing transformed plastids. In accordance with the present invention, a number of DNA constructs are provided for high-frequency transformation of plastids and targeted manipulation of the plastid genome. Such manipulations include gene replacement, gene deletion, insertion of foreign genes and expression of recombinant proteins in plastids. This invention further provides DNA constructs for differentially regulated expression of recombinant proteins in plastids, including constitutive expression, tissue-specific expression and light-inducible expression. The methods and DNA constructs described herein have heretofore been unavailable for multicellular plants.

The following definitions will facilitate the understanding of the subject matter of the present invention:

Heteroplasmic

Refers to the presence of a mixed population of different plastid genomes within a single plastid or in a population of plastids contained in plant cells or tissues.

Homoplasmic

Refers to a pure population of plastid genomes, either within a plastid or within cells and tissues. Homoplasmic plastids, cells or tissues are genetically stable because they contain only one type of platid genome. Hence, they remain homoplasmic even after the selection pressure has been removed, and selfed progeny are also homoplasmic. For purposes of the present invention, heteroplasmic populations of genomes that are functionally homoplasmic (i.e., contain only minor populations of wild-type DNA or transformed qenomes with sequence variations) may be referred to herein as "functionally homoplasmic" or "substantially homoplasmic." These types of cells or tissues can be readily purified to homoplasmy by continued selection on the non-lethal selection medium. Most seed progeny of such plants are homoplasmic in the absence of selection pressure, due to random sorting of plastid genomes.

Plastome

The genome of a plastid.

Tranoplastome

A transformed plastid genome.

Transformation of Plastids

Stable integration of transforming DNA into the plastid genome that is transmitted to the seed progeny of plants containing the transformed plastids.

Transient Gene Expression in Plastids

Expression of genes in plastids from DNA introduced into plastids that is not incorporated into the plastid genome.

Non-lethal Selectable Marker

The term "selectable marker" refers to a phenotype that identifies a successfully transformed organelle, cell or tissue, when a gene or allele encoding the selectable marker is included in the foreign DNA used for transformation. Commonly used selectable markers include resistance to antibiotics, herbicides or other compounds, which would be lethal to cells, organelles or tissues not expressing the resistance gene or allele. Selection of transformants is accomplished by growing the cells or tissues under selective pressure, i.e., on media containing the antibiotic, herbicide or other compound. If the selectable marker is a "lethal" selectable marker, cells which express the selectable marker will live, while cells lacking the selectable marker will die. If the selectable marker is "non-lethal", transformants (i.e., cells expressing the selectable marker) will be identifiable by some means from non-transformants, but both transformants and non-transformants will live in the presence of the selection pressure.

A selectable marker may be non-lethal at the cellular level, but lethal at the organellar level; such is the case for the selectable marker preferred for use in the present invention. For example, the antibiotic spectinomycin inhibits translation of mRNA to protein in plastids, but not in the cytoplasm. Plastids sensitive to spectinomycin are incapable of producing proteins comprising the photosynthetic apparatus, as well as other proteins required for plastid survival. In the presence of spectinomycin, cells comprising such plastids are kept alive by growing them under photoheterotrophic conditions (i.e., supplying an exogenous carbon source), but the plastids therein do not survive, and the cells or tissues are bleached white, instead of being green. In contrast, plastids expressing the selectable phenotype of spectinomycin resistance survive and multiply and the cells containing such plastids are green. In a mixed population of cells containing transformed and non-transformed plastids, the sensitive non-transformants will disappear during the course of plastid/cell division under selection pressure, and eventually only transformed plastids will comprise the plastid population (homoplasmic cells or tissues, as defined above). Thus, for the purposes of the present invention, a non-lethal selectable marker refers to non-lethality at the cellular level, wherein sensitive cells or tissues can be grown in the selective medium, but resistant tissues are readily identifiable therefrom.

Transforming DNA

Refers to DNA introduced into plastids that becomes part of a plastid genome by homologous recombination.

The detailed description set forth in Sections I–III below describes preferred methods for making and using the DNA constructs of the present invention and for practicing the methods of the invention. Any molecular cloning and recombinant DNA techniques not specifically described are carried out by standard methods, as generally set forth, for example, in Sambrook et al., "DNA Cloning, A Laboratory Manual," Cold Spring Harbor Laboratory, 1989.

In the Detailed Description and Examples set forth hereinbelow, transformation of tobacco chloroplasts is exemplified. References made to positions and sequences on the tobacco chloroplast genome are taken from Shinozaki et al., EMBO J., 5: 2043–49 (1986) (hereinafter "Shinozaki et al."), which discloses the complete nucleotide sequence of the *Nicotiana tabacum* chloroplast genome. Although tobacco is exemplified, it will be appreciated by those skilled in the art that the DNA constructs and methods of the present invention can easily be applied or adapted to other types of plastids, as well as other plant species, as described in greater detail in the sections below.

I. Stable Transformation of Plastid Genomes

Plastid transformation requires: (1) a method for delivering DNA through the double membrane of the plastid; (2) integration of the heterologous DNA without interfering with the normal function of the plastid genome; and (3) efficient selection for the transplastome. In accordance with the present invention, it has been discovered that the selection criterion for identifying transplastomes is critical to the success of stable plastid transformation in higher plants. Accordingly, the selection technique of the present invention employs DNA encoding a non-lethal selectable phenotype ("selectable marker") in the transforming DNA. As explained in detail in Example 1 ("Discussion" section), non-lethal selection greatly facilitates obtaining transplastomic lines, due in part to the large number of identical plastid genome copies present in each plant cell (3,000–12,000 copies localized in up to 100 plastids in tobacco, as compared with 80 copies carried by a single plastid in Chlamydomonas). Non-lethal selection in higher plants allows sufficient time for the resistant plastid genome copies to increase in numbers to allow phenotypic expression.

A. Requirements for Transformation Vector

DNA constructs useful for practicing the present invention comprise, at minimum, (1) a DNA sequence homologous to a region of the plastid genome being transformed (sometimes referred to herein as a "targeting segment" or "targeting fragment"), of sufficient length to ensure the homologous recombination event necessary for incorporation of the transforming DNA into the plastid genome; and (2) a DNA sequence encoding a non-lethal selectable phenotype (sometimes referred to herein as "selectable marker gene"). In one embodiment of the present invention, the targeting segment and the DNA sequence encoding the selectable phenotype are one and the same, inasmuch as the targeting fragment comprises a segment of plastid DNA that is actually a mutant plastid gene that confers resistance to a substance that would normally be lethal to plastids, such as spectinomycin, an inhibitor of plastid protein synthesis. This embodiment is shown schematically in FIG. 1A. In another embodiment, the selectable marker gene comprises non-plastid sequences inserted into the targeting segment, such that it is flanked on either side by a portion of the targeting segment. This embodiment is described in greater detail in Section II below. In either embodiment, the targeting segment directs the insertion of the transforming DNA into a specific position on the plastid genome. Accordingly, a suitable target site on the plastid genome must be selected so as not to disrupt expression of essential plastid genes. The availability of gene mapping information for plastid genomes of many species facilitates the choice of suitable insertion sites, as does the strong conservation among plastid genomes across species.

Figure 2:
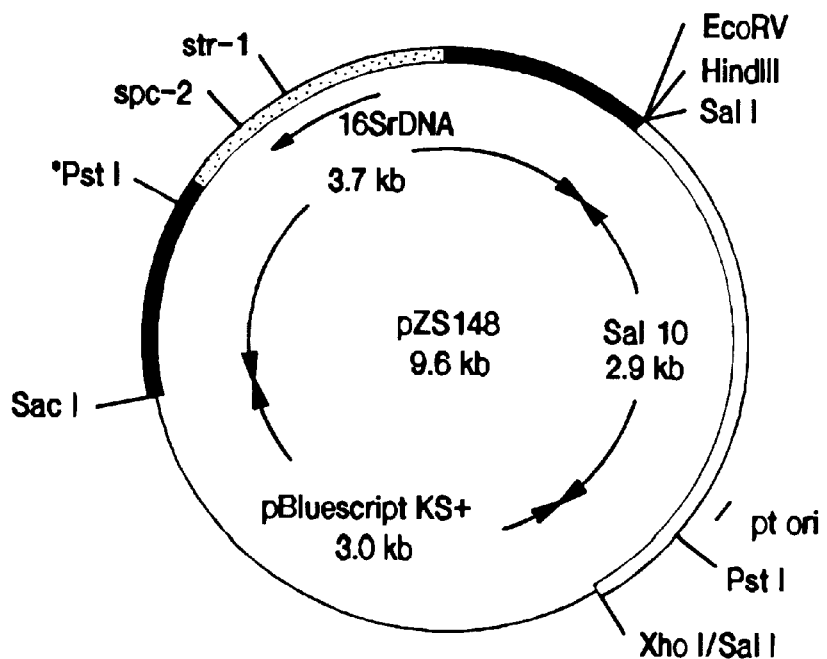
FIG. 2—pZS148 plastid transformation vector. The Bluescript vector contains the 3.7-kilobase (kb) SacI-EcoRV fragment from the SPC2 plastid DNA (ptDNA). The 16SrDNA is highlighted, and the relative positions of streptomycin (str-1) and spectinomycin (spc-2) resistance mutations and of the PstI linker (*) are shown. The 2.9-kb SalI fragment includes a region implicated in ptDNA replication (pt ori).

An example of a non-lethal selectable phenotype preferred for practice of the present invention is resistant to a substance which inhibits protein synthesis by plastids, such that cells which have acquired the non-lethal selectable phenotype are selected for by contacting the cells with that substance. In one embodiment, the plastid DNA encoding the non-lethal selectable phenotype may comprise a 16S ribosomal DNA (rDNA) mutant, which confers resistance to spectinomycin, streptomycin or to both antibiotics simultaneously. The resulting non-lethal selectable phenotype is green pigmentation. An example of a simple transformation vector, in which the targeting fragment comprises the above-described mutant 16S rDNA, is pZS148, shown in FIG. 2.

Expression of heterologous genes that modify non-lethal antibiotics, such as streptomycin or spectinomycin, by phosphorylation, adenylation or acetylation also are suitable for non-lethal selection of transplastomes. The advantageous use of such heterologous genes is described in greater detail in Section II below.

Another example of a non-lethal selectable phenotype is resistance to a photosystem II herbicide, such as a triazine herbicide (e.g., atrazine). This phenotype not only provides non-lethal selection, but provides herbicide resistance. Resistant mutants in higher plants are currently available, but their fitness is reduced to altered photosynthetic electron transport. Plastid mutations have been developed in Chlamydomonas that are resistant to photosystem II herbicides but have normal electron transport. Similarly, resistance to photosystem II herbicides, such as atrazine, diuron, or DCMU, based on mutations in the psbA plastid gene, introduced into chloroplasts by in vitro mutagenesis of cloned genes and transformation, results in plants that are resistant to photosystem II herbicide and have normal electron transport.

In addition to the targeting segment and the DNA sequence encoding the selectable phenotype, vectors for stable transformation of plastid gene preferably comprise restriction sites for insertion of a passenger gene of interest. Insertion of the passenger gene into the plastid genome is readily obtained because the passenger gene is flanked by portions of the targeting segment (comprising homologous plastid DNA sequences), which direct the insertion of the passenger DNA into the plastid genome.

B. Preferred Methods of Transforming Plastids

Several methods are available to introduce DNA into the plastids of flowering plants, including, but not limited to, Agrobacterium vectors, polyethylene glycol (PEG) treatment of protoplasts, bombardment of cells or tissues with microprojectiles coated with the transforming DNA (sometimes referred to herein as "biolistic DNA delivery") and temporary holes cut by a UV laser microbeam. Other methods include use of geminivirus vectors, calcium phosphate treatment of protoplasts, electroporation of isolated protoplasts and agitation of cell suspensions with microbeads coated with the transforming DNA. The biolistic method is preferred for practice of the present invention because it can be used on a wide variety of plants and tissues therein, including species or genera not amenable to cell or protoplast culture or regeneration. In an alternative embodiment, useful in plant systems where protoplasts may be obtained and regenerated into intact plants, plastid transformation may be achieved by polyethylene glycol (PEG) treatment of protoplasts in the presence of the transforming DNA. Methods for stable plastid transformation in PEG-treated tobacco protoplasts, in accordance with methods of the present invention, are described by Golds et al., Bio/Technology, 11: 95–97 (January, 1993).

C. Obtaining Multicellular Plants Having Stably-Transformed Plastids

In accordance with the present invention, multicellular plants having stably-transformed plastids may be obtained by the following method:

(1) Provide a transforming DNA (preferably contained in a vector), which comprises a targeting segment in which is disposed a DNA sequence encoding a non-lethal selectable phenotype, as described above;

(2) Deliver the transforming DNA into the plastid, thereby enabling integration of the transforming DNA without interfering with the normal function of the plastid genome;

(3) Maintain the treated cells or tissues on the appropriate selection medium until homoplasmic cells or tissues are obtained; and (4) Identify homoplasmic cells and tissues by their expression of the selectable phenotype. The method further comprises growing the identified transformants to mature plants and testing their progeny for maintenance of the selectable phenotype.

In the preferred biolistic method of transformation, described in detail in Example 1, the organelle is hit by a DNA-coated tungsten particle carrying 20–50 copies of the vector containing the transforming DNA; however, the transforming DNA probably interacts with only one or, at most, a few of the many plastid genomes in the organelle. It has been determined that achieving the homoplasmic state of transgenomes takes at least 16 to 17 cell divisions, during which time between $5 \times 10^4$ and $10^5$ cells are obtained from the original transformed cell. Therefore, selection pressure is maintained throughout cellular proliferation to obtain a homoplasmic organelle and finally a homoplasmic cell. The use of a non-lethal selectable marker enables this cell division to occur, so that the selectable phenotype may be expressed.

II. Vectors for High Frequency Transformation of Plastids and Expression of Foreign Genes in Plastids As described hereinabove, stable transformation of plastid genomes is accomplished by a multistep process involving: (1) introduction of the transforming DNA, preferably on the surface of microscopic tungsten particles with the biolistic process, or by polyethylene glycol treatment of protoplasts; (2) integration of the transforming DNA into the plastid genome by homologous recombination events; and (3) selective elimination of wild-type plastid genome copies during the course of repeated cell divisions. Since plant cells may contain thousands of identical copies of the plastid genome, development of non-lethal selectable marker genes has been critical for the recovery of transplastomes in a pure population. Of great importance also has been the selection of suitable target sites for transformation of the plastid genome.

In the embodiments described in Section I above, the non-lethal selectable marker comprised resistance to spectinomycin, based on mutations in the 16S rRNA gene, which resulted in the expression of a 16S ribosomal RNA that is resistance to the effects of spectinomycin. Transformation frequencies utilizing constructs containing the mutant 16S rDNA were on the order of one plastid transformant recovered in about 100 bombarded samples, using the biolistic method. This frequency is lower by 2–3 orders of magnitude than biolistic transformation of nuclear genes, wherein one bombardment with DNA-coded microscopic tungsten particles yields 2–20 nuclear gene transformants.

In accordance with the present invention, it was discovered that transformation with a chimeric bacterial aadA gene encoding aminoglycoside 3"-adenyltransferase (which converts both spectinomycin and streptomycin to inactive forms) dramatically improves the recovery of plastid transformants, yielding frequencies typical of those for nuclear genes. The chimeric gene consisted of 5' and 3' plastid regulatory signals flanking the aadA coding region. It is believed that the increase in transformation frequency is due to an improved recovery of the newly formed transgenomes by the dominant aadA gene, as explained below.

The 100-fold lower transformation frequency observed with the use of the mutant 16S rDNA is likely due to the recessive nature of the mutant gene. (The assumption that the 16S rDNA is recessive is based on experiments with ribosomal RNA mutants in $E.$ $coli$ (Sigmund et al., Nucl. Acids. Res., 11: 4653–63, 1984; Montandon et al., EMBO J., 5: 3705–08, 1986; Melancon et al., Nucl. Acids. Res., 16: 9631–39, 1988) that are similar to the plastid mutants (Harris et al., Genetics, 123: 281–92, 1989; Svab et al., Mol. Gen. Genet., 228: 316–19, 1991).) The mutant 16S rDNA confers resistance to spectinomycin by encoding a plastid 16S ribosomal RNA that can function, at least to some extent, in the presence of spectinomycin concentrations used in the selection process. This mutant gene is recessive, in the sense that, if it is present in a plastid with copies of the plastid genome containing the wild-type sensitive gene, the phenotype expressed by that plastid will be sensitivity to spectinomycin. Lack of phenotypic resistance permits the loss of the resistant 16S rDNA in 99 of 100 potential transformation events. (Elimination of the transgene may occur by gene conversion, an active mechanism that keeps both copies of the ≈25-kb inverted repeated identical at the DNA sequence level (Harris et al., Genetics, 123: 281–92, 1989; Svab et al., Mol. Gen. Genet., 228: 316–19, 1991).) Thus, phenotypic resistance is delayed, not being expressed until sorting out of the transgenomes is essentially complete.

In contrast, the aadA gene encodes an adenyltransferase that converts both spectinomycin and streptomycin to inactive forms. This gene is dominant in that its expression in a plastid leads to the resistance phenotype, even if the plastid contains many copies of genomes that do not contain the gene. Consequently, the resistance phenotype is expressed much earlier during the sorting out process, and plastid genomes containing the gene are preferentially maintained.

The foregoing observations regarding the utility of selectable marker genes encoding compounds that inactivate the selective substance as a means to increase plastid transformation efficiency have been extended to include other such genes known in the art, such as: (1) the bacterial kan gene encoding neomycin phosphotransferase which confers resistance to kanamycin and related antibiotics; (2) the tn5 streptomycin resistance str gene encoding streptomycin phosphotransferase; and (3) the aacCl gene, conferring gentamycin resistance by encoding gentamycin acetyltransferase-3-I; and (4) the sull1 gene encoding dihydropteroate synthetase, conferring resistance to sulfonamides.

It has further been discovered in accordance with the present invention that the 5' and 3' plastid regulatory regions of such chimeric genes may be selected and manipulated to increase the efficiency and versatility of foreign gene expression in plastids. Moreover, target sites in the plastid genomes that are particularly advantageous for insertion of foreign gene have now been identified, as described in greater detail below.

In keeping with the foregoing discussion, this invention provides DNA constructs for high frequency stable transformation of plastids and expression of foreign genes therein. These DNA constructs are preferably provided in the form of vectors, which may be maintained and propagated in a suitable laboratory host, such as E. coli. Such a vector will comprise a targeting fragment of homologous plastid DNA sequences, into which a selectable marker gene, such as the chimeric aadA gene described above, is inserted. Transforming DNA comprising a selectable marker gene flanked by targeting segments is sometimes referred to herein as an "insertion vector."

Figure 1B:
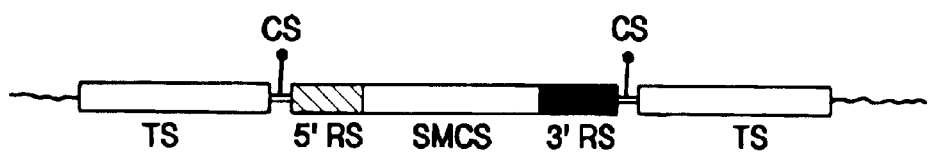

One type of insertion vector comprises a selectable marker coding segment, which encodes the non-lethal selectable marker (i.e., selectable phenotype) flanked by 5' and 3' plastid regulatory sequences. A schematic diagram of this type of insertion vector is shown in FIG. 1B. The selectable marker coding segment is flanked on the 5' side by a 5' regulatory segment, and on the 3' side by a 3' regulatory segment. The 5' and 3' regulatory segments regulate the expression of the selectable marker coding segment in plastids. The expression cassette is itself flanked on both sides by portions of the targeting segment.

Figure 5:
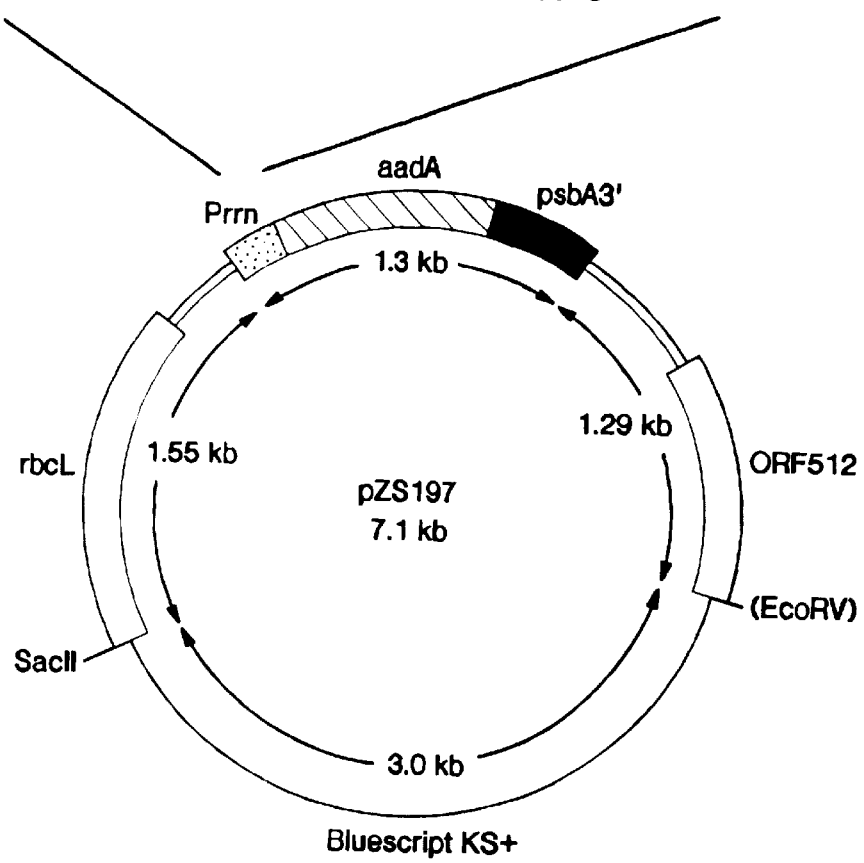
FIG. 5—Diagram of the pZS197 transformation vector. The chimeric aada gene was cloned into a Sac II/EcoRV ptDNA fragment between the rbcL and ORF512 genes (coding regions are boxed) in the 3-kb pBluescript vector (thin line). In the chimeric gene, expression of the aada coding region is controlled by a modified plastid ribosomal RNA operon promoter, Prrn, and the 3' region of the plastid psbA gene (psbA3'). The sequence of Prrn (Sequence I.D. No. 1, shown above the diagram) includes sequences of the plastid ribosomal RNA operon promoter (nucleotides 1–117; Sun et al., Mol. Cell Biol. 9: 5650–59). G at position 1 corresponds to nucleotide 102,561 of the tobacco plastid genome in ref. 11. Mutations generated to eliminate upstream AUGs in the mRNA are in lowercase letters. A synthetic leader sequence (nucleotides 118–135), including a ribosome binding site (RBS), are in lowercase letters. The cpt1 and cpt2 regulatory sequences are underlined. ATG at nucleotide 136 (boldface letters) is the aadA translational initiation codon. Fragment sizes are shown inside the map.

One example of a vector of the present invention is shown in FIG. 5, which depicts plastid transformation vector pZS197. Construction of pZS197 is described in detail in Example 2.

In a preferred embodiment, the plastid transformation vector exemplified by pZS197 is modified by including cloning sites (or a multiple cloning site) for insertion of passenger genes of interest, including a reporter gene, and other useful passenger genes (see FIG. 1B). The vector may be further modified to advantage by adapting the insertion vector, and components thereof, for convenient manipulation in a cloning vector, and by utilizing targeting fragments for different regions of the plastid chromosome. Each of these features and modifications of constructs of the invention are described in greater detail in Section A–E below.

A. Cloning Vector

The transforming DNA (i.e., selectable marker gene flanked by targeting segments) is preferably maintained in any convenient cloning vector, for purposes of amplification and manipulation of the DNA. Such vectors are well known in the art, and are commonly available. In a preferred embodiment, the cloning vector will be of a type that is amenable to site-directed mutagenesis, such as the pUC plasmids (e.g., pUC 118–119) or the pBluescript phagemid vectors (Stratagene).

B. Targeting Segment

As mentioned, all characterized recombination events in plastids have been between homologous sequences. Targeted insertion of foreign genes into the plastid genome is thus obtained by flanking the heterologous sequence with homologous plastid DNA segments. This homologous plastid DNA is referred to as a targeting segment (or targeting fragment) because it directs the insertion of the foreign DNA to a particular location in the plastid genome.

Desirable characteristics of a plastid targeting segment are: (1) sufficient flanking plastid DNA sequence for efficient targeting of heterologous DNA; (2) a carefully chosen insertion site so that the integrated heterologous DNA does not interfere with the expressions of the adjacent plastid genes; and (3) the availability of convenient restriction sites for insertion of the heterologous DNA, i.e., the expression cassette.

The targeting segment should be sufficiently large to ensure homologous recombination between the transforming DNA and the plastid genome. To accomplish this, the targeting segment should be at least about 50 bases long, and preferably between 500 and 1500 bases on each side of the expression cassette or other DNA to be inserted into the plastid genome. A targeting segment of 1.2–1.5 kb on each side of the expression cassette has been found sufficient for insertion of a heterologous sequence of 5 kb.

At the most basic level, a targeting segment should be selected such that the transforming DNA does not disrupt the expression of adjacent plastid genes. Useful targeting segments may be easily identified by one skilled in the art, due to the availability of extensive genome mapping information and sequence information for several plastid genomes (see Background section), combined with applicability of this information to other plastid genomes as a result of the high degree of conservation among plastid genomes (Palmer, Trends in Genetics, 6: 115–120, 1990; Sugiura, Plant Mol. Biol., 19: 149–168, 1992). In a preferred embodiment of the present invention, a targeting segment is selected that targets foreign genes at a BamHI (tobacco plastid genome position 59,286) between the rbcL and accD (formerly ORF512) gene in the large single copy region of plastid DNA. This site is described in detail in Examples 1–3. Stable integration of an expression cassette has also been obtained in the large single copy region between the psbE and peta operon at an EcoRV site (position 66,043 in the tobacco chloroplast genome), between the trnG and trnfM genes at a SpeI site (position 38,302 of the tobacco chloroplast genome) and between the psbA and trnH genes at a BspHI site (position 344 of the tobacco plastid genome).

In another preferred embodiment, targeting segments are selected which direct insertion of foreign genes in the inverted repeat region of the plastid genome. An attractive feature of targeting transgenes into the repeated regions is their automatic duplication by the highly efficient gene conversion/copy correction mechanisms operating in plastids (see Examples 1, 2 and 6). Such duplication is advantageous if high levels of expression are desired. One example of a suitable site for insertion of foreign genes in the inverted repeat region is between the trnV and 16S rDNA genes. Stable insertion of a 2.5 kb chimeric gene expressing the uidA coding region (encoding β-glucuronidase) is set forth in Example 5.

Another example of a suitable insertion site in the inverted repeat region is between the trnV gene and the adjacent operon on the other side, rps7/12. Insertion of an expression cassette containing the aadA coding region into this site is described in Example 6.

Given that the 3' regions of plastid genes terminate transcription inefficiently (Gruissem & Tonkyn, Critical Review in Plant Sciences, 12: 19–55, 1993), some degree of read-through transcription might be expected when inserting the transforming DNA at almost any location in the plastid genome. The aforementioned trnV-rps7/12 insertion site is particularly useful in view of this fact, because the transforming DNA is transcribed without detectable read-through transcription when oriented toward the rps12/7 operon (see Example 6). This lack of read-through transcription in the trnV12/7 insertion site is likely due to the fact that the respective genes or operons are divergently transcribed (i.e., transcribed on opposing strands, in opposite directions).

Hence, targeting segments directed to sites between other divergently transcribed genes will also be useful in the practice of the present invention. These include, but are not limited to, sites between trnL and ORF2280 in the inverted repeat region, and between trnS and ORF168 and trnW and petG in the large single-copy region. Alternatively, insertion sites between any two tRNA genes may also be useful, since tRNA genes are relatively efficient terminators of transcription (Stern & Gruissem, Cell, 51: 1145–57, 1987). The same result may also be achieved by flanking the insertion sites with transcription terminators which can be synthesized or excised from source genes and cloned.

C. Expression Cassette

The selectable marker gene and/or other passenger genes of interest are provided in expression cassettes for insertion into the targeting segment. An expression cassette, as used herein, comprises 5' and 3' regulatory segments, preferably adapted for convenient mixing and matching by standard recombinant DNA techniques. Expression cassettes may be maintained in cloning vectors as pairs of 5' and 3' regulatory segments, connected by way of one or more restriction sites into which a coding segment may be inserted. Alternatively, the 5' and 3' regulatory segments may be separated by a "stuffer" fragment or protein-coding segment, which may be removed and replaced with a coding segment.

An expression cassette containing a coding segment whose expression is controlled by the 5' and 3' regulatory segments is, by common definition, a chimeric gene, and is sometimes referred to herein as such. The use of expression cassettes to produce chimeric genes for insertion into a transforming DNA is a preferred embodiment of the present invention. A transforming DNA may contain only one such chimeric gene, or two or more chimeric genes may be inserted into the targeting segment of the transforming DNA. In one embodiment, one expression cassette may direct constitutive expression of its coding segment, while another expression cassette may direct tissue-specific or inducible expression of its coding segment, as described in greater detail below. Alternatively, the DNA introduced in the targeting segment may contain more than one coding region controlled by the same 5' regulatory segment for expression of multiple genes, similar to a procaryotic or plastid operon. In this case, a polycistronic mRNA is produced, which is thereafter translated into multiple gene products (see Example 7).

The coding segment of the expression cassette should comprise a single open reading frame, uninterrupted by nuclear introns, since splicing of nuclear introns is not part of the plastid transcription/translation machinery. Hence, coding regions may be taken from bacterial genes or from cDNAs of nuclear genes, both of which comprise intron-less open reading frames.

To practice the invention, the transforming DNA contains at least one gene which confers a non-lethal selectable phenotype. The selectable marker gene may be provided in the form of a selectable marker coding segment in an expression cassette, thereby forming a chimeric selectable marker gene. In a preferred embodiment, the selectable marker coding segment is of a dominant type (as defined hereinabove), such as a coding region encoding a gene product that inactivates the antibiotic or other substance used as the selection means. In a particularly preferred embodiment, the aadA coding region is used as the selectable marker coding segment in an expression cassette. Although this embodiment has been exemplified, any dominant-type coding region is contemplated to be useful in practicing the present invention, as described above. In addition to the use of dominant-type genes as the source of the selectable marker coding segment, recessive-type genes may also be used to advantage.

The targeting segment containing the chimeric selectable marker gene may also contain a coding segment for a passenger gene of interest under control of the same 5' regulatory segment, as described above. Alternatively, a separate expression cassette containing one or more passenger genes of interest may be inserted into the transforming DNA, as described above. A discussion of a useful passenger genes is set forth in Section III below. One type of passenger gene that is particularly useful in the constructs of the invention is a gene that encodes a detectable gene product, which can serve as a measure of expression of foreign DNA in transformed plastids. Such genes are sometimes referred to herein as "reporter genes," and their coding regions as "reporter coding segments." A preferred reporter coding segment for use in the present invention is the coding region of the uidA gene, encoding β-glucuronidase (GUS), which is detectable by a well-known color-based enzymatic assay (see Examples 5 and 7). The uidA gene is commonly available commercially (e.g., Clontech Laboratories, Inc., Palo Alto, Calif.). In an alternative embodiment, the expression marker coding region is taken from the bacterial kan or neo genes, which encodes neomycin phosphotransferase (NPTII). NPTII is commonly detected by immunological means; the protein and its antibodies are widely available, as are the coding regions of the kan gene or the neo gene (e.g., Clontech Laboratories, Inc.). Another useful reporter coding segment is the coding region for luciferase, an enzyme whose activity is detectable by a fluorescince-based assay. This coding region is also available (e.g., Promega Biotech, Madison, Wis.). Other similarly useful expression marker coding segments will be apparent to one of skill in the art. These coding regions should express proteins that are stable and detectable by some means.

D. 5' and 3' Regulatory Segments

Expression cassettes comprise 5' and 3' regulatory segments to control expression of the coding segment. The 5' regulatory segment controls the amount of expression, as well as the specificity (i.e., constitutive versus tissue-specific) and inducibility (e.g., light-inducibility) of expression. The 3' regulatory segment confers mRNA stability. The 5' and 3' regulatory segments are derivable from 5' and 3' regulatory regions of endogenous plastid genes, which may be further modified. The 5' and 3' regulatory regions may be from the same plastid gene or from different plastid genes. Moreover, sequences from different plastid genes may be incorporated within a 5' or 3' regulatory segment. Although regulatory elements of endogenous plastid genes are likely the most useful source of 5' and 3' regulatory segments of the invention, other 5' and 3' regulatory regions are also contemplated for use in the present invention; particularly such regions taken from *E. coli*, cyanobacteria, photosynthetic bacteria, bacteriophages and plant viruses. Due to the procaryotic nature of plastids, regulatory regions from genes of those organisms will likely be functional in the plastid genome.

The 5' regulatory segment should comprise a strong promoter of plastid gene expression. Such promoters include the 16S ribosomal RNA operon promoter and promoters of the photosynthetic gene rbcL and psbA, as well as LRP, the strong, light-regulated promoter of the psbD operon (Example 7). As described in Examples 5 and 7, the photosynthetic gene/operon promoters direct expression of foreign proteins only in photosynthetic tissue, and in a light-inducible manner. Therefore, these and other promoters of photosynthetic genes or operons are particularly preferred for high-level expression of foreign protein in leaves, particularly if the ability to be able to control such expression by providing or removing light is a desirable feature. A photosynthetic tissue-specific light-inducible promoter will be particularly useful for expressing extra quantities of a photosynthetic protein that may be especially subject to photodegradation. Thus, for example, resistance could be increased by overexpressing a protein to protect plastids from photooxidative damage. Genes encoding oxygen-scavenging enzyme (e.g., peroxidase, superoxidase dismutase, etc.) could be placed in the transforming DNA under control of a photosynthetic promoter-containing 5' regulatory segment. This would result in the overexpression of such enzyme in photosynthetic tissue in the light, when photooxidative damage occurs.

In addition to having promoter elements for directing transcription, 5' regulatory segments may contain additional expression-promoting elements for regulating translation, such as ribosome binding sites contained in 5' untranslated regions (UTRs) of plastid genes, as well as sequences encoding a few of the N-terminal amino acids of the plastid gene. The utility of such elements is described in the context of a constitutive promoter, Prrn, hereinbelow.

To obtain high levels of protein expression in plastids of non-photosynthetic tissue, expression of transgenes from constitutive non-photosynthetic promoters should be utilized in the expression cassettes. As mentioned above, a strong promoter of this class is the 16S ribosomal RNA operon promoter, Prrn. The mRNA from the rrn operon accumulates to higher levels in both leaves and roots than the mRNA for any other non-photosynthetic plastid gene, making this promoter an ideal candidate for constitutive expression cassettes. However, since the transcript of the rrn operon is not translated (the product is ribosomal RNA), expression of proteins from this promoter requires the addition of translation control signals directing translation of the mRNA encoded by the coding segment of the expression cassette. Translation-directed signals should include a ribosome binding site (RBS) and an in-frame translational start codon (e.g., ATG).

An example of a rrn operon promoter than has been engineered for expression of the spectinomycin resistance gene, aadA, is set forth in Example 2 (see FIG. 6). This 5' regulatory segment contains a segment of the rrn operon 5'-region, including the −10 and −35 promoter elements, fused with 18 nucleotides of the highly-expressed rbcL untranslated region, which includes the GGGUGGG ribosome binding site. As described in detail in Example 7, this 5' regulatory segment was capable of directing constitutive expression of the uidA gene in transformed plastids. The Prrn(L)rbcL(S) and Prrn(S)psbA(S) 5' regulatory segments described in Example 3 were also capable of directing expression of the kan gene in roots.

It was also discovered that this expression could be improved by including the entire rbcL leader sequence from −16 to +18 relative to the translation start site. Expression was even further improved by substituting the rbcL leader sequence with a 5' UTR from the psbA gene. Thus, the promoter and 5' UTR may be modified and substituted in order to optimize expression of foreign proteins in plastids, or to confer tissue specificity or light-inducibility. Given the importance of mRNA leader sequences (i.e., 5' UTRs and N-terminal coding regions) for high level protein expressions, other useful leader sequences may be derived from other highly expressed genes, particularly highly expressed viral genes (e.g., the omega sequence of tobacco mosaic virus (TMV) coat protein, or untranslated leaders from alfalfa mosaic virus (AMV) RNA4 or brome mosiac virus (BMV) RNA3).

The expression cassettes of the invention also comprise a 3' regulatory segment. These 3' regulatory segments are preferably derived from the 3' regions of plastid genes, and serve to stabilize plastid mRNAs. It will be appreciated by those skilled in the art that such 3' regulatory segments may also be obtained from other sources, such as genes of bacteria, cyanobacteria or viruses.

Examples of 3' regulatory segments suitable for practice of the present invention are set forth in the Examples, particularly Examples 4 and 7. These segments are derived from the 3' untranslated regions of various plastid genes. In contrast to the variation observed in expression directed by different 5' regulatory segments, it has been found that only relatively small variation results from substituting one 3' regulatory segment for another (see Example 7). Accordingly, any 3' untranslated region of a plastid gene should be useful in the expression cassettes of the invention, including, but not limited to: psbA 3', rps16 3' and rbcL 3'.

E. Examples of High Frequency Transformation/Expression Vectors

The pPRV Family

In sum, a transforming DNA construct of the present invention is prepared as follows:

(1) Select an insertion site on the plastid genome to be transformed;

(2) From the plastid genome, excise and clone into an appropriate vector a targeting segment containing the selected insertion site flanked on either side by a sufficient length of homologous plastid DNA to ensure homologous recombination;

(3) Modify the target site, if necessary, for insertion of a foreign DNA (i.e., create a restriction site);

(4) Prepare foreign DNA in a vector plasmid as follows:
   (a) assemble appropriate 5' promoters and 5' UTRs into a 5' regulatory segment;
   (b) select a 3' regulatory segment;
   (c) select coding segments, including a selectable marker coding segment, an expression marker coding segment and/or coding segments for passenger genes of interest;
   (d) assemble foreign DNA to be inserted using recombinant DNA methods;

(5) Insert foreign DNA into targeting segment; and (6) Amplify the DNA.

A general example of a vector comprising a transforming DNA made according to the above procedure is shown in FIG. 1B. Specific examples of vectors useful for inserting foreign genes into the inverted repeat region of the plastid genome are set forth in Example 7 as the pPRV series of plastid transformation vectors.

III. Uses of DNA Constructs and Methods for Stable Plastid Transformation and Expression of Proteins in Plastids The DNA constructs and methods for stably transforming plastics and expressing recombinant proteins in plastid will find wide utility for plant improvement. These plastid transformation methods and constructs will complement the currently available and developing technologies for transformation of the plant nuclear genome.

A. Gene Replacement, Deletion, Relocation

The method and constructs of the present invention may be used to advantage to replace genes already present in the plastid genome. The utility of replacing genes on the plastid genome has been discussed above in the context of resistance to the triazine herbicide, which act by photodegrading the product of the plastid psbA gene, which is required for photosynthetic electron transport. Mutants of psbA, whose gene products are more tolerant or resistant to the effects of the triazine herbicide, have been identified. Using the constructs and methods of the present invention, such resistant genes may be introduced to plastids and targeted to replace a sensitive psbA gene.

The methods and constructs of the invention may be used similarly to replace any plastid gene with an improved form of the same gene, either from the same plant species or from a different plant species. For example, the Rubisco large subunits (LSU, encoded by the plastid rbcL gene) from wheat or sunflower are believed to produce particularly efficient forms of Rubisco. Productivity of selected plant species may be improved by substituting wheat or sunflower rbcL for the endogenous rbcL. An example of gene replacement using the methods of the invention is set forth in Example 1.

The DNA constructs and methods of the invention may also be used to delete a gene from the plastid genome, e.g., for the purpose of moving a gene function to the cytoplasm by concomitant addition of the plastid gene to the nuclear genome. This is accomplished by disrupting the plastid gene, e.g., by targeted insertion of a heterologous DNA segment in a coding or regulatory region of the plastid gene. The use of the constructs and method of the invention for deletion/relocation of a plastid gene is set forth in Example 5.

B. Gene Insertion/Expression of Recombinant Proteins

By far the most useful aspect of the constructs and methods of the invention is the introduction and expression of foreign genes in plastids, where the introduced DNA could be additional plastid DNA, or nuclear genes from plants, or even heterologous DNA from other sources (e.g., bacteria, fungi, animals, etc.). The transformed plastids could be used to express heterologous protein in large quantities for harvesting, a utility that is particularly applicable to plastid-containing plant cells that can be grown in culture. Using such a system, proteins of agronomic, medical or industrial importance could be produced in quantity. These proteins could be toxins that kill plant pests, therapeutic proteins such as insulin, or enzymes used in industrial processes. Expression of proteins in storage organs, such as potato tubers or sugar beet roots would also be effective for producing proteins on an industrial scale, or for producing other industrial products (e.g., polyhydroxybutyrate, a biodegradable thermoplastic) in a storable form (see Example 7).

Insertion and expression of foreign DNAs in plastids can also be used to great advantage to improve the plant whose plastids have been transformed. Examples of some foreign DNA that could be usefully inserted into a plant plastid genome include DNA encoding: herbicide resistance, nitrogen fixing ability, increased photosynthetic capacity, drought resistance, salt tolerance, tolerance of temperature extremes, resistance to plant diseases and resistance to plant pests, such as insects, nematodes and protozoans. Regarding nitrogen fixation, the constructs and methods of the invention could be used to convert plastids into "nitroplasts" (plastids capable of nitrogen fixation) by incorporating the relevant bacterial genes into the plastid genome. Such plastids could carry out photosynthesis during the day and fix nitrogen during the night, using the accumulated carbohydrates as the energy source. This system would duplicate the process by which certain unicellular cyanobacteria carry out oxygen-evolving photosynthesis and oxygen-labile nitrogen fixation within the same organism.

As another example, the plastids of flowering plants are the sites of biochemical pathways, such as starch biosynthesis and synthesis of amino acids and lipids. These biochemical pathways are encoded exclusively by nuclear genes. Incorporating such genes into plastids may improve the efficiency and productivity of these biochemical pathways.

Expression of plant nuclear genes in plastids may prove especially useful in engineering herbicide resistance. For example, the plastid could be used for overproduction of an herbicide target enzyme, such as resistance to glyphosate by overproduction of 5-enolpyruvylshikimate-3-phosphate synthase (pEPSPS), which is encoded in the plant nucleus. Another example, which was described above, is replacement of a sensitive form of target protein with a form that is less sensitive to an herbicide (e.g., resistance to sulfonylurea (chlorsulfuron) and imidazolinone by overexpression of a resistant nuclear-encoded enzyme, acetolactate synthase (ALS). As yet another example, resistance to the herbicides "Basta" and "Bialaphos" may be obtained by expressing the nuclear bar gene (encoding phosphinotricin acetyltransferase) in plastids. Transferring nuclear-encoded resistance to the plastid has the added advantage of preventing pollen transmission of herbicide resistance to volunteer plants or weeds.

The foregoing paragraphs set forth but a few of the numerous applications of the DNA constructs and methods of the invention for introducing and expressing foreign genes in plastids. In light of the general discussion above and the specific examples (e.g., examples 2–7) of foreign gene expression set forth herein, many other application will occur to one of skill in the art.

C. Applicability of Constructs and Method of the Invention Through Non-Photosynthetic Plastids and to Diverse Plant Species This invention has been described and exemplified with respect to transformation of photosynthetic plastids, i.e. chloroplasts. However, plants contain other types of plastids (e.g., chromoplasts, amyloplasts), which are equally amenable to transformation using the constructs and methods set forth herein.

The methods and DNA constructs of the present invention may be applied to chromoplasts without any modification whatsoever. If chromoplast-containing cells are maintained in culture, resistant cells can be identified by whatever pigment color the particular chromoplasts accumulates. Chromoplasts usually contain carotenoid pigments, which are yellow or orange.

Amyloplasts are starch-accumulating organelles that are not pigmented. Moreover, both amyloplasts and chromoplasts may de-differentiate to proplastids (nonpigmented) in culture. The non-lethal selection method of the invention may still be applied to amyloplasts or proplastids simply by adding a detectable reporter gene to the transforming DNA, along with the selectable marker gene. For example, the transforming DNA may contain an expression cassette for aadA and another expression cassette for uidA, encoding the easily detectable GUS. Cells expressing the selectable resistance phenotype will also express GUS and will stain blue upon treatment with the appropriate color-indicating reagent. The gene encoding luciferase may also be used for this purpose, using a fluorescence-based detection system. Alternatively, the resistance phenotype may be apparent in amyloplast-containing tissue, either visually (i.e., tissues may appear different because they are not accumulating starch) or by using simple chemical identification means for the presence or absence or starch. Other adaptations of the method and constructs of the invention to non-pigmented plastids will be apparent to one of skill in the art.

Plastid genomes show a high degree of conservation, even among the most diverse plants species. For this reason, the method and DNA constructs of the invention may be used in any plant species, with a minimum of adaptation or modification. Because of the variety of ways in which foreign DNA can be introduced into plastids, the major limiting factor to applying the constructs and method of the invention to different species will be the amenability of those species to tissue culture and somatic regeneration of intact plants. This technology is being expanded at an ever-increasing pace, as demonstrated by the rapid advancements made over the last decade in culture and regeneration of important crop plants of the grass family (e.g., maize, sorghum, rice, wheat), species which had been recalcitrant to tissue culture for many years. Accordingly, as this technology expands to encompass new plant species, the plastid transformation method and constructs of the invention can be used on those new species. Once a transforming DNA has been introduced to the highly conserved plastid, the principles underlying the present invention will apply regardless of species-to-species variations.

Thus, the method and DNA constructs of the invention may be widely applied for improvement of crop plants (dicotyledonous or monocotyledonous) or plants having horticultural or environmental value.

The following examples are provided to describe the invention in further detail. These examples are intended to illustrate and not to limit the invention.

EXAMPLE 1

Stable Genetic Transformation of the Plastid Genome in *Nicotiana tabacum* by Selection for 16S rDNA-Encoded Antibiotic Resistance This Example is published as Svab et al., Proc. Natl. Acad. Sci. USA 87: 8526–30 (November 1990).

Materials and Methods

Plant Lines

Two recipient lines were uses. *N. tabacum* cv. Petit havana with its original cytoplasm, Nt(tbc), and the Nt(pbg) alloplasmic substitution line that has the nucleus of *Nicotiana tabacum*, and the cytoplasm of *Nicotiana plumbagnifolia*. The Nt(pbg) line is functionally male sterile because the filaments are shortened. Seeds, however, can be obtained by manual pollination. The Nt(pbg) line was obtained from Dr. Kevin Vaughn, USDA Delta States Research Center, Stoneville, Miss.

The *N. tabacum* SPC2 line has the original *N. tabacum* cytoplasm, and is a derivative of the SR1 mutant (Maliga et al., Nature (London), New Biol., 244: 29–30, 1973). SPC2 cells exhibit a high level of resistance to both streptomycin and spectinomycin. The two mutations are tightly linked (278 bp apart) and are due to a C to A change at position 860 (Etzold et al., FEBS Lett., 219: 343–46, 1987), and a C to U change at position 1139 (Svab and Maliga, unpublished) in the 16S rDNA.

Transformation and Regeneration of Transgenic Plants

For bombardment of leaf tissue, plants were aseptically grown from seed on Mirashige & Skoog (MS) medium. The MS medium is agar supplemented with MS salts (Murashige and Skoog, Physiol. Plant., 15: 473–97, 1962) and sucrose (30 g/liter). Leaves were planted with abaxial side up on RMOP medium in a Petri dish. The RMOP medium consists of MS salts, $N^6$-benzyladenine (1 mg/liter), 1-napthaleneacetic acid (0.1 mg/liter), thiamine (1 mg/liter), inositol (100 mg/liter), agar (6 g/liter) at pH 5.8, and sucrose (30 g/liter).

Tungsten (1 μm) was prepared for transformation by mixing 25 μl of suspension (25 mg tungsten in 500 μl of $H_2O$) with 4 μg DNA dissolved in 5 μl $T_{10}E_1$ buffer (10 mM Tris-HCl, pH 8, 1 mM EDTA), 10 μl 2.5 M $CaCl_2$ and 0.1 M spermidine base. The particle-DNA mixture was incubated on ice for 2 min. and centrifuged for 1 min. in an Eppendorf centrifuge. After removing 25 μl of the supernatant, the tungsten was suspended by a brief (1 sec.) sonication, and applied to the microprojectiles (2.5 μl per bombardment). The bombardment was performed as described by Klein et al., Bio/Technology, 6: 559–63 (1988).

Two days after bombardment, the leaves were cut into sections (5 mm×5 mm) and transferred to RMOP medium containing 500 μg/ml of spectinomycin dihydrochloride. Green calli and shoots that formed on the bleached leaves were transferred onto the same selective medium. Shoots formed after a second selection on spectinomytin were rooted on MS medium to obtain plants. Cell culture procedures have been described in detail by P. Maliga, pp. 552–562 in *Cell Culture and Somatic Cell Genetics of Plants*, Vol. I, I. K. Vasil, ed., Academic Press, Orlando (1984).

Leaf and Seedling Assays to Test Resistance Phenotypes

Leaf sections of the regenerated plants were placed on a selective RMOP medium. Spectinomycin dihydrochloride (500 μg/ml) or streptomycin sulfate (500 μg/ml) will prevent greening of sensitive leaf callus on RMOP medium. Resistance phenotype of seedlings was determined by germinating surface-sterilized seeds on MS salts containing 3% sucrose (Maliga, 1984, supra). The antibiotics were filter sterilized, and added to the medium after autoclaving in the same concentration as for the leaf assay.

DNA Manipulations

All DNA manipulations were performed as described by Maniatis et al. (Maniatis et al., 1982; new edition is Sambrook et al., supra). Cloning was carried out in the pBluescript I KS+ phagemid vector (Stratagene). Plastid DNA was prepared according to Kolodner and Tewari, Biochem. Biophys. Acta, 402: 372–90 (1975). Designation and position of plastid genes is according to Shinozaki et al., EMBO J., 5: 2043–49 (1986). Total cellular DNA was prepared by the method of Fluhr et al., Theor. App. Genet., 67: 491–97 (1984). DNA for Southern probing was labelled using a random primed DNA labelling kit (Boehringer Mannheim).

Results

Construction of the pZS148 Plastid Transformation Vector

Plastid transformation vector pZS148 (FIG. 2) is derived from a pUC based plasmid (Vieira and Messing, Gene 19: 259–68, 1982) and carries the 16S rRNA gene cloned as a 3.7 kb SacI-EcoRV fragment from the SPC2 plastid DNA (ptDNA). The SPC2 line is resistant to streptomycin and to spectinomycin due to mutations in the 16S rDNA. An additional marker, a novel Pst I site, was generated 520 bp 3' to the spectinomycin resistance mutation, in the spacer region between the 16S rDNA and trnI genes, by inserting the synthetic oligonucleotide 5'-pd[GCTGCAGC]-3' into a StyI site. In addition, plasmid pZS148 carries the 2.9 kb SalI fragment, one of the regions implicated in plastid DNA replication (Carillo & Bogorad, Nucl. Acids Res., 11: 5603–20, 1988). Plasmid pZS134 is identical to pZS148 except that it carries the 16S rDNA from the SR1 line that is sensitive to spectinomycin.

TABLE 1

Selection of Plastid Transformants in Leaf Culture

| Transformants, DNA | Line | Bombarded leaves, no. | Spectinomycin-resistant clones, no. | Plastid no. |
|---|---|---|---|---|
| PZS134 | Nt(pbg) | 39 | 5 | 0 |
|  | Nt(tbc) | 11 | 1 | 0 |
| PZS148 | Nt(pbg) | 58 | 26 | 2 |
|  | Nt(tbc) | 90 | 30 | 1 |

Spectinomycin Resistant Clones After Transformation With pZS148 DNA

Whole leaves of Nt(tbc) and Nt(pbg) plants were bombarded with tungsten particles coated with pZS148 DNA according to the protocol of Klein et al., supra). In a sample of 148 bombarded leaves, 56 spectinomycin resistant lines were obtained (Table 1). Different plants regenerated from the same resistant line are considered subclones and are designated by a capital letter. For example, plants Nt(pbg*)T2B and Nt(pbg*)T2D derive from the same clone, Nt(pbg*)T2.

In order to test the frequency of spontaneous spectinomycin resistant mutants, leaf tissue was bombarded with pZS134 DNA, and cultured on a drug containing medium, as described for the pZS148 DNA. In a sample of 50 bombarded leaves, 6 spectinomycin resistant clones were recovered (Table 1). None of these clones were resistant to streptomycin (data not shown).

Spectinomycin resistance of the clones may be the result of transformation by the pZS148 DNA, or spontaneous mutation. The regenerated plants were therefore screened for the flanking unselected markers, the PstI site and streptomycin resistance.

TABLE 2

Flanking Markers in Plastic Transformants

| Line | Subclone | Resistance To Sp500 | Resistance To Sm500 | Pst I marker |
|---|---|---|---|---|
| Nt(pbg*)T2 | B | + | + | + |
|  | D | + | + | + |
| Nt(pbg*)T13 | A | + | − | + |
|  | B | + | − | + |
|  | C | + | − | + |
|  | M | + | + | + |
|  | P | + | + | + |
| Nt(tbc*)T85 | A | + | + | +,− |
|  | A1 | + | + | + |
|  | A2 | + | + | − |
|  | A3 | + | + | + |
|  | B | + | + | + |
|  | D | + | + | + |

Sp500, 500 μg of spectinomycin dihydrochloride per ml; Sm500, 500 μg of streptomycin sulfate per ml.

The Unselected PstI Marker in the Spectinomycin Resistant Lines

Figure 3A:
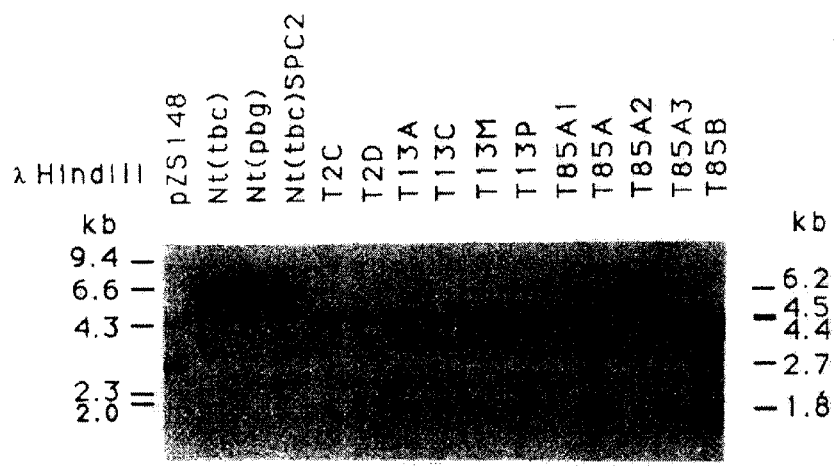
FIGS. 3A–3C—Southern probing to screen for the PstI marker. Results of probing total cellular DNA from leaves of regenerated plants grown in sterile culture (FIG. 3A) and isolated ptDNA from greenhouse plants (FIG. 3B) are shown after digestion with PstI and HindIII restriction endonucleases. As a control, pZS148 plasmid DNA and DNA of the NT(tbc), Nt(pbg) and Nt(tbc) SPC2 lines were included.

The spectinomycin resistant clones were screened for the PstI marker by Southern probing of total cellular DNA digested with HindIII and PstI restriction endonucleases (FIG. 3A). In wild type Nt(tbc) or Nt(pbg) DNA the probe hybridzed to a 6.2 kb fragment. Replacement of the 16S rDNA region with the engineered SPC2 clone introduces a PstI site into this 6.2 kb fragment, which results in the generation of a 4.4 kb and a 1.8 kb fragments. Based on the PstI marker, three transplastgenic clones have been identified (Table 2).

Figure 3B:
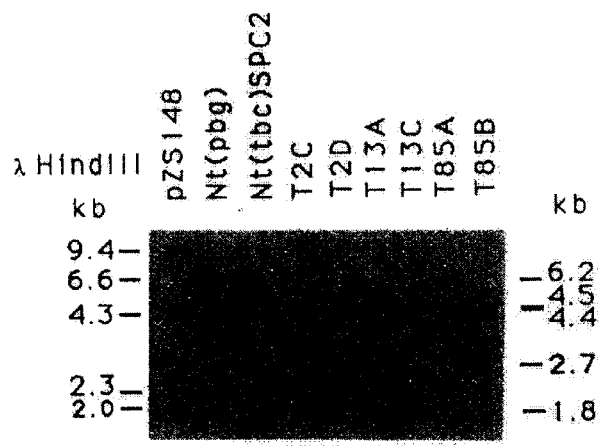
Figure 3C:
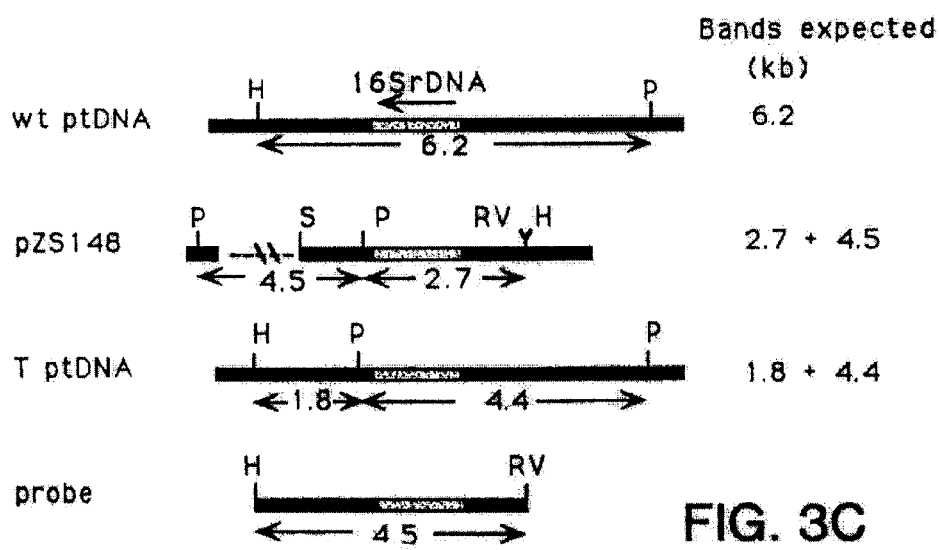

Plants regenerated from the transplastgenic clones contained the PstI marker (FIG. 3). In all but one, Nt(tbc*)T85A, there was no detectable amount of wild type fragment (FIG. 3). This indicates that the PstI site was present in both rDNA repeats, and the wild-type fragment has been eliminated. In a leaf of one of the plants, Nt(tbc*)T85A, a mix of wild-type and engineered 16SrDNA was found. Plants regenerated from the leaf of this plant carry a pure population of plastids with (85A1, 85A3) or without (85A2) the PstI marker. The plant without the PstI marker is also resistant to both antibiotics (Table 2).

Figure 4A:
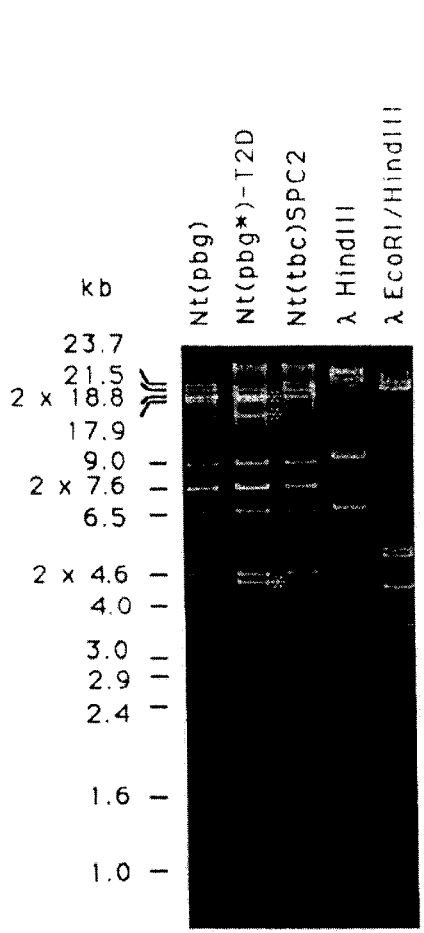
FIGS. 4A–4B—Copy-corrected Nt(pbg*)T2D ptDNA for the region containing the PstI linker.
Figure 4B:
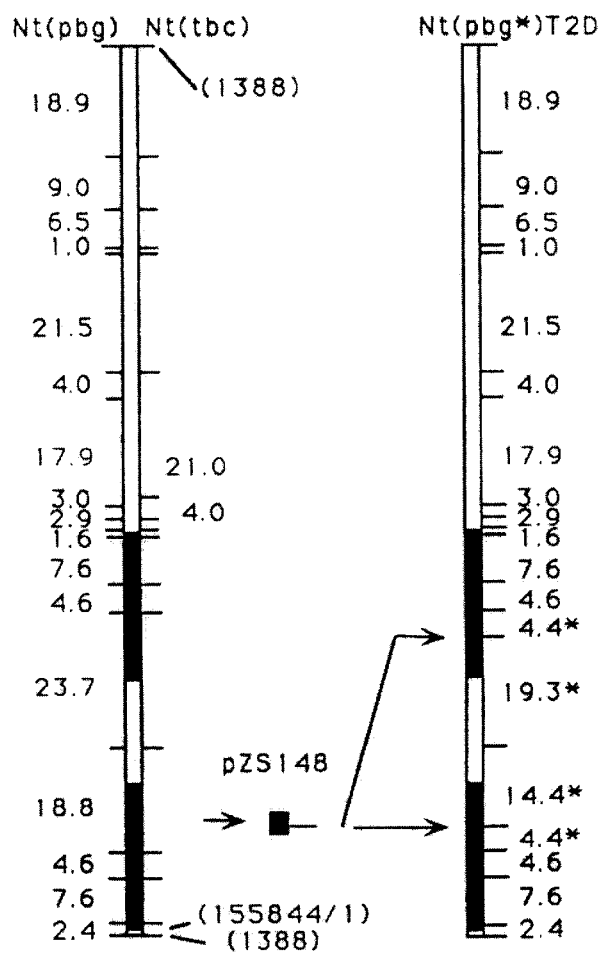

Plastid DNA was isolated from greenhouse grown plants approximately three months after the initial screen. PtDNA was probed as described above for total cellular DNA and was found to carry exclusively the PstI marker (FIG. 3B). Inspection of ethidium bromide stained PstI ptDNA fragments also indicated the absence of 23.7 kb and 18.8 kb wild-type PstI fragments. Instead, novel 4.4 kb, 14.4 kb, and 19.3 kb fragments were found (FIG. 4).

Probing for the novel PstI site in the 16S rDNA region is suitable to reveal a replicating pZS148 plasmid. If a replicating pZS148 plasmid is present, hybridization to 4.5 kb, 2.7 kb and 2.4 kb fragments is expected (FIGS. 2 and 3) in addition to hybridization to the 4.4 kb and 1.8 kb fragments derived from the integrated 16S rDNA copy (FIGS. 3 and 4). Fragments characteristic of intact pZS148 plasmids were absent in all samples tested by Southern probing (FIG. 3) or in ethidium bromide stained gels (FIG. 4).

The Unselected Streptomycin Resistance Marker in the Spectinomycin Resistant Lines The spectinomycin resistant clones were also tested for the unselected antibiotic resistance marker, streptomycin resistance, in a leaf assay. Plants regenerated from the Nt(pbg*)T2 and Nt(tbc*)T85 clones were phenotypically resistant to streptomycin. The Nt(pbg*)T13 line yielded both streptomycin resistant and sensitive plants (Table 2).

Inheritance of Antibiotic Resistance in the Transplastgenic Lines

Seeds were collected after selfing, and from reciprocal crosses with wild-type N. tabacum. The seeds were germinated on selective media to test seed transmission of the transgenic traits.

The seed progeny obtained after selfing is uniformly resistant to spectinomycin (Table 3). Lack of segregation indicates that the regenerated plants are homoplasmic for the spectinomycin resistance marker. They carry only one type, the spectinomycin resistant 16SrDNA. In crosses, the resistance is inherited maternally.

The unselected streptomycin resistance was also maternally inherited. Segregation for this trait, however, was found in the selfed seed progeny, and in F1, in the three lines. In addition to the resistant (green) and sensitive (white) seedlings, variegated plants were also observed. Variegation for the streptomycin resistance marker in the progeny indicates that the regenerated plants were heteroplasmic for the unselected streptomycin resistance trait.

The ratio of resistant to variegated to sensitive seedlings differs in subclones of the same line (compare e.g. the Nt(pbg*)T2D and Nt(pbg*)T2C

TABLE 3

Transmission of spectinomycin and streptomycin resistance to the seed progeny

| | | No antibiotic | | | Sp500 | | | Sm500 | | | Sm500/Sp500 | | |
|---|---|---|---|---|---|---|---|---|---|---|---|---|---|
| Line | Progeny | G | W | G/W | G | W | G/W | G | W | G/W | G | W | G/W |
| Nt(tbc) | | 693 | 0 | 0 | 0 | 709 | 0 | 0 | 689 | 0 | 0 | 629 | 0 |
| Nt(tbc)SPC2 | | 227 | 0 | 0 | 315 | 0 | 0 | 309 | 0 | 0 | 311 | 0 | 0 |
| Nt(pbg*)T2C | Self | 670 | 0 | 0 | 866 | 0 | 0 | 3 | 735 | 25 | 0 | 1090 | 16 |
| | $F_1$ | 774 | 0 | 0 | 1204 | 0 | 0 | 1 | 1405 | 20 | 0 | 1370 | 20 |
| | $RF_1$ | 355 | 0 | 0 | 0 | 413 | 0 | 0 | 522 | 0 | 0 | 517 | 0 |
| Nt(pbg*)T2D | Self | 294 | 0 | 0 | 653 | 0 | 0 | 173 | 511 | 62 | 208 | 557 | 40 |
| | $F_1$ | 522 | 0 | 0 | 477 | 0 | 0 | 297 | 369 | 100 | 283 | 329 | 78 |
| | $RF_1$ | 421 | 0 | 0 | 0 | 553 | 0 | 0 | 609 | 0 | 0 | 719 | 0 |
| Nt(pbg*)T13A | Self | 832 | 0 | 0 | 967 | 0 | 0 | 2 | 1033 | 1 | 0 | 889 | 8 |
| | $F_1$ | 998 | 0 | 0 | 840 | 0 | 0 | 2 | 1112 | 11 | 1 | 659 | 12 |
| | $RF_1$ | 650 | 0 | 0 | 0 | 1053 | 0 | 0 | 1030 | 0 | 0 | 1034 | 0 |
| Nt(pbg*)T13C | Self | 580 | 0 | 0 | 766 | 0 | 0 | 4 | 703 | 8 | 4 | 871 | 9 |
| | $F_1$ | 1194 | 0 | 0 | 1203 | 0 | 0 | 0 | 1342 | 7 | 0 | 980 | 3 |
| | $RF_1$ | 495 | 0 | 0 | 0 | 467 | 0 | 0 | 602 | 0 | 0 | 462 | 0 |
| Nt(tbc*)T85A | Self | 497 | 0 | 0 | 556 | 0 | 0 | 0 | 524 | 0 | 0 | 423 | 0 |
| | $F_1$ | 352 | 0 | 0 | 546 | 0 | 0 | 0 | 412 | 0 | 1 | 420 | 3 |
| | $RF_1$ | 531 | 0 | 0 | 0 | 614 | 0 | 0 | 614 | 0 | 0 | 656 | 0 |
| Nt(tbc*)T85B | Self | 592 | 0 | 0 | 635 | 0 | 0 | 179 | 437 | 65 | 274 | 291 | 81 |
| | $F_1$ | 504 | 0 | 0 | 456 | 0 | 0 | 390 | 136 | 31 | 293 | 90 | 30 |
| | $RF_1$ | 810 | 0 | 0 | 0 | 907 | (2)* | 0 | 861 | 0 | 0 | 950 | 0 |

$F_1$, cross in which resistant is female; $RF_1$, cross in which resistant is male; G, green; W, white; G/W, variegated; Sp500, spectinomycin dihydrochloride at 500 µg/ml; Sm500, streptomycin sulfate at 500 µg/ml. The number of seedlings was scored on each antibiotic independently.
*Variegation of these seedlings is probably due to spontaneous mutation.

progenies in Table 3). Note that streptomycin resistant seedlings were found in the seed progeny of the Nt(pbg*) T13A and 13C plants although the plants were phenotypically sensitive in the leaf assay (Table 2). Furthermore, the Nt(tbc*)T85A plant was phenotypically resistant to streptomycin in the leaf assay (Table 2) but was segregating streptomycin resistant seed progeny. These inconsistencies are due to chimerism in the plants, resulting from random sorting of plastids in the absence of selection.

Discussion

The conclusion that spectinomycin resistance in three of the lines is due to transformation is based on recovering the two linked, unselected traits in the same clones. The 148 bombarded samples yielded 3 transplastgenic clones, that is one clone per 50 bombardments (Table 1). Selection for nuclear antibiotic resistance markers yields two to six transgenic clones per bombardment following the same protocol (Klein et al., Proc. Natl. Acad. Sci. USA, 85: 8502–05, 1988). Accordingly, transformation of plastids in this system is about 100 fold less efficient than transformation of the nucleus despite the high number of ptDNA copies in a cell (see below). This contrasts with the Chlamydomonas system (Boynton et al., 1988, supra; Blowers et al., 1989, supra) in which plastid transformation is at least as efficient as nuclear gene transformation (Kindle et al., J. Cell Biol., 108: 2589–2601, 1989) yielding 2 to 100 transplastgenic clones per bombardment.

Transgenic plastids have been obtained by selection for the non-lethal marker, spectinomycin resistance. The same 16S rDNA markers, resistance to streptomycin and spectinomycin, have been used to select for transgenic plastids in Chlamydomonas. Since Chlamydomonas is grown photoautotrophically, the same markers in that organism are lethal.

Non-lethal selection is critical in obtaining the transplastomic lines in higher plants. Higher plants carry a large number of identical plastid genome copies per cell. In *N. tabacum*, the 3,000 to 12,000 copies (Cannon et al., Plant Cell Rep., 4: 41–45, 1985; Yasuda et al., Planta, 174: 235–41, 1988) are localized in up to a hundred plastids (Thomas & Rose, Planta, 158: 329–38, 1983). This contrasts with the 80 ptDNA copies, carried by a single plastid in Chlamydomonas (Harris, *The Chlamydomonas Source Book*, Academic Press, San Diego, p. 354, 1989). Non-lethal selection in higher plants allows sufficient time for the resistant plastid genome copies to increase in numbers to allow phenotypic expression.

Plastid transformation is rare, therefore, we assume that in a transplastomic clone all plastids derive from the same transformed organelle. In each clone, more than one type of transgenic plastic genome was found. These findings can be explained by assuming a multi-step process, involving DNA recombination, copy correction, and sorting out of the transgenic ptDNA copies. Different transgenic plastid genomes may be products of the same initial transformation event, or independent recombination events between copies of vector pZS148 and different copies of ptDNA. The initial transformation event is then followed by copy correction, a mechanism that maintains identical DNA sequence in the two repeat regions of ptDNA (Shinozaki et al., 1986, supra). Copy correction may also generate different transgenic plastid genomes using different copies of the same template. Subsequently, sorting of ptDNA should yield homoplasmic organelles, then homoplasmic cells.

EXAMPLE 2

High-Frequency Plastid Transformation in Tobacco by Selection for a Chimeric aadA Gene This Example was published as Svab & Maliga, Proc. Natl. Acad. Sci. USA 90: 913–17 (February 1993).

The vector pZS148 described in Example 1 above has also been used to accomplish stable plastid transformation in PEG-treated protoplasts of tobacco (Golds et al., Bio/Technology, 11: 95–97, 1993). In addition, the biolistic process described in Example 1 has been used to transform tobacco plastids with a DNA construct containing the same mutant 16S rDNA contained on pZS148, but targeted to the inverted repeat region of the plastid DNA (pJS75, reported in Staub and Maliga, The Plant Cell, 4: 39–45, 1992). However, plastid transformation using the mutant 16S rDNA has proven to be an inefficient process; transformations occurring 2–3 orders of magnitude less frequently than biolistic transformation of nuclear genes. It has been found that one bombardment with DNA-coded microscopic tungsten particle yields 2–20 nuclear gene transformants (Klein et al., Proc. Natl. Acad. Sci. USA, 85: 8502–05, 1988; Kanevski et al., Plant J., 2: 457–63, 1992), whereas one plastid transformant is recovered in about 100 bombarded samples (see Example 1; see also Staub and Maliga, 1992, supra). Selection of plastid transformants in those experiments was by spectinomycin resistance encoded in mutant 16S rRNA genes. It has now been discovered that transformation with a chimeric bacterial aadA gene encoding aminoglycoside 3"-adenylyltransferase dramatically improves the recovery of plastid transformants, yielding frequencies typical of those for nuclear genes.

Materials and Methods

Construction of Vector pZS197

Abbreviations used herein are as follows: ptDNA, plastid DNA; ORF, open reading frame; Prrn, 16S ribosomal RNA promoter. Plasmid pZS197 (FIG. 5) carries a chimeric aadA gene between the tobacco rbcL gene and open reading frame ORF512 (BamHI site at nucleotide 59,286, as per Shinozaki et al.) in a SacII-EcoRV plastid fragment between nucleotides 57,750 and 60,593, respectively cloned into a pBluescript KS(+) phagemid vector (Stratagene).

The 16S rRNA promoter region, Prrn, was cloned from plasmid pJS71 (Staub and Maliga, 1992, supra) as a 252-base-pair (bp) DraI-SphI fragment. Nucleotides at positions 101 and 102 were changed from AT to TC by site-directed mutagenesis (Kunkel, Proc. Natl. Acad. Sci. USA, 88: 488–92, 1985) using oligonucleotide 5'-CTTGTATCCATGCGCTTCgaATTCGCCCGGAGTTC G-3' (Sequence I.D. No. 30) to create an EcoRI restriction site (underlined; mismatches are in lower case). The newly created EcoRI site at the 31' end of the promoter region was linked to the NcoI site at the 5' end of the aadA coding region from plasmid pHC1 (Carrer et al., Plant Mol. Biol., 17: 301–03, 1985) with a synthetic linker obtained by annealing the single-stranded oligonucleotides 5'-AATTCGAAGCGCTTGGATACAGTTGTAGG GAGGGATC-3' (Sequence I.D. No. 31) and 5'-CATG GATCCCTCCCTACAACTGTATCCAAGCGCTTCG-3' (Sequence I.D. No. 32). Subsequently, the EcoRI site was eliminated, and the original sequence was partially restored by a T→A change (position 101 in FIG. 5) with oligonucleotide 5'-GTATCCAaGCGCTTCGtATTCGCCCGGAG-3' (Sequence I.D. No. 33). This oligonucleotide also introduced an A→T mutation at position 110 to remove an upstream AUG (mismatches are in lower case). Nucleotides at the −1 and −2 positions were changed from CC to TT to reproduce the rbcL leader sequence (Shinozaki & Sugiura, Gene, 20: 91–102, 1982) with oligonucleotide 5'-GGCGATCACCGCTTCtgCCATaaATCCCTCCCTAC-3' (Sequence I.D. No. 34; mismatches are in lower case). The same oligonucleotide changed GG to CA at positions 5 and 6 to make the context around the translational initiation codon AUG similar to that of plastid mRNAs (Bonham-Smith et al., Nucleic Acids Res., 17: 2057–80, 1989).

The psbA 3' regulatory region contains nucleotides 533–141 of the tobacco plastid genome (Shinozaki et al.) A Sau3AI site at the 5' end and a TaqI site at the 3' end were converted into XbaI and HindIII sites, respectively, by linker ligation. The psbA 3' region was cloned downstream of the aadA coding sequence as an XbaI-HindIII fragment in plastid pHC1 to generate the aadA 3' region.

Transformation and Regeneration of Transgenic Plants

Transformation of N. tabacum plastids was performed with the DuPont PDS1000 gun-powder charge Biolistic gun as described in Example 1. Spectinomycin-resistant calli and shoots were selected on RMOP medium containing 500 μg of spectinomycin dihydrochloride per ml. Resistant shoots were regenerated on the same selective medium and rooted on MS agar to obtain $T_0$ plants. The first- and second-seed generations of $T_0$ plants are the $T_1$ and $T_2$ generations, respectively.

DNA Gel-Blot Analysis of Total Cellular DNA

DNA was prepared by the method of Mettler, Plant Mol. Biol. Rep., 5: 346–49 (1987). Restriction enzyme-digested DNA was electrophoresed on 0.7% agarose gels and transferred to nylon membrane (Amersham) by using the PosiBlot Transfer apparatus (Stratagene). Blots were probed by using rapid hybridization buffer (Amersham) with $^{32}$P-labelled probes generated by randon priming (Boehringer Mannheim).

Testing of Seedling Phenotypes

Seedling phenotype was determined by plating surface-sterilized seeds on MS medium. On selective medium (spectinomycin or streptomycin at 500 μg/ml, or both at 500 μg/ml) resistant progeny are green, whereas sensitive progeny are white, as described in Example 1.

Results pZS197 Plastid Vector

The aadA gene, encoding aminoglycoside 3"-adenyltransferase, causes spectinomycin and streptomycin resistance in bacteria (Chinault et al., Plasmid, 15: 119–31, 1986). Chimeric aadA genes confer resistance to the same antibiotics in tobacco nuclei (Svab et al., Plant Mol. Biol., 14: 197–205, 1990) and Chlamydomonas chloroplasts (Goldschmidt-Clermont, Nucleic Acids Res., 19: 4083–89, 1991). To express the aadA gene in tobacco plastids, the aadA coding region was placed under control of the strong, constitutive Prrn of the plastid rRNA operon and the 3' untranslated region of the plastid psbA photosynthetic gene. To facilitate translation of the chimeric mRNA, a synthetic ribosome binding site (RBS), designed after the RBS of the abundant rubisco large subunit polypeptide, was incorporated in the 5' regulatory region (FIG. 5). The chimeric aadA gene was cloned between the plastid rbcL and ORF512 genes. These homologous flanking plastic DNA sequences direct the insertion of aadA between rbcL and ORF512 in the plastid genome by two homologous recombination events (see below).

Transformation and Selection of Transplastomic Lines

Transformation with plasmid pZS197 was by the biolistic process, followed by selection of spectinomycin-resistant lines. Resistant shoots and calli appeared in 3–8 weeks on the selective medium. Shoots and calli formed at one site were termed a clone. Plastids in the leaves of these shoots were typically heteroplasmic and contained wild-type and transformed genome copies (see below). Shoots regenerated from leaf sections during a second cycle on spectinomycin-containing medium were termed subclones. Typically, half of the shoots obtained during the second cycle of regeneration were homoplasmic for the transgenome. Since shoot apices form from one or very few cells, plant regeneration is tantamount to single-cell cloning of the chimeric tissue. Homoplasmic shoots at this stage were rooted and transferred to the greenhouse. By this protocol homoplasmic shoots were obtained in 3–5 months.

Spectinomycin resistance may be due to (i) integration of aadA into the plastid genome, (ii) integration of aadA into the nuclear genome and fortuitous expression from an upstream promoter, or (iii) occurrence of a spontaneous plastome mutation. In 79 bombarded leaf cultures, 84 spectinomycin-resistant clones were isolated. DNA gel-blot analysis confirmed that 40 of 50 clones had integrated aadA into the plastid genome (see below). The remaining 10 clones did not hybridize with the aadA probe and are spontaneous mutants.

Integration of aadA into Plastid DNA (ptDNA) and Sorting of Wild-Type Transformed Genome Copies Screening of subclones after the second selection cycle is shown in FIG. 6. Total cellular DNA was extracted from leaves and probed with wild-type rbcL/ORF512 (probe P1) and aadA (probe P2) sequences. DNA gel blots indicated two types of integration events, yielding genomes, T1ptDNA and T2ptDNA.

Figure 6A:
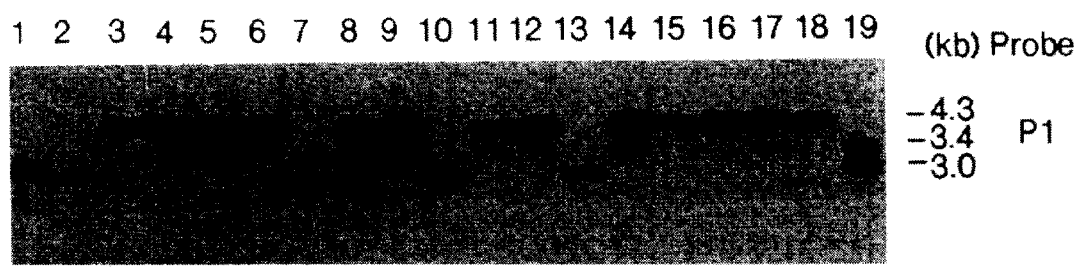
FIGS. 6A–6E—Probing of DNA gel blots to confirm plastid transformation. Total cellular DNA was digested with EcoRI and EcoRV restriction enzymes for which there are no sites in plasmid pZS197. Blots were probed with the targeting plastid DNA fragment encoding the rbcL and ORF512 genes (FIG. 6A) and the aadA coding region (FIG. 6B). Lanes: 1 and 2, DNA from wild-type recipient tobacco leaves; 3–19, DNA extracted from the spectinomycin-resistant lines pZS197-159, -160, -162, -166, -172, -175, -177, -179, -182, -183, -193, -185, -186, -187, -188, -189 and -173.
Figure 6B:
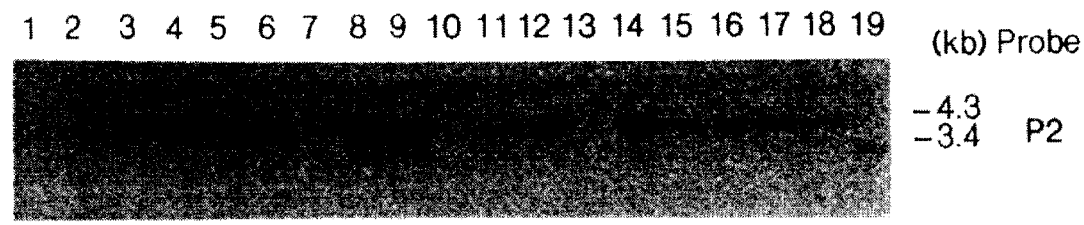
Figure 6C:
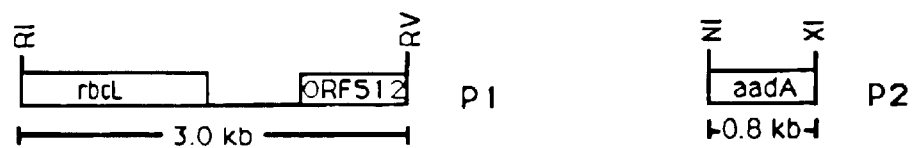
Figure 6D:
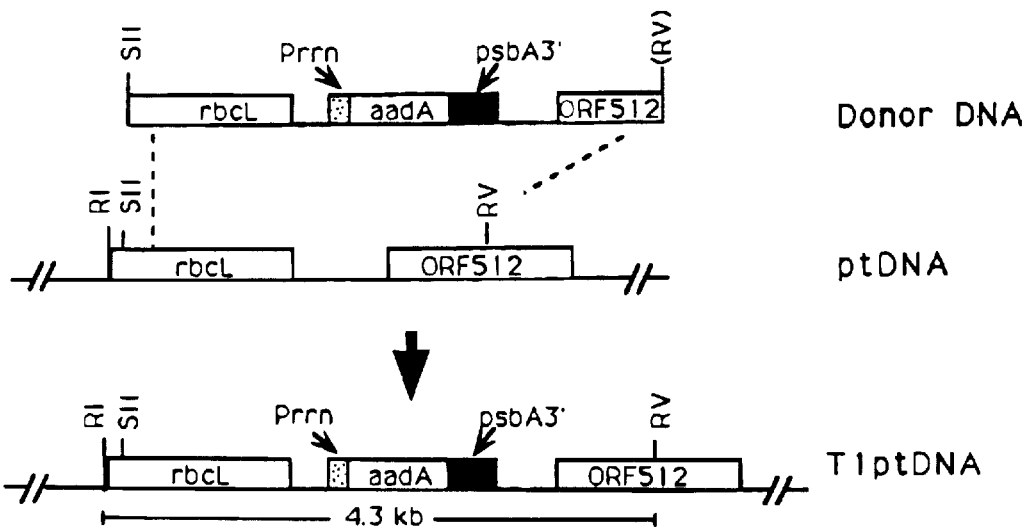

T1ptDNA resulted from incorporation of the 1.3-kb aadA gene into the 3.0-kb fragment containing rbcL and ORF512 by two homologous recombination events (FIG. 6D and FIGS. 7A and B). Digestion of the T1ptDNA with EcoRI and EcoRV restriction endonucleases yielded a 4.3-kb fragment hybridizing with both the targeting sequences and the aadA probe. Some of the lines carried only transformed genome copies and therefore are homoplasmic (for example, lanes 4, 5 and 6 in FIGS. 6A and B). Others were heteroplasmic and carried both wild-type (3.0 kb) and transgenic (4.3 kb) fragments when probed with the targeting sequences (for example, lane 3 in FIG. 6A). Homoplasmic shoots from such heteroplasmic clones were readily obtained by regenerating plants on a selective medium.

Figure 6E:
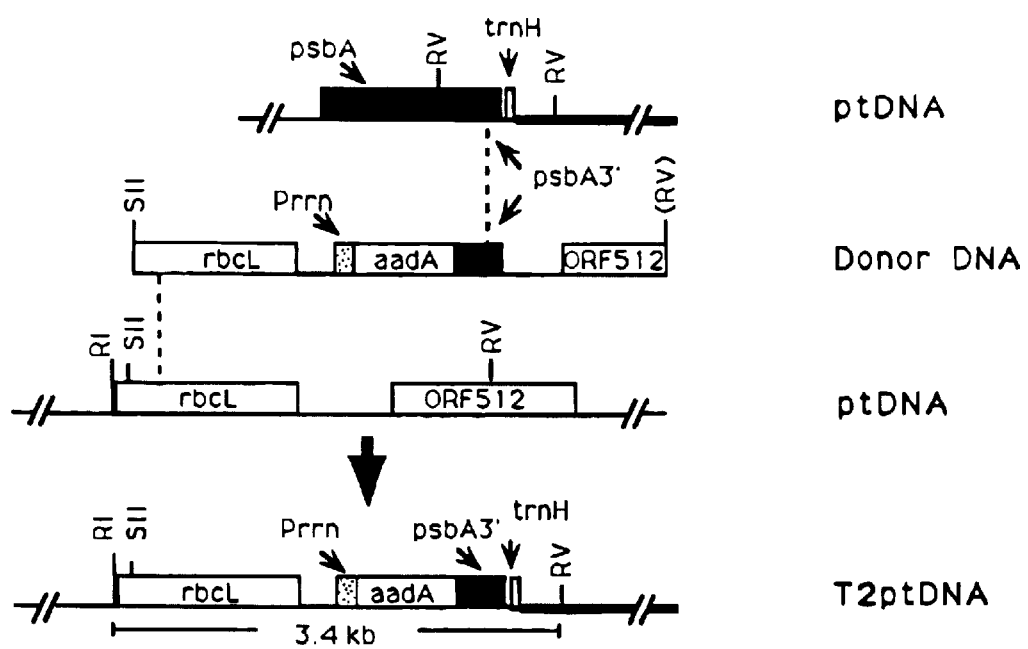

In about half of the clones, in addition to T1ptDNA-type integration events, an unexpected 3.4-kb fragment was also present. The 3.4-kb fragment is a minor component in most clones, except pZS197-173 plastids (lane 19 in FIGS. 6A and B) in which this was the only fragment hybridizing with the aadA probe. To determine its origin, the fragment was cloned from pZS197-173 plastids and sequenced. Sequencing revealed that the aadA 3' region (derived from the endogenous psbA gene) is followed by trnH and the inverted repeated (FIG. 6E) as in the wild-type plastid genome. Therefore, the 3.4-kb fragment is also a product of two homologous recombination events via (i) the endogenous and donor 1.55-kb rbcL sequences and (ii) the 0.4-kb aadA 3' region and the endogenous psbA gene 3' region. The proposed T2ptDNA-structure is shown in FIG. 7C. Regions of the donor DNA and of the wild-type plastid genome involved in forming T2ptDNA are shown in FIG. 6E. T2ptDNA may have been formed by a multistep process immediately after the introduction of the donor DNA or later, from T1ptDNA, by recombination via the homologous aadA and psbA 3' regions and copy correction.

The proposed T2ptDNA (FIG. 7C) would lack a 26-kb region between aadA and the inverted repeated, as compared with T1ptDNA (FIG. 7B). The putative deleted region contains ribosomal protein genes (Shinozaki et al.) required for plastid maintenance. Evidence supporting formation of defective transgenomes are (i) rapid loss of T2ptDNA in the absence of selection and (ii) failure of repeated efforts to purify T2ptDNA to homoplasmy. Accordingly, the T2ptDNA genome in the pZS197-173 line could be maintained only in balanced heteroplasmic plants, in which the transgenomes conferred phenotypic resistance and the wild-type genomes complemented the deleted functions.

Presence of the Chimeric aadA Gene in the Seed Progeny

Seed transmission of the chimeric aadA was studied in populations of 500–800 seedlings of the T1ptDNA-type clones pZS197-159, pZS197-160, and pZS197-162. The resistance phenotype was determined by germinating $T_1$ generation seedlings on selective medium. Resistant seedlings were green, whereas sensitive seedlings were white. Uniform spectinomycin resistance in the selfed seed progeny indicates that aadA is maintained in plants grown to maturity in greenhouse. The $F_1$ progeny obtained by pollinating transplastomic flowers with wild-type pollen were also uniformly resistant, whereas progeny from the reciprocal crosses (wild-type female, transplastomic pollen) were sensitive to spectinomycin. Lack of pollen transmission of the transplastomic aadA gene is expected in tobacco, a species with strict maternal inheritance of its plastids.

Stability of the aadA gene in ptDNA was further confirmed by uniform resistance of 21,000 $T_2$ generation seedlings. About 7,000 seedlings were tested from each of the three transplastomic lines.

Discussion

Transformation efficiency with the chimeric aada gene is about 100-fold greater than with antibiotic resistance encoded by mutations in 16S ribosomal RNA genes and approaches the frequency of nuclear gene transformation by the biolistic process. The increase in the transformation frequency is likely due to an improved recovery of the newly formed transgenomes by the dominant aadA gene (see Section II of the Detailed Description).

Integration of aadA was by two homologous recombination events via (i) the rbcL (1.55 kb) and ORF512 (1.29 kb) genes or (ii) the rbcL (1.55 kb) and psbA 3' (383 bp) regions. Interestingly, no recombination was detected between the aadA promoter region and its cognate source. This may be due the short sequence homology (120 bp), relative position, or nature of homologous sequences.

EXAMPLE 3

High-Frequency Plastid Transformation in Tobacco Using Kanamycin Resistance as a Selectable Marker In this Example (published as Carrer et al., Mol. Gen. Genet. 241: 49–56, 1993), the feasibility of using kanamycin resistance as a non-lethal selectable marker for plastid transformation was tested. Resistance to this drug is a frequently used marker in vectors designed for the introduction of foreign genes into higher plant nuclei since it is selectable in a large number of species and spontaneous mutation for resistance to this drug has not yet been reported. Kanamycin resistance is due to expression of a kan gene from the bacterial transposon Tn5 (Berg et al., Proc. Natl. Acad. Sci. USA, 72: 3628–32, 1975) or the neo gene (Beck et al., Gene, 19: 327–36, 1982), encoding neomycin phosphotransferase (NPTII).

Materials and Methods

Construction of vector pTNH32

Plasmid pTNH32 (FIG. 8) carried a chimeric kan gene between the tobacco rbcL and ORF512 genes (BamHI site at nucleotide 59,286; Shinozaki et al.) in a SacII-EcoRV plastid fragment representing the region between nucleotides 57,750 and 60,593, respectively, cloned into a pBluescript KS$^+$ phagemid vector (Stratagene). The NPTII coding region was cloned as an NcoI-XbaI fragment into a precursor of plasmid pZS197 (FIG. 5; Example 2), with an NcoI site including the trnaslational initiation coding of aadA and an XbaI site downstream of the aadA coding region (Example 2). In this plasmid, the NPTII coding region is downstream of a modified ribosomal RNA operon promoter, Prrn (Sequence I.D. No. 1), which has the rbcL ribosome binding site and lies upstream of the psbA 3' regulatory region. The NcoI site was removed, and the five N-terminal amino acids of the ribulose-1,5-bisphosphate carboxylase/oxygenase (Rubisco) large subunit (LSU) were fused with NPTII by incorporating the oligonucleotide 5'-CCATCTTGTTCAATCCCCTCTGTTTGTGGTGACAT AAATCCCTCCCTACAAC-3' (Sequence I.D. No. 35). oligonucleotide-directed mutagenesis was carried out according to Kunkel (1985), supra. The sequence of the promoter and of the region encoding the LSU/NPTII fusion is shown above plasmid pTNH32 in FIG. 8.

The source of the NPTII coding sequence was pTNH4, a derivative of plasmid pLGV1103 described by Czernilofsky et al., DNA, 5: 101–03 (1986). The kan sequence (Beck et al., Gene, 19: 327–36, 1982) in this plasmid was modified by oligonucleotide-directed mutagenesis so that the NPTII coding region could be excised by the NcoI and XbaI restriction endonucleases. Construction included the following steps: (i) the internal NcoI site was removed by mutagenesis with the oligonucleotide 5'-GCAGGCATCGCCATGT GTCACGACGAGATCCTC-3' (Sequence I.D. No. 36); (ii) an NcoI site (underlined), including the translational initiation codon, was created using oligonucleotide 5'-GCAATCCATCTTGTTCAATCC<u>CCATGG</u>TCATGGG CCGGATCTG-3' (Sequence I.D. No. 37); (iii) an internal PstI site was removed by mutagenesis with oligonucleotide 5'-GCCTCGTCCTGGAGTTCATTCAGGGC-3' (Sequence I.D. No. 38); and (iv) the BstBI site 15 nucleotides downstream of the kan stop codon was ligated to a blunted BamHI cloning site adjacent to an XbaI site in plasmid pUC120 so that the NPTII coding region could be isolated as an NcoI-XbaI fragment.

Transformation, Selection of Kanamycin-resistant Lines and Testing for Phenotypic Resistance (*Nicotiana tabacum* cv. Petit Havana) plants were grown, and leaf sections bombarded with tungsten microprojectiles coated with pTNH32 DNA, as described in Examples 1 and 2.

Resistant calli and shoots were selected on RMOP medium containing 50 μg/ml of kanamycin monosulfate (filter-sterilized). Resistant shoots were regenerated on the same selective medium, and rooted on MS agar to obtain plants. Levels of kanamycin resistance of the regenerated plants were determined by incubating leaf disks on media containing different concentrations of the selective drug.

The seedling phenotype was determined by plating surface-sterilized seeds on MS medium containing 200 μg/ml kanamycin monosulfate. Resistant seedlings are green, sensitive seedlings are white on this selective medium.

DNA Gel Blot Analysis of Total Cellular DNA

Total cellular DNA was prepared by the method of Mettler (1987, supra). Restriction enzyme-digested DNA was electrophoresed in 0.8% agarose gels and transferred to nylon membrane (Amersham) using the PosiBlot Transfer apparatus (Stratagene). Blots were probed using Rapid Hybridization Buffer (Amersham) with $^{32}$P-labelled probes generated by random priming (Boehringer-Mannheim).

Immunoblotting

Protein was extracted in the buffer of Ramesh and Osborne, Anal. Biochem., 193: 316–18 (1991). Protein concentrations were determined using the BioRad protein assay reagent kit. For immunoblots, protein extracts were electrophoresed in 10% SDS-polyacrylamide gels (Laemmli, Nature, 227: 680–85, 1970), and transferred to Immobilon-P membrane (Millipore) using a semi-dry transfer apparatus (Integrated Separation Systems). Immunoblot detection used ECL chemiluminescense and 1:10,000 diluted HRP-conjugated secondary antibody (Amersham). Polyclonal rabbit antiserum to NPTII was purchased from 5Prime→3Prime, and diluted 1:1000 for probing, NPTII was quantified on the immunoblots by comparison of experimental samples with the commercial NPTII standard (5Prime→3Prime), and a dilution series.

Results pTNH32 Plastid Vector

Figure 8:
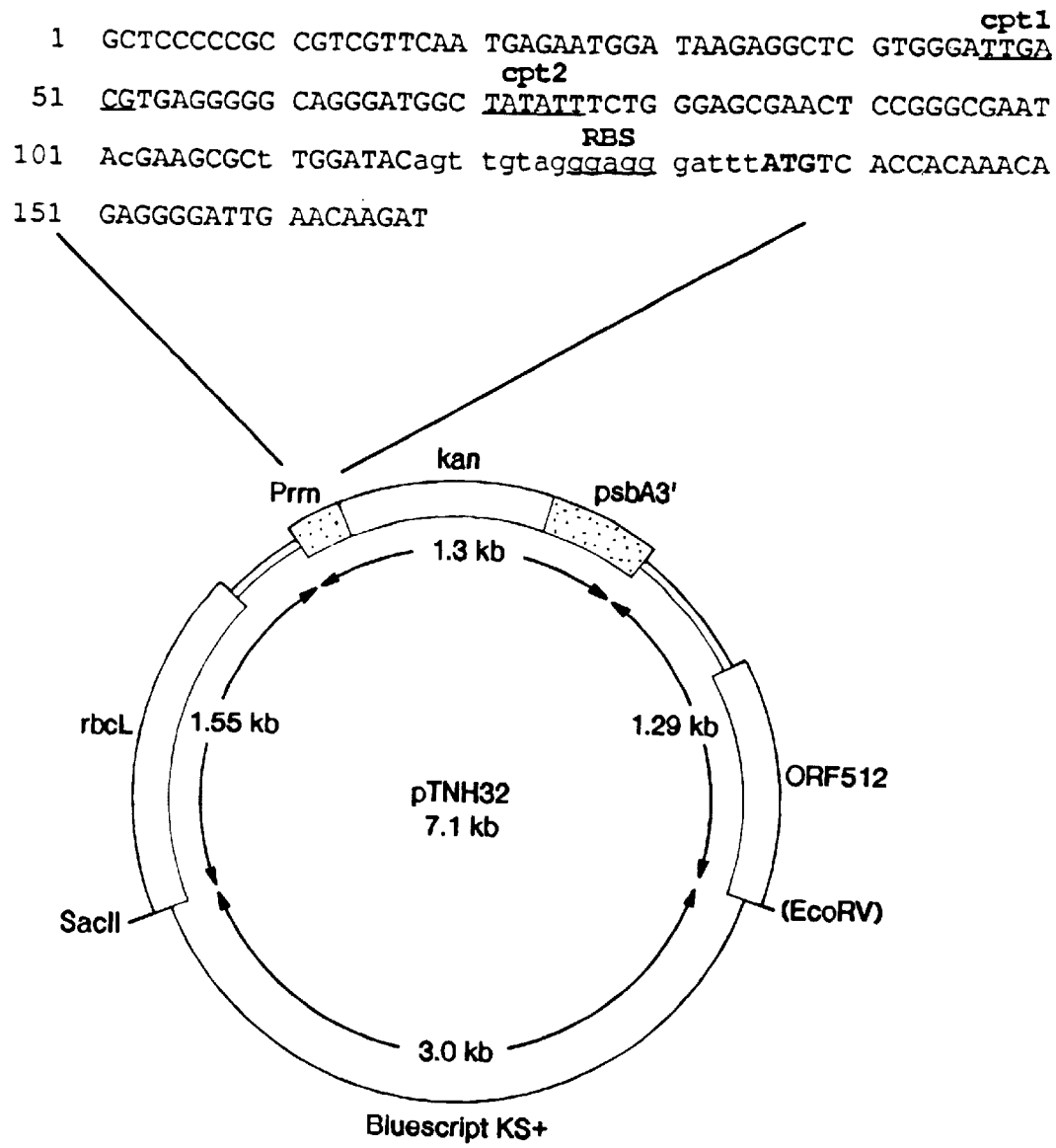
FIG. 8—The pTNH32 plastid transformation vector. The chimeric kan gene was cloned into a SacII-EcoRV plastid DNA fragment between the rbcL and ORF512 genes (coding regions marked by boxes) in the 3kb pBluescript vector (thin line). In the chimeric gene, kan expression is controlled by a modified plastid ribosomal RNA operon promoter, Prrn, and the 3' region of the plastid psbA gene (psbA3'). Prrn is transcriptionally fused with the rbcL leader sequence, including the ribosome binding site (RBS), and the first five amino acids of the ribulose-1,5-bisphosphate carboxylase/oxygenase large subunit (nucleotides 118–153 of Sun et al., supra) to form Sequence I.D. No. 2. The GGG codon (nucleotide 154) is the second codon of the kan open reading frame in plasmid pTNH4. Fragment sizes are shown inside the map.

To express kan in plastids, the NPTII coding region (830 bp) was cloned downstream of Prrn, the strong constitutive promoter of the ribosomal RNA operon transcriptionally fused to the 5' untranslated region of the rbcL gene (including the ribosome binding site) and the first five codons of rbcL. As a result, the NPTII polypeptide was fused at its N-terminus to the first five amino acids of the Rubisco large subunit (FIG. 8). To ensure stability of the chimeric mRNA, the 3' regulatory region of the plastid psbA photosynthetic gene was cloned downstream of the NPTII coding region. Insertion of the chimeric kan gene from vector pTNH32 into the plastid genome was targeted by cloning it into the intergenic region of rbcL and ORF512 in a plastid DNA fragment (FIG. 8).

Transformation and Selection of Kanamycin-Resistance Clones

Tungsten particles (1 μm) were coated with plasmid pTNH32 DNA, and introduced into tobacco leaves (6–8 cm² per sample). The leaves were incubated for 2 days in the absence of drugs, then were cut into 10–15 sections, and transferred onto RMOP plant regeneration media containing kanamycin (50 μg/ml). In one experiment, in 50 bombarded leaf samples, callus and shoot proliferation was observed at 52 distinct locations. Resistant callus and shoots at one location are termed a clone; different shoots regenerated from the same clone are termed subclones. Plastid transformants were identified by Southern probing of total cellular DNA isolated from the resistant callus and shoots (see below). Since shoots of the plastid transformants at this stage contained a mixed population of wild-type and transformed plastid genome copies, new shoots were regenerated from leaf sections on a selective medium. Shoot apices form from one or a very few cells, therefore, shoot regeneration represents single-cell cloning of the chimeric tissue. This cloning procedure was repeated twice. Shoots with uniformly transformed plastid genome copies were rooted and transferred to the greenhouse. By this procedure, two plastid transformants were identified among the 52 kanamycin-resistant clones.

Classification of Kanamycin Resistant-clones by DNA Gel Blot Analysis

Kanamycin resistance may be due to integration of the chimeric kan gene into the plastic genome via the flanking rbcL and ORF512 sequences, or integration of kan into the nuclear genome and expression from an upstream promoter. In the discussion below, clones are identified by a number following P and N for plastid and nuclear transformants, respectively.

DNA gel blot analysis of total cellular DNA identified plastid transformants after digestion with EcoRI and EcoRV restriction endonucleases (FIG. 9). Note that these sites are absent from the transforming DNA, therefore digestion with these enzymes yields 3.0 kb and 4.3 kb fragments from the wild-type and transformed plastid genomes, respectively (FIG. 9E). Both of these fragments hybridize with the rbcL/ORF512 targeting sequence (FIG. 9A). Note a mix of wild-type and transformed genome copies in the P70 and P107 callus samples, a reduced amount of wild-type genome copies in P70B and P107A,B subclones, and the absence of wild-type genome copies in the homoplasmic subclone P70A, and its seed progeny (FIG. 9C). A repeated cycle of shoot regeneration yielded homoplasmic plants from each of the subclones (not shown). The kan coding region probe hybridizes only with the 4.3 kb transgenic fragment, as expected (FIG. 9B). The 3.4 kb fragment present in most transplastomic clones is likely to be formed by homologous recombination between the kan 3' (derived from psbA) and the endogenous psbA 3' regions, as shown with the chimeric aadA gene of Example 2. This recombination event yields a defective plastome, and is rapidly lost in the absence of drug selection.

Figure 9A:
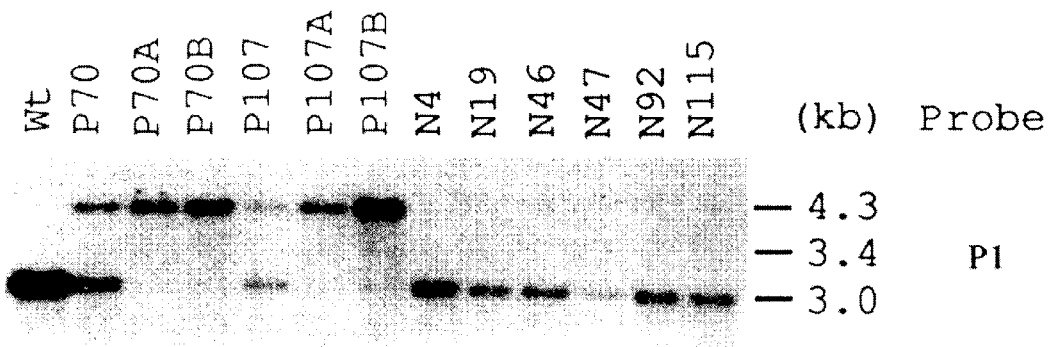
FIGS. 9A–9E—Southern blot analysis to confirm plastid transformation.
Figure 9B:
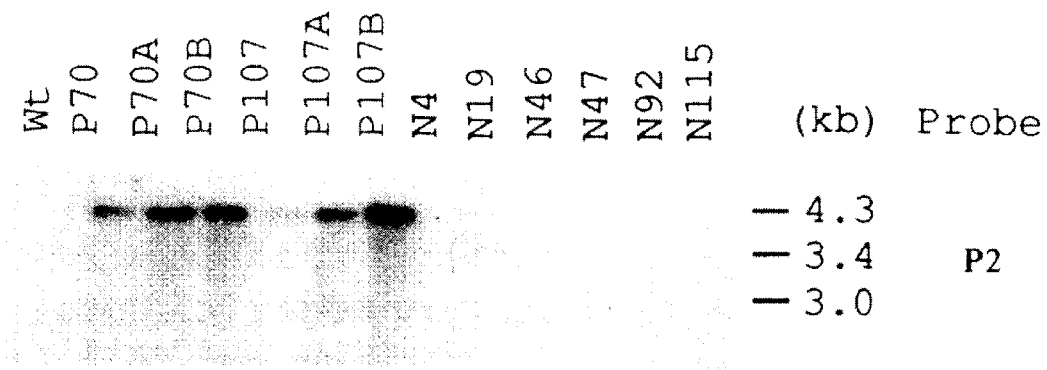
Figure 9C:
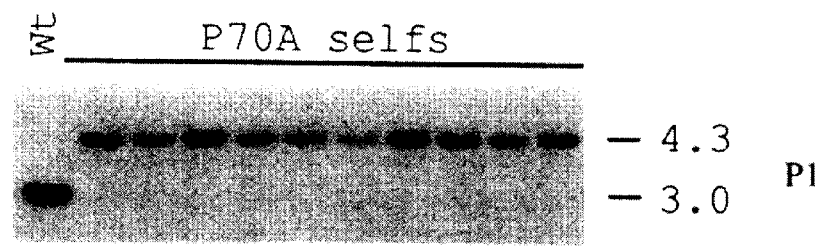
Figure 9D:
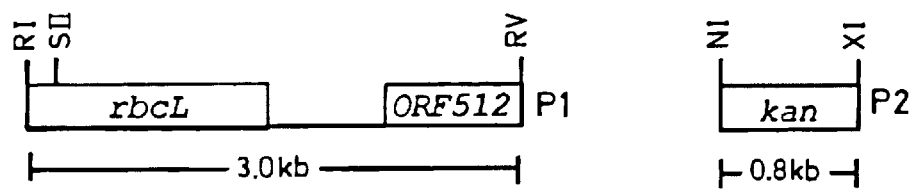
Figure 9E:
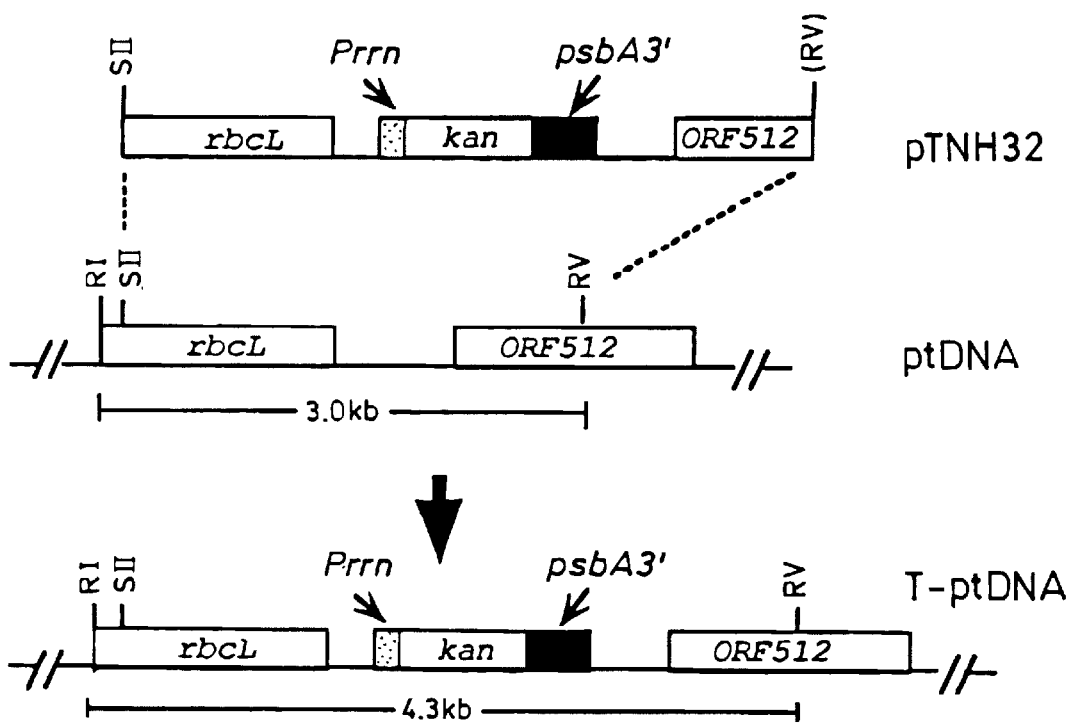

The kan probe readily detected the chimeric kan gene that is present in a high copy number (10,000) per leaf cell. However, under the same conditions, it failed to detect the few integrated nuclear kan copies in clones N4-N115 (FIG. 9B). These clones carried only the 3.0 kb wild-type plastid fragment when probed with the rbcL/ORF512 targeting sequence (FIG. 9A). Evidence for nuclear localization of kanamycin resistance in these clones is provided by the observation of pollen transmission and Mendelian segregation for the resistance marker in the seed progeny (see below).

Accumulation of NPTII and Levels of Kanamycin Resistance

Figure 10:
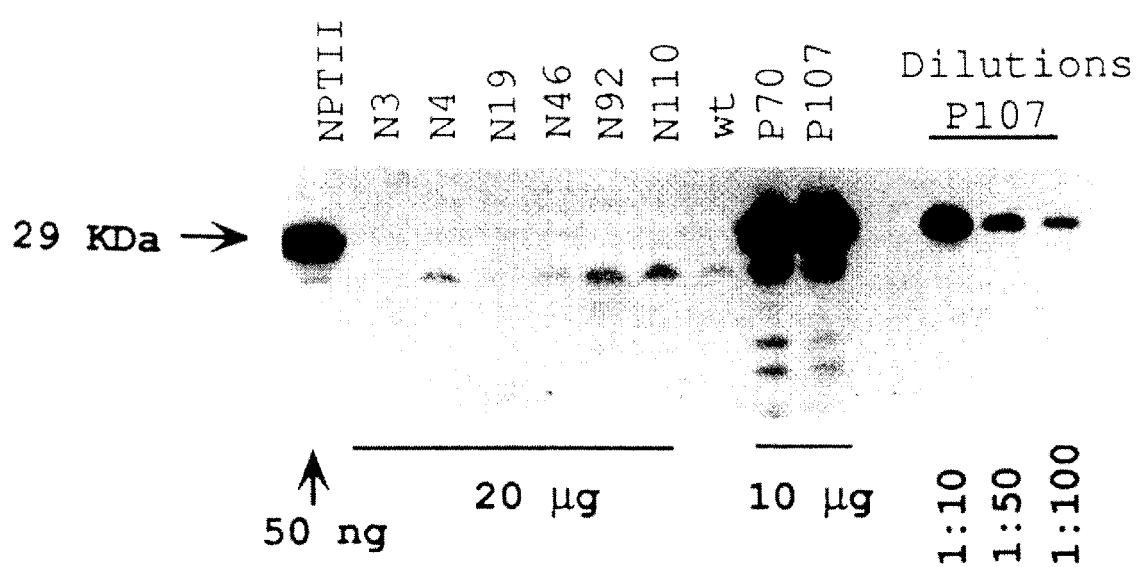
FIG. 10—Immunoblot to confirm neomycin phosphotransferase (NPTII) accumulation in tranplastomic leaves. Lanes contain protein extracts from the leaves of: N3, N4, N19, N46, N92 and N110 nuclear transformants; wt, wild-type tobacco; P70B and P107C homoplasmic plastid transformants. Dilution series of the P107C leaf sample, and a commercial NPTII standard (NPTII) are included.

Total cellular protein was extracted from the leaves of the kanamycin-resistance plants, fractionated by SDS-PAGE, blotted onto membranes and probed with antibody to NPTII (FIG. 10). NPTII was quantified by comparing a dilution series of a leaf extract with purified commercial enzyme. In the two independent transformants, P70A and P107A, about 1% of the total leaf protein is NPTII, based on comparison of the NPTII standard with the leaf extract dilution series. Lack of a positive 29 kDa signal in the nuclear transformants after over-exposure (not shown) indicates that these plants contain at least 1,000 times less NPTII than the plastid transformants. Indeed, 3–4 ng NPTII per mg total protein (0.0003% of total cellular protein) expressed from a nuclear gene in the cytoplasm is sufficient for the growth of tobacco cells on a medium containing 50 μg/ml kanamycin monosulfate (Kanevski et al., Plant J., 2: 457–63, 1992). No attempt was made to detect the low levels of NPTII in the nuclear transformants. Note that a non-specific band in the wild-type control (Nt) is similar in size to an NPTII degradation product.

Given the large difference in NPTII accumulation between the plastid and nuclear transformants, levels of kanamycin tolerance were compared by growing leaf sections on drug-containing medium. In general, plastid transformants P70 and P107 are more tolerant to kanamycin than the nuclear transformants, since leaf sections of these plants formed callus in the presence of 500 μg/ml kanamycin. However, three of the ten nuclear transformants were also resistant to 500 μg/ml kanamycin. One of these, N46, grew in the presence of 1000 μg/ml kanamycin (Table 4). It is interesting to note that the N46 nuclear transformant did not contain NPTII levels comparable to those in the plastid transformants (FIG. 10)

TABLE 4

Kanamycin Resistance of Transgenic Plants

| Clones | Kanamycin (μg/ml) | | | | | |
|---|---|---|---|---|---|---|
| | 50 | 100 | 200 | 500 | 1000 | 2000 |
| Non-transformed control plants | − | − | − | − | − | − |
| Nuclear transformants | | | | | | |
| N3 | + | + | + | + | − | − |
| N4 | + | + | + | − | − | − |
| N19 | + | + | + | − | − | − |
| N20 | + | + | − | − | − | − |
| N46 | + | + | + | + | + | − |
| N48 | + | + | − | − | − | − |
| N67 | + | + | + | + | − | − |
| N92 | + | + | + | − | − | − |
| N110 | + | + | + | − | − | − |
| N115 | + | + | + | − | − | − |
| Plastid transformants | | | | | | |
| P70A | + | + | + | + | − | − |
| P107C | + | + | + | + | − | − |

+, indicates callus and shoot formation; −, no growth

Screening of Plastid Transformants for Resistance to High Levels of Kanamycin

Plastid transformants accumulate NPTII at much higher levels than nuclear gene transformants, resulting in a higher level of kanamycin resistance. Therefore, in Experiment II, clones isolated by resistance to 50 μg/ml of kanamycin were screened for resistance to 500 μg/ml of the drug. In 25 bombarded samples, 4 out of 47 clones were resistant to the high kanamycin concentration. Southern probing confirmed plastid transformation in one of the four clones (not shown).

Inheritance of Kanamycin Resistance in the Seed Progeny

Inheritance of the kanamycin resistance phenotype was studied in the seed progeny of the regenerated plants by germinating seed on media containing 200 μg/ml of kanamycin monosulfate. On this medium, resistant seedlings are green whereas sensitive seedlings are bleached.

In homoplasmic P70A and P107C plants, with kan incorporated into the plastid genome, resistance is inherited maternally (Table 5). Selfed seed progeny of the homoplasmic plants were uniformly resistant whereas in crosses, resistance is transmitted by the female parent only. Accordingly, the $F_1$ progeny (transplastomic female, wild-type pollen parent) are uniformly resistant whereas the $RF_1$ progeny (wild-type female, transplastomic pollen parent) are uniformly sensitive.

In lines that did not contain kan in the plastid genome, nuclear localization of the chimeric gene was confirmed by Mendelian inheritance of the kanamycin resistance phenotype. In the selfed seed progeny of regenerated plants, the ratio of resistant to sensitive seedlings is 3:1; in the $F_1$ and $RF_1$ progeny (see above) it is 1:1 (Table 5).

TABLE 5

Inheritance of Kanamycin Resistance in the Seed Progeny

|  | Selfs (R:S) | | F$_1$ (R:S) | | RF$_1$ (R:S) | |
| --- | --- | --- | --- | --- | --- | --- |
| Clones | Observed | (expected) | Observed | (expected) | Observed | (expected) |
| Nuclear transformants | | | | | | |
| N4 | 160:80* | (3:1) | 74:142* | (1:1) | 157:185 | (1:1) |
| N46 | 190:39* | (3:1) | 138:111 | (1:1) | 116:115 | (1:1) |
| N92 | 155:66 | (3:1) | 140:103* | (1:1) | 181:138* | (1:1) |
| N115 | 162:56 | (3:1) | 120:139 | (1:1) | 92:124* | (1:1) |
| Plastid transformants | | | | | | |
| P70A | 238:0 | (1:0) | 206:0 | (1:0) | 0:204 | (0:1) |
| P107C | 307:0 | (1:0) | 137:0 | (1:0) | 0:179 | (0:1) |

The ratio of resistant (R) to sensitive (S) seedlings, and the expected ratio (in brackets), is given. Selfs, selfed seed progeny; F$_1$, seedling from crossing transgenic as female and wild type as male; RF$_1$, reciprocal cross, in which wild type is female, transgenic is pollen parent. In nuclear transformants, ratios marked with * indicate significant deviation from expected ratio (p > 0.05)

Discussion

The rbcL/ORF512 "targeting" clone and the chimeric kan gene expression cassette employed in this study have been successfully tested with the aadA coding region, as described in Example 2. The only difference between the tobacco aadA and kan constructs is fusion of five amino acids of the Rubisco large subunit with the NPTII enzyme. Fusion of the N-terminal portion of plastid polypeptides with aadA was necessary to obtain spectinomycin resistance in Chlamyhdomonas (Goldschmidt-Clermont, 1991, supra). Such protein fusions were not required to obtain phenotypic resistance in tobacco with chimeric aadA (Example 2) and kan (unpublished) constructs, or for the accumulation of β-glucuronidase from chimeric uidA genes in tobacco (see Example 4 herein) and Chlamydomonas (Sakamoto et al., Proc. Natl. Acad. Sci. USA, 90: 497–501, 1993).

Data in this Example suggest that kan is 20-to 30-fold less efficient for the recovery of plastid transformants than is aadA. With kan, on average, one transplastomic clone was obtained per 25 bombarded leaf samples whereas with aadA, one transplastomic clone was obtained for each of the samples. This may be due to the lack of phenotypic resistance in the kan plastid transformants until most of the plastid genome copies are transformed. Since kanamycin effectively inhibits cell division while spectinomycin does not (Example 1), kanamycin does not facilitate sorting out of the transformed plastid genome copies by allowing repeated healthy cell divisions. The lowest level of kanamycin that may be used for selection and which allows some residual growth is 50 μg/ml. Longer phenotypic expression time, that is longer cultivation in the absence of kanamycin after bombardment, should lead to an improved recovery of plastid transformants on kanamycin medium due to the extended time period available for transplastome replication and sorting.

In higher plants, kanamycin-resistant mutants have not yet been described. Therefore, kanamycin-resistant clones that do not carry a chimeric kan gene in their plastids should be the result of integrating kan into the nuclear genome. Indeed, selection of nuclear gene transformants with other plastid kan genes (Cornelissen and Vandewiele, Nucleic Acids Res., 17: 19–29, 1989), and with promoterless kan constructs (Koncz et al., Proc. Natl. Acad. Sci. USA, 86: 8467–71, 1989) confirms that kanamycin-resistant clones may be readily obtained by transformation with constructs that were not designed for expression in the nucleus.

The large number of nuclear kan transformants obtained, on average one per bombarded sample, was surprising since no nuclear spectinomycin-resistant transformants were obtained when aadA was introduced in the same expression and targeting cassettes (Example 2). It is likely that the two chimeric genes are incorporated into the nuclear genome at similar frequencies. Isolation of nuclear transformants after bombardment with kan, but not with aadA, suggests a requirement for a much lower level of NPTII accumulation in the cytoplasm to obtain phenotypic resistance.

Incorporation of kan into the plastid genome led to its amplification in leaves to a high copy number, about 10,000 per cell. As a result, NPTII accumulated to levels as high as 1% of total cellular protein. Example 4 herein describes accumulation of β-glucuronidase from a chimeric uidA gene in plastids to levels of about 2.5% of total cellular protein. Taken together, these data confirm the potential of the plastid organellar compartment for the expression of foreign polypeptides.

EXAMPLE 4

Plastid Transformation in Tobacco and Tissue-Specific or Light-Inducible Accumulation of the Reporter Gene Product, β-glucuronidase (GUS)

In this example (published as Staub & Maliga, EMBO J. 12: 601–06, February 1993), a chimeric uidA gene encoding β-glucuronidase (GUS) under control of the psbA 5'- and 3'-regulatory regions (224 and 393 bp, respectively) was integrated into the tobacco plastid genome. The effect of the 5' psbA regulatory region on expression of the uidA gene was evaluated by monitoring the accumulation of the reporter gene product, GUS, under different conditions.

Materials and Methods

Plastid Transformation Vector pJS80

In plasmid pJS25, the uidA coding region is under control of the psbA gene expression signals (Sugita & Suguira, Mol. Gen. Genet. 195: 308–13, 1984) in plasmid pUC119 (Vieira and Messing, Meth. Enzymol. 153: 3–11, 1987). The 224 bp psbA 5'-regulatory region contains the promoter and the entire leader sequence from SmaI at nucleotide position 1817 in the ptDNA (Shinozaki et al.) to the psbA translational initiation codon ATG (at nucleotide 1595) that is now included in an NcoI site. The NcoI site (underlined, mismatch in lower case) containing the translation initiation codon was created using synthetic oligonucleotide-5'-TTTTA<u>CCATGg</u>CTGCAAT-3' (Sequence I.D. No. 47), as a template for site-directed mutagenesis, as described in Examples 2 and 3. The 393 bp psbA 3'-flanking region from the Sau3AI site at nucleotide 530 of ptDNA to the TaqI site at nucleotide 141 of ptDNA contains the stem-loop structure required for mRNA stability (Stern & Gruissem, Cell, 51: 1145–57, 1987). This fragment was cloned into the BamHI/AccI sites of pUC119. The BamHI site was blunted by filling in with the Klenow fragment of DNA polymerase I and ligated with an XbaI linker (5'-GCTCTAGAGC-3'; Sequence I.D. No. 39). The psbA 3'-end was subsequently cloned as an XbaI-SphI fragment into the polylinker downstream of the psbA 5'-end to create the psbA expression cassette in plasmid pJS23.

The source of uidA coding region was plasmid pRAJ275 (Jefferson, *Genetic Engineering*, J. K. Settlow, ed.; Plenum Press, N.Y., Vol. 10, pp. 247–263; 1988). Plasmid pJS8 was obtained from pRAJ275 by converting the EcoRI site downstream of the uidA coding region into an XbaI site by linker ligation. Plasmid pJS25 was obtained by cloning the 1.87 kb NcoI/XbaI uidA coding region into NcoI/XbaI digested plasmid pJS23. The chimeric uidA gene was isolated from plasmid pJS25 as a 2.5 kb SmaI-PstI fragment, blunted and ligated into the DraI site of plasmid pJS75 (Staub and Maliga, 1992, supra) to create plasmid pJS80.

Plant Lines

Figure 11A:
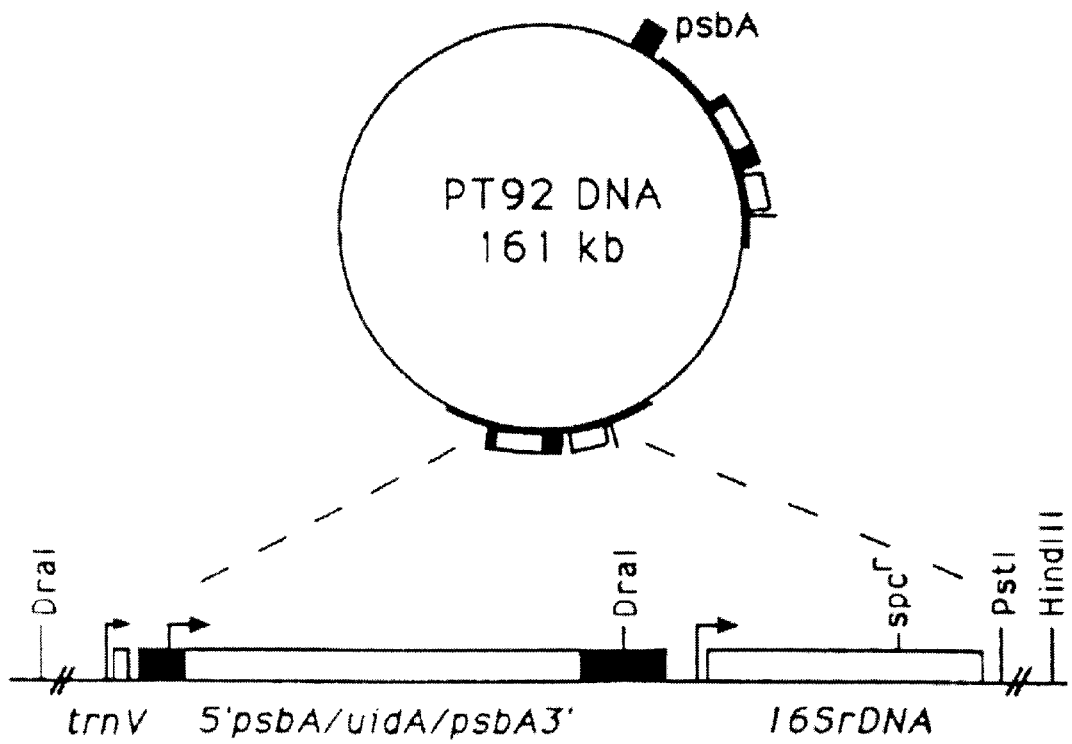
FIGS. 11A–11B—The PT92 transplastomic line.

PT92 transplastomic line was obtained by transforming wild-type *Nicotiana tabacum* cv. Petit Havana (tobacco) leaves with pJS80 DNA using the DuPont PDS1000 gunpowder charge Biolistic gun, as described in the previous Examples. Selection was for the SPC1 allele of the 16SrDNA gene (see Example 1, and Svab & Maliga, Mol. Gen. Genet., 228: 316–19, 1991) by resistance to 500 $\mu$g/ml of spectinomycin dihydrochloride. In 193 bombarded leaf cultures, 30 spectinomycin resistant clones were obtained. One of these, PT92, contains the PstI RFLP marker and the chimeric uidA gene in homoplasmic form (FIG. 11). PT92K and PT920 are independently regenerated plants and carry identical transplastomes.

The transgenic tobacco plant with the nuclear 35SuidA gene is a gift of Eric Lam, and was obtained by transformation with construct Number 4 described by Benfey et al., EMBO J., 8: 2195–2202 (1989).

Growth of Plants

Plants were grown aseptically on agar-solidified MS salts containing 3% sucrose under a 16 h light-8 h dark cycle, illuminated with cool-white fluorescent bulbs (~2000 1x). Plants were propagated by rooting cuttings on the same medium.

For study of tissue-specific expression of GUS, the plants were grown for 10 days in hydroponic cultures containing MS salts without sucrose. Shoots were inserted into a non-transparent lid so that the roots were not exposed to light.

For the light-induction experiments, etiolated seedlings were grown from seed imbibed in gibberellic acid (GA3, 0.5 mg/ml) on agar-solidified MS salts without sucrose in a darkroom. Light induction was carried out by exposing the etiolated seedlings to light provided by cool-white fluorescent bulbs (10,000 1x).

To study arrest of psbA mRNA translation, seeds were germinated on agar-solidified MS salt without sucrose and incubated for 9 days, and were maintained under a 16 h light/8 h dark cycle.

DNA and RNA Gel Blots

Total cellular DNA was extracted by the method of Mettler (1987, supra). Digested DNA was electrophoresed on 0.7% agarose, transferred to nylon membrane (Amersham) using the PosiBlot Transfer apparatus (Stratagene). Probing was performed using Rapid Hybridization Buffer (Amersham) with $^{32}$P-labelled probes generated by random priming (Boehringer Mannheim).

For RNA extraction, tissue was ground with mortar and pestle in liquid nitrogen. RNA isolation and blot hybridization was carried out according to Perisic & Lam, Plant Cell, 4: 831–38 (1992). RNA was separated on 1% agarose-formaldehyde gels. Fold increase in mRNA was quantified by comparison to a dilution series of the most abundant mRNA sample on the blot, exposed so that the signal was in the linear response of the film. Comparison was based on scanning by a Pharmacia LKB Ultrascan XL densitometer.

Immunoblotting

Protein was extracted according to Jefferson et al., EMBO J., 6: 3901–07 (1987). Protein concentrations were determined using the Bio-Rad protein assay reagent kit. For immunoblots, protein extracts were electrophoresed on 10% SDS-PAGE gels (Laemmli, 1970, supra) and transferred to Immobilon-P membrane (Millipore) using a semi-dry transfer apparatus (Integrated Separation Systems). Immunoblot detection used ECL chemiluminescence and 1:10,000 diluted HRP-conjugated secondary antibody (Amersham) Polyclonal rabbit antiserum to *Escherichia coli* $\beta$-glucuronidase was purchased from Clonetech. Prior to probing, GUS antibody was precleared by preincubation with membranes containing protein extracts from non-transformed plants. Polyclonal rabbit antiserum to D1 protein was the generous gift of Lee McIntosh. GUS was quantified on the immunoblots by comparison of experimental samples with the commercial GUS standard and a dilution series. Purified *E. coli* $\beta$-glucuronidase (Type X-A) was purchased from Sigma.

$\beta$-glucuronidase Assays

Histochemical and fluorogenic assays for $\beta$-glucuronidase enzyme activity was carried out according to Jefferson (1988, supra). Substrates 4-methyl-umbelliferyl-glucuronide (MUG), 5-bromo-4-chloro-3-indolyl-glucuronide (X-glu) and product 4-methyl-umbelliferone (MU) were purchased from Jersey Lab Supply.

In vivo Labelling of Proteins and Immunoprecipitation

Seedlings were germinated on agar-solidifed MS salts without sucrose for 9 days under a 16 h light (~2000 1x) and 8 h dark cycle. In vivo labelling in excised cotyledons with [$^{35}$S] methionine was carried out according to Berry et al., Mol. Cell. Biol., 5: 2238–46 (1985). Excised cotyledons were incubated in the light (10,000 1x) or in a darkroom. Manipulations in the dark were carried out under a Kodak #7 green safe light. For pulse-chase experiments, excised cotyledons were labelled with [$^{35}$S] methionine, rinsed in several changes of water and further incubated in a solution of 10 mM non-radioactive methionine in the dark. Protein extraction and immunoprecipitation was carried out according to Berry et al. (1985, supra), except that the extract was centrifuged after the addition of 0.1 ml of the buffer containing 0.75 M NaCl, 50 mM Tris hydrochloride (pH 7.4) 25 mM EDTA, 5% sodium deoxycholate and 0.5% SDS. Immunoprecipitation was from samples containing equal amount of acid-insoluble radioactivity. Lysates were precleared with normal rabbit serum (Amersham). 15 $\mu$l of each antibody were used for immunoprecipitation. Immunocomplexes were separated by 10% SDS-PAGE and subsequently fluorographed with sodium salicylate (Chamberlain, Anal. Bioch., 98: 132–35, 1979).

Results

The PT92 Transplastomic Line

The chimeric uidA gene contains the 224 bp psbA 5'-region including the promoter and leader sequence (Sugita & Sugiura, 1984, supra) and the 393 bp 3'-region required for mRNA stability (Stern & Gruissem, 1987, supra), fused to the coding region of the uidA gene. The chimeric gene was cloned between the trnV gene and ribosomal RNA operon in vector pJS75, to create plasmid pJS80. The PT92 line carrying the chimeric gene was identified in bombarded leaf cultures after selection for the linked spectinomycin resistance marker in donor plasmid pJS80. The chimeric gene is present in both copies of the PT92 inverted repeat region, increasing the size of the 156 kb plastid genome by 5 kb. Duplication of the uidA gene is the result of gene conversion (See Example 1; Staub and Maliga, 1992, supra). The relevant regions of plasmid pJS80 and the PT92 transplastome are shown in FIG. 11.

Figure 11B:
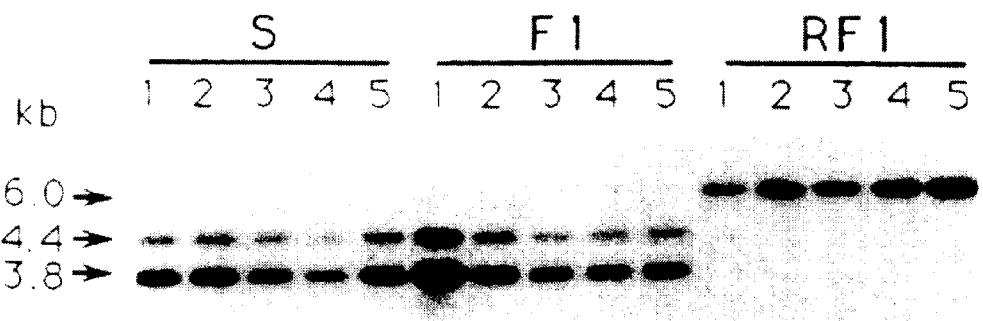

Integration of the uidA gene is stable. Lack of segregation was verified by histochemical staining of seedlings for GUS activity (see below). In the first seed generation, all 1,000 selfed and 1,000 F1 seedlings tested were positive. Likewise, in the second seed generation, all the 500 selfed seedlings tested were positive. The uidA gene is maternally inherited in crosses (FIG. 11*b*).

Histochemical Localization of GUS in Seedlings

Tissue-specific accumulation of GUS was monitored in selfed PT92 seedlings by histochemical staining. Following treatment with X-gluc substrate, PT92 seedling cotyledons have an intense blue color, the hypocotyls are stained weakly, and root tissue is colorless. The histochemical substrate penetrates root tissue effectively as evidenced by the blue color in the seedling that carries a nuclear 35SuidA gene controlled by the cauliflower mosaic virus 35S promoter.

GUS Accumulation is Tissue-specific in Plants

Figure 12A:
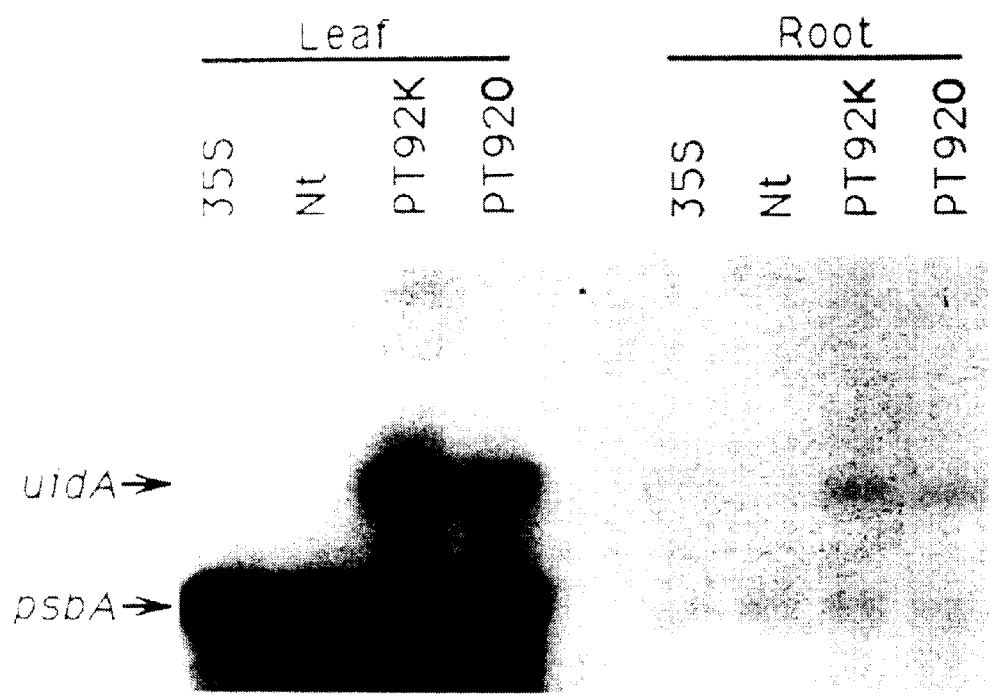
FIGS. 12A–12B—Tissue-specific expression of the plastid uidA gene in plants. Data shown for PT92 subclones (K,O), wild-type tobacco (Nt) and plants transformed with the nuclear 35SuidA gene (35S).

GUS expression was examined in plants from the first seed generation. Plastid uidA and psbA mRNA accumulation was followed by Northern blot analysis (FIG. 12A). PT92 leaf samples contain high steady-state levels of the mRNAs, consistent with the strength of the psbA promoter (Deng & Gruissem, Cell, 49: 379–387, 1988). In roots, both mRNAs accumulate to 300- to 600-fold lower levels than in leaf tissue. The relative amount of mRNAs in roots was determined by comparison with a diluted leaf sample (data not shown). For comparison, uidA mRNA accumulation was examined in roots with a nuclear 35SuidA construct. Note that the mRNA level in roots of the nuclear transformant is 2- to 4-fold less than in the roots of the plastid transformant. Roots of the nuclear transformant stain blue, however, those of the plastid transformant do not.

Figure 12B:
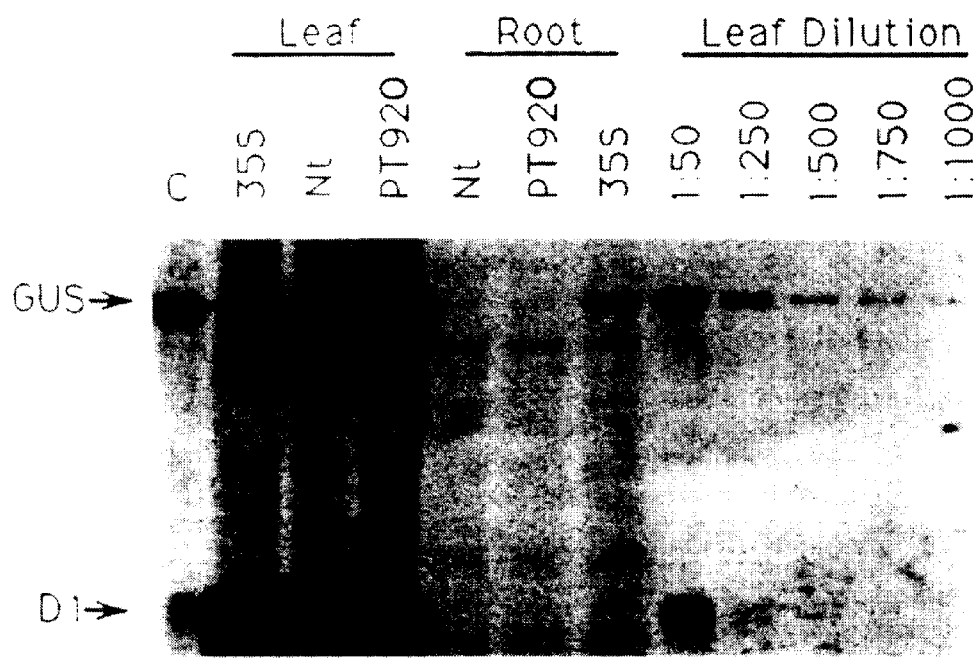

GUS accumulation was followed by immunoblot analysis (FIG. 12B). The antibody did not detect GUS in PT92 roots. In contrast, the PT92 leaf sample accumulates GUS to ~2.5% of total cellular protein. GUS levels were estimated by comparing a dilution series of a leaf extract with a GUS protein standard. In the nuclear transformant, GUS accumulation was significantly lower, ~0.1% of total cellular protein in both leaf and root tissue. The D1 protein, the psbA gene product, also accumulates to detectable levels only in leaves.

GUS Accumulation is Light-inducible in Etiolated Seedlings

Figure 13A:
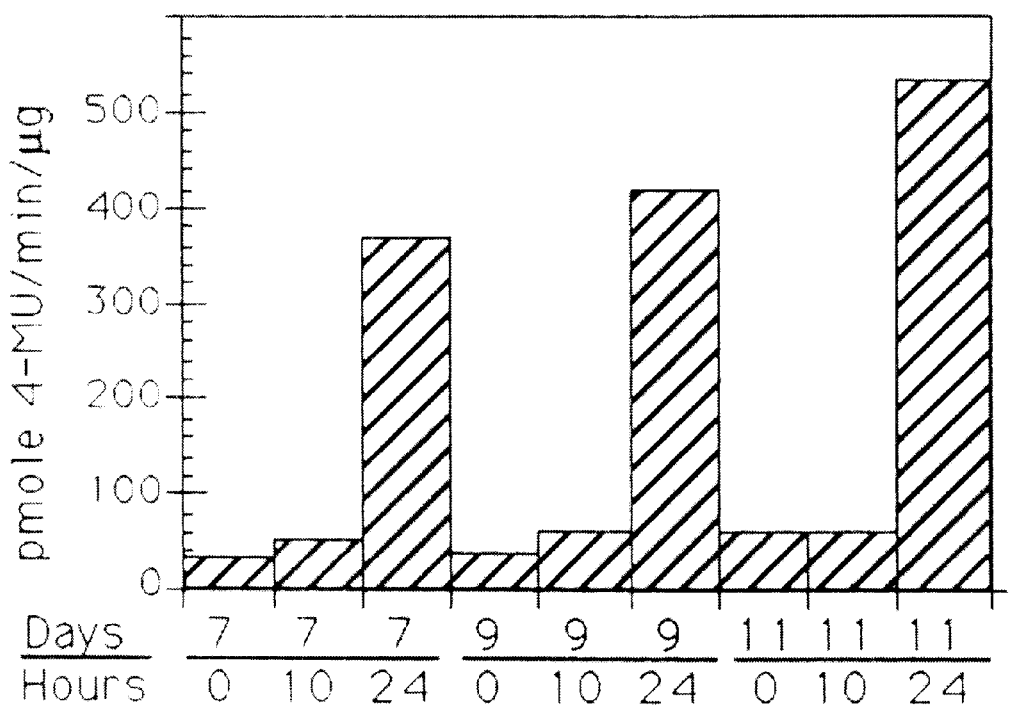
FIGS. 13A–13B—Light-induced expression of uidA in cotyledons of etiolated PT92 seedlings. Samples were prepared from 7-, 9- and 11-day old etiolated seedlings, and from etiolated seedlings that were exposed to light for 10 or 24 h.
Figure 13B:
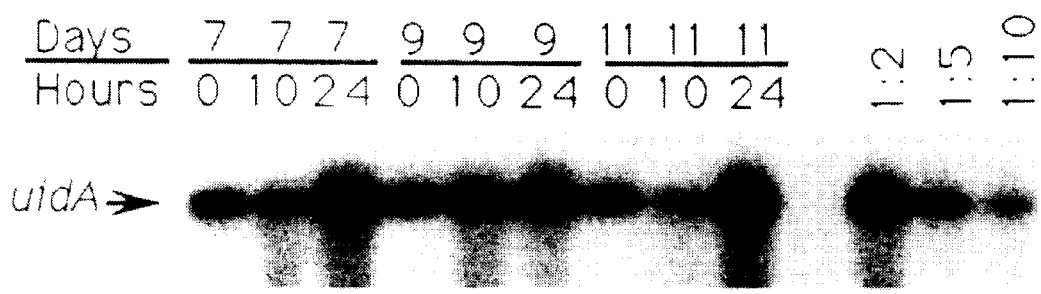

Light induction of GUS and uidA mRNA was studied in 7-, 9- and 11-day old etiolated PT92 seedlings (FIG. 13). In the dark, a low level of GUS activity was detected. This low constitutive level of GUS synthesis resulted in gradual accumulation of GUS over time. In response to light, GUS activity increased ~12-fold during a 24 h period (FIG. 13A), while the increase in the uidA mRNA level was only ~3-fold (FIG. 13B).

Figure 14A:
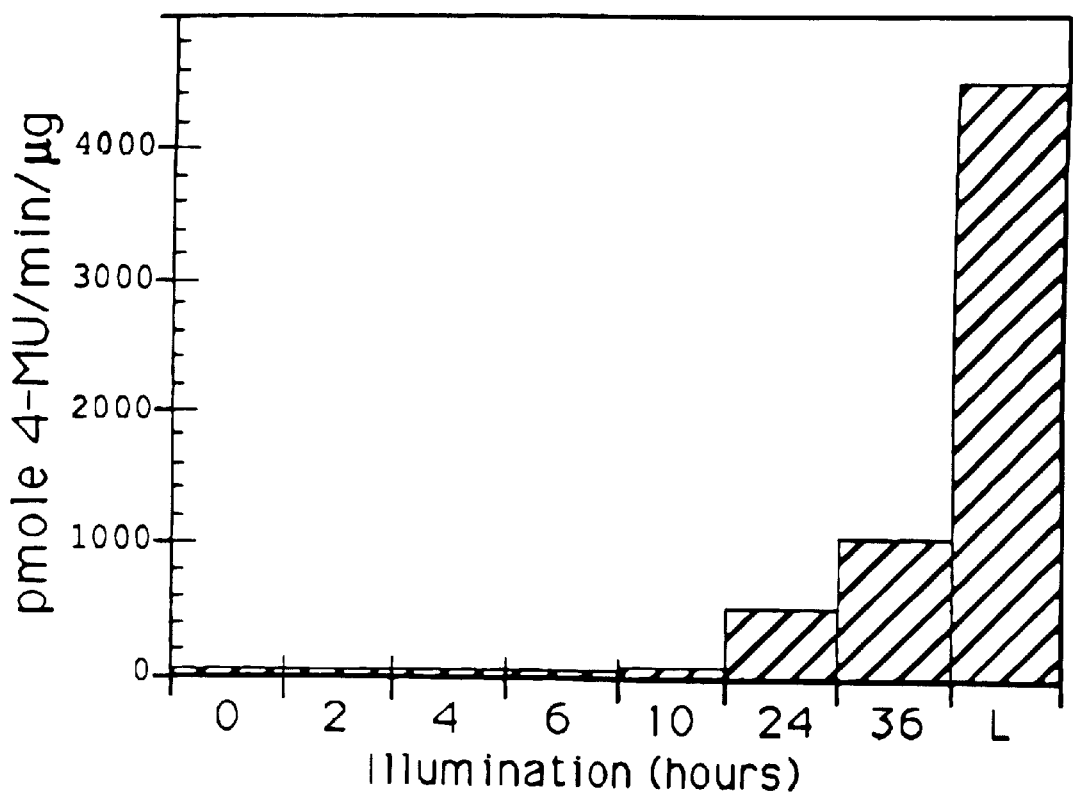
FIGS. 14A–14C—Light-induced expression of uidA and psbA in cotyledons of 9-day old etiolated seedlings. Samples were prepared from light-grown and dark-grown wild-type tobacco (Nt-L, Nt-D), light grown PT92 (PT92-L) or dark-grown (D) PT92 shifted into light (10,000 1×) for the indicated times.

Light-induction of GUS was further studied in 9-day old seedlings illuminated for up to 36 h (FIG. 14A). GUS activity during this time increased 26-fold. This is still below GUS levels in light-grown seedlings, which accumulate GUS to 100-fold higher levels than dark-grown seedlings.

Figure 14B:
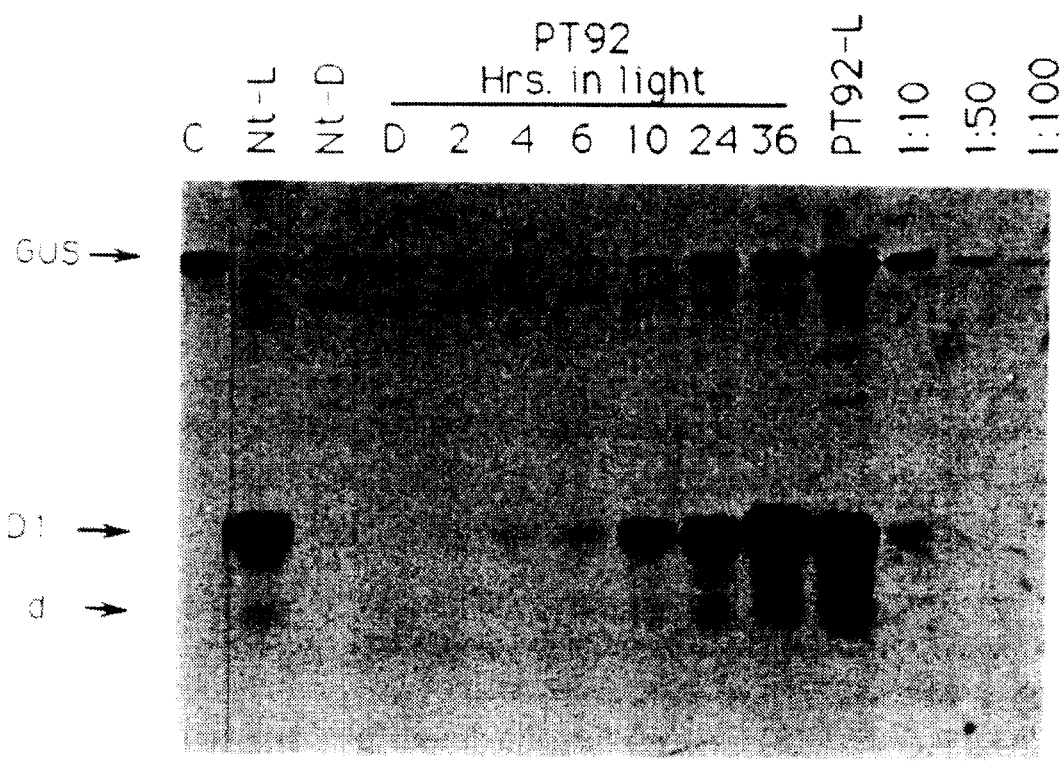

Accumulation of both GUS and the D1 polypeptide was monitored by immunoblot analysis (FIG. 14B). In extracts from dark-grown cotyledons, GUS was barely detectable. Full-length or truncated D1, however, was not detectable. In response to light, accumulation of both proteins is rapidly induced. Interestingly, GUS accumulation lags relative to D1.

Figure 14C:
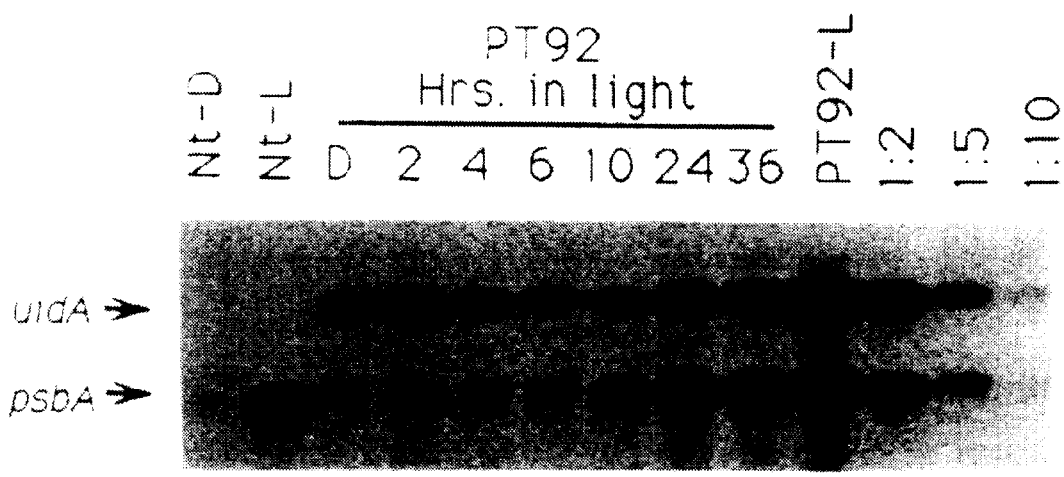

In contrast to the dramatic 26-fold increase in GUS levels in response to light, the uidA mRNA increased only 4-fold after 36 h of illumination (FIG. 14C). Light-grown controls have 100-fold higher GUS activity (FIG. 14A), but only 7-fold higher mRNA levels (FIG. 14C) than dark-grown controls. In response to light, psbA mRNA increased 10-fold above dark levels, with D1 accumulating from undetectable to high levels.

Translation of uidA mRNA is Arrested in Seedlings Upon Transfer to Dark

Figure 15A:
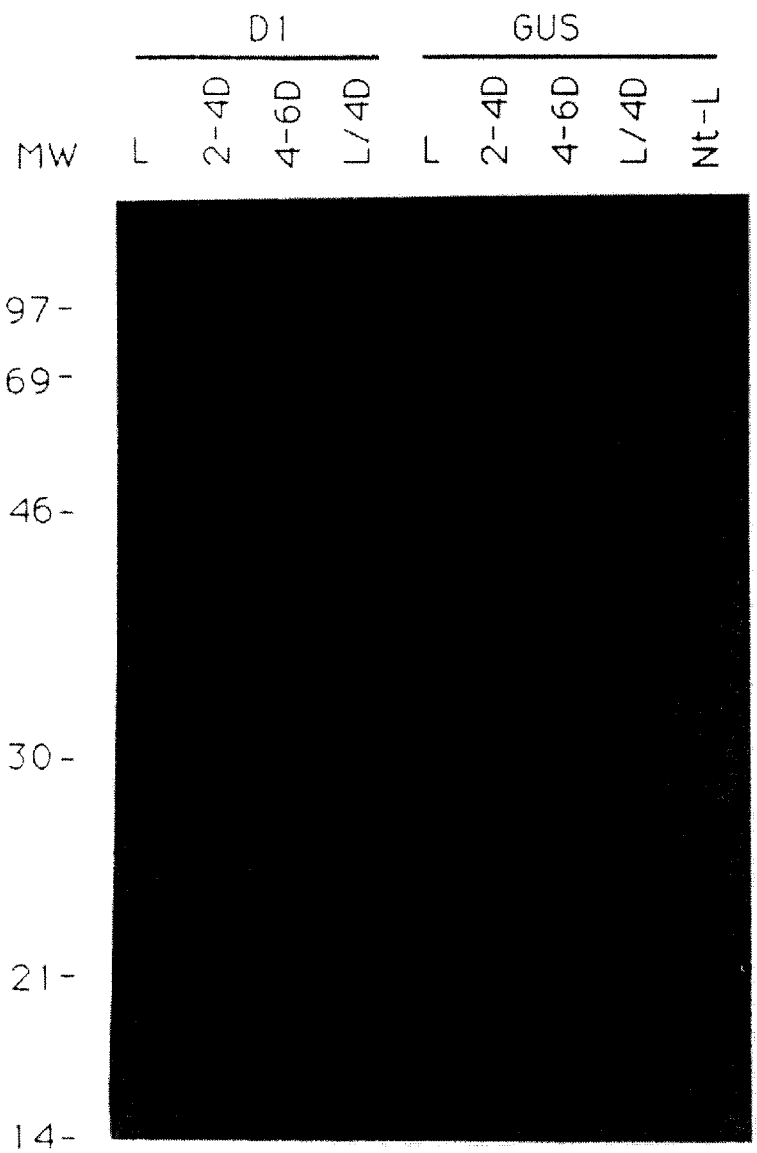
FIGS. 15A–15B—Arrest of uidA and psbA mRNA translation in the dark. Experiments were carried out with cotyledons of 9-day old PT92 seedlings.

Arrest of psbA mRNA translation upon transfer of light-grown plants to the dark has been explained by premature termination of elongation, and subsequent degradation of termination of elongation, and subsequent degradation of truncated D1 polypeptides. We have confirmed the arrest of psbA mRNA translation upon transfer to the dark in tobacco seedlings (FIG. 15). After tranfer of light-grown seedings to the dark for 2 h, pulse-labelling with [$^{35}$S] methionine and immunoprecipitation with D1 antiserum yielded no radioactive protein species. In contrast, D1 was rapidly synthesized in the light during the 2 h pulse. Furthermore, radioactive D1 protein synthesized in the light was stable during a 4 h chase in the dark. Under our experimental conditions, no truncated D1 polypeptide was detected by the D1 antibody in samples from light- or dark-grown plants.

Synthesis of GUS was studied in the same pulse-labelled samples using GUS antiserum for immunoprecipitation (FIG. 15). As for D1, GUS was synthesized in the light, but not in the dark. Also, GUS that had been labelled in the light was stable during the 4 h chase in the dark. Note the lower radioactivity of GUS relative to D1 that may indicate a slower rate of synthesis.

Figure 15B:
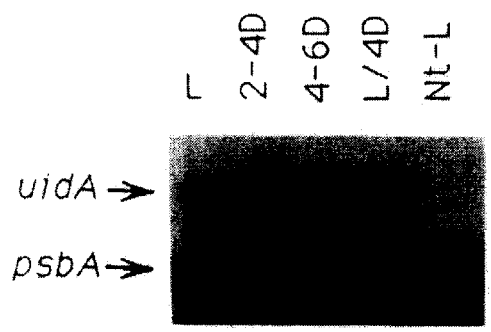

The mRNAs for both psbA and uidA were readily detectable and their level did not decrease in the dark (FIG. 15B). Presence of uidA mRNA in both light- and dark-labelled samples, with no detectable GUS synthesis in the dark, confirms the arrest of uidA mRNA translation in the dark.

Discussion

Expression of the uidA coding region, under control of the psbA 5'- and 3'-regulatory regions, followed the pattern of the endogenous psbA gene. First, while the uidA mRNA was present in all tissues, accumulation of the encoded GUS polypeptide to high levels was dependent on tissue type. A particularly dramatic example of tissue specificity is the lack of GUS in PT92 roots demonstrated by histochemical staining and immunoblot analysis (FIG. 12). Note that PT92 roots accumulate the uidA mRNA at levels that are 2–4 times higher than in plants with the nuclear 35SuidA gene in which GUS is readily detectable. Second, the 100-fold induction by light of GUS in seedling cotyledons cannot be accounted for by the ~7-fold increase in mRNA levels (FIG. 14). This reflects a more efficient utilization of the uidA mRNA template in light, as established for the psbA mRNA by Klein et al., J. Cell Biol., 106: 289–301 (1988). Third, transfer of cotyledons from light to dark resulted in the arrest of uidA mRNA translation, as is the case for D1 (FIG. 15).

These data collectively reinforce the conclusion that characteristic tissue-specific and light-regulated accumulation of D1 has been conferred to GUS, the chimeric uidA gene product, via the cis-acting regulatory elements contained within the psbA leader and trailer sequences. Furthermore, the primary control of GUS and therefore D1 translation is at the level of initiation. The control of translation initiation is somewhat leaky, as evidenced by the slow accumulation of GUS over time in dark-grown seedlings (FIG. 13). We assume that translation of psbA mRNA is also initiated in the dark at comparably low levels. This small amount of polypeptide was not detected either because it may be subject to cotranslational control, as proposed for barley, or because full-length D1 is degraded in the absence of other components of PSII. The stability of GUS in plants, with a half-life of ~50 h (Jefferson et al., 1987, supra), facilitated its detection in the dark.

In barley, translation of the D1 polypeptide is initiated constitutively and the accumulation is controlled at the level of translational elongation. It is possible therefore that psbA regulation in barley and tobacco are different. There are significant differences in the regulation of plastid photosynthetic gene expression between dicots (tobacco) and monocots (barley). In the dark, for example, the plastome-encoded rbcL mRNA is translated in barley, a monocot (Klein and Mullet, J. Biol. Chem., 261: 11138–45, 1986), but not in amaranth, a dicot (Berry et al., Plant Cell, 2: 795–803, 1990). Alternatively, differences of psbA expression in barley and tobacco may be due to the different developmental stage of tissues used. In barley, experiments were carried out in primary leaves of dark-grown seedlings. Tobacco seedings do not develop primary leaves in the dark. Our studies on light-induction therefore were carried out using seedling cotyledons.

The transgenic approach has made feasible direct confirmation of translation initiation in tobacco as the primary mechanism regulating accumulation of D1 polypeptide via the untranslated region of psbA mRNA. Furthermore, incorporation of uidA into the plastid genome resulted in accumulation of GUS in leaves to a high level–2.5% of total cellular protein, confirming the potential of the plastid compartment for the production of foreign polypeptides.

EXAMPLE 5
Deletion of the rbcL Gene from the Tobacco Plastid Genome and Relocation of the rbcL Gene to the Nucleus This Example provides a demonstration of effective deletion of a key gene of the plastid genome, using vectors and methods of the invention.

Materials and Methods

Abbreviations used in this Example include ptDNA, plastid DNA; Rubisco, ribulose-1,5, bisphosphate carboxylase; SSU and LSU, Rubisco small and large subunits, respectively.
Plasmid Construction Plasmid pIK30 is a pBluescript KS(+) phagemid vector (Stratagene) that carries a tobacco PvuII/XhoI ptDNA fragment (nucleotides 55,147–60,484 in Shinozaki et al.) with most of the rbcL coding region deleted as a SacII/NruI fragment and replaced with a chimeric aadA gene as a 1.3-kb SacI-PstI fragment. Chimeric aadA is identical with the aadA gene in plasmid pZS197 (Example 2) and pPRV (Example 6) except that it has the first 5 amino acids of the tobacco LSU fused at its N terminus.

Plasmid pIK67 carries the NrbcL gene in the pBI121 Agrobacterium binary vector (Jefferson et al., EMBO J., 6: 3901–07, 1987). The NrbcL chimeric gene has the rbcL coding region cloned as an NcoI/XbaI fragment in the cauliflower mosaic virus 35S cassette in plasmid pFF19 (Timmermans et al., J. Biotechnol., 14: 333–44, 1990). The NcoI site includes the rbcL translational initiation codon and was created by oligonucleotide-directed mutagenesis, as described in the Examples above. The XbaI site was created by linker ligation into the AccI site 6 bp downstream of the rbcL stop codon.

Plasmid pIK66 carries the TParbcL gene in the pBI121 Agrobacterium binary vector (Jefferson et al., 1987, supra). The TParbcL chimeric gene is identical with NrbcL except, that the pea SSU transit peptide and 5 amino acids of the mature SSU are translationally fused with the rbcL coding region. Translational fusion was obtained by cloning a 232-bp HindIII/NcoI fragment, containing the pea SSU transit peptide, into the NrbcL gene. The fragment was obtained from a derivative of the pea rbcS SS15 cDNA clone (Corruzzi et al., J. Biol. Chem., 258: 1399–1402, 1983) in which an NcoI site was created by oligonucleotide-directed mutagenesis 9 bp downstream of the transit peptide processing site. In TParbcL the DNA fragment containing the transit peptide is linked to the rbcL coding region via the newly created NcoI site.
Transformation and Regeneration of Transgenic Plants Tobacco (*N. tabacum*) plants were grown, and transformation performed, according to methods described in the Examples above. Spectinomycin-resistant calli and shoots were selected on RMOP medium containing 500 μg of spectinomycin dihydrochloride per ml, as described above. Nuclear gene transformants were selected by resistance to kanamycin monosulfate (50 μg/ml) on RMOP medium by the Agrobacterium leaf disk transformation protocol of Horsch et al., Science, 227: 1229–31 (1985).
DNA Gel-Blot Analysis of Total Cellular DNA Total cellular DNA was digested with the appropriate restriction enzymes, electrophoresed on 0.7% agarose gels, and transferred to nylon membrane (Amersham) using the PosiBlot transfer apparatus (Stratagene). Blots were probed with rapid hybridization buffer (Amersham) with $^{32}$P-labelled probes generated by random priming (Boehringer Mannheim).
Immunoblotting As described above, leaf protein extracts (2 μg) were isolated and resolved in SDS/10% polyacrylamide gels and immunoblotted with rabbit polyclonal antibody raised against spinach LSU and SSU proteins (dilutions, 1:2,000 and 1:1,000, respectively) using the ECL (enchanced chemiluminescence) detection system (Amersham).
Determination of Rubisco Activity For determination of Rubisco activity, the plants were illuminated with high light (850–1000 $\mu Em^{-2}S^{-1}$) for 1 h. Leaf discs (2.23 $cm^2$) were frozen in liquid $N_2$ and homogenized in 1 ml of 50 mM $NaHCO_3$/5 mM $MgCl_2$/1 mM EDTA/5 mM dithiothreitol/10% (vol/vol) glycerol/0.01% Triton X-100. Cell debris in the homogenate was sedimented in a microcentrifuge (2 min). Total (fully activated) Rubisco activity was measured by $^{14}CO_2$ incorporation in 50 μl of the supernatant after preincubation for 30 min at 4° C. with 20 mM $MgCl_2$ and 10 mM $NaHCO_3$ (Quick et al., Planta, 183: 542–54, 1991).
Testing by Seedling Phenotypes Seedling phenotype was determined by plating surface-sterilized seeds on MS salts containing 3% sucrose. Plastid transformants carrying the chimeric aadA gene are resistant to spectinomycin and streptomycin (500 μg/ml each). Seedlings transformed with vector pIK66, a derivative of pBI121, are resistant to kanamycin monosulfate (300 μg/ml) due to expression of a chimeric kan gene in the nucleus. Seedlings resistant to the drugs are green, whereas those sensitive to the drugs are white on the selective medium.

Results

Deletion of the rbcL Gene from the Plastid Genome

The rbcL coding region was deleted from the tobacco plastid genome by targeted insertion of the selectable aadA gene. Insertion vector pIK30 was prepared by cloning aadA into a ptDNA fragment to replace the coding region of rbcL.

The pIK30 plasmid DNA was introduced into plastids by the biolistic protocol. Replacement of rbcL by aadA via flanking ptDNA sequences and selective amplification on spectinomycin medium yielded a uniformly altered population of ptDNA copies. The absence of wild-type ptDNA copies in these plants was verified by DNA gel blot analysis. Plants with rbcL deleted plastid genomes ("NtΔrbcL") lack immunologically detectable Rubisco subunits and therefore are photosynthetically incompetent. These plants can be maintained on sucrose-containing medium on which they are pale green. The pale-green phenotype is stable in the absence of spectinomycin selection, indicating the complete absence of wild-type ptDNA copies.

Nuclear rbcL Genes

To test whether photosynthetic competence of the NtΔrbcL plants could be restored by rbcL expressed from the nucleus, a nuclear rbcL gene, TParbcL, was constructed. TParbcL encodes the tobacco LSU fused at its N-terminus with the pea SSU transit peptide (TPaLSU) to enable import of the chimeric protein into chloroplasts (Gatenby et al., EMBO J., 7: 1307–14, 1988). The processed form of TPaLSU, the aLSU peptide, can be distinguished from the wild-type plastid LSU since it carries the 5 N-terminal amino acids of the mature pea SSU. In vector pIK66, TParbcL is expressed from a constitutive cauliflower mosaic virus 35S cassette.

As a control, a second nuclear rbcL gene, NrbcL, was constructed lacking the pea SSU transit peptide (pIK67). In the absence of a plastid-targeting transit peptide, no complementation of NtΔrbcL plants was expected with this construct.

Complementation of the Defective Plastids by the Nuclear rbcL Gene

The nuclear rbcL genes were introduced into the defective NtΔrbcL plants by selection for the linked kan gene encoding kanamycin resistance.

Transformation with the TParbcL construct yielded green plants in 27 independent kanamycin-resistant clones, indicating complementation of the NtΔrbcL plastids. Rubisco was quantified in green leaves of complemented plants by immunoblot analysis. Of 12 clones examined, 8 accumulate detectable levels of Rubisco subunits: 5 clones contain ≈10% and 3 clones contain ≈1% of the wild-type level. Intraplastidic localization of Rubisco was confirmed by immunoblot analysis of protein extracts from isolated chloroplasts. As expected, the LSU and SSU polypeptides accumulate in stoichiometric amounts, since unassembled SSU is rapidly degraded (Schmidt & Mishkind, Proc. Natl. Acad. Sci. USA, 80: 2632–36, 1983).

Total Rubisco activity was determined in leaf disks from five independently transformed lines. Rubisco activity was 3.4%, 3.0%, and 2.9% of the wild-type level (43 $\mu$mol.m$^{-2}$.S$^{-1}$) in lines 5, 8 and 10, respectively. No Rubisco activity was detected in the nontransformed NtΔrbcL-1 leaves or in clones 6 and 9, which had no immunologically detectable levels of Rubisco. The green pigmentation of plants such as clones 6 and 9 is less intense and is probably due to low levels of Rubisco accumulation caused by the chromosomal position of the TParbcL transgenes (Weising et al., Ann. Rev. Genet., 22: 421–77, 1988).

Complemented plants with ≈3% Rubisco activity were able to grow slowly in the greenhouse in low light (250 μE). Faster growth was observed when the shoots were grafted onto wild-type root stock, but growth was still limited by low Rubisco activities. The greenhouse-grown plants are pale green, unlike those grown on sucrose medium, which are indistinguishable from wild-type.

No complementation of NtΔrbcL plants was obtained with the NrbcL gene that lacks the transmit peptide, as expected (95 independently transformed lines tested).

Inheritance of the Drug-resistance Phenotypes in the Seed Progeny

Mendelian inheritance of the nuclear TParbcL and kan genes and maternal inheritance of the plastid aadA gene is expected due to the subcellular compartmentalization of these chimeric transgenes. Seedling phenotypes shown in Table 6 indicate that this is indeed the case.

TABLE 6

Inheritance of Antibiotic Resistance in the Nt-pIK66-8 Line, a Derivative of the NtΔrbcL Transplastomic Line Complemented with the Nuclear TParbcL Gene

| Progeny | No antibiotic, G/PG | Kan300, R/S | Sp500/Sm500, R/S |
|---|---|---|---|
| Selfs | 61:20 (3:1) | 60:18 (3:1) | 99:0 (1:0) |
| F$_1$ | 48:46 (1:1) | 52:49 (1:1) | 88:0 (1:0) |
| RF$_1$ | 87:0 (1:0) | 47:51 (1:1) | 0:92 (0:1) |

The ratios of green (G) to pale-green (PG) and resistant (R) to sensitive (S) seedlings and the expected ratios (in parentheses) are given. Selfs, selfed seed progeny; F$_1$, seedlings from crossing transgenic as female and wild-type as male; RF$_1$, reciprocal cross in which wild-type is female and transgenic is pollen parent. Kan300, 300 μg of kanamycin monosulfate per ml; Sp500/Sm500, spectinomycin (500 μg/ml) and streptomycin (500 μg/ml) in MS medium containing 3% sucrose.

Furthermore, if complementation (green phenotype) is due to expression of the introduced nuclear TParbcL gene, its cosegregation with the linked kan gene is expected in the seed progeny. Cosegregation analysis has been carried out in a segregating population of seedlings germinated on drug-free medium by subsequently culturing them on a selective kanamycin (100 μg/ml). In each case, the complemented (green) phenotype on the drug-free medium was associated with kanamycin resistance in the subsequent test, whereas lack of complementation (pale-green color) on the first medium was associated with kanamycin sensitivity (46 and 48 seedlings tested, respectively).

The foregoing results demonstrate that a gene may be deleted from the plastid genome using the constructs and methods of the present invention. If desired, the gene may be added back to the nuclear genome for expression in the cytoplasm and translocation to the chloroplast.

EXAMPLE 6 pPRV Family of Targeted Transformation/Expression Vectors for the Inverted Repeat Region of the Plastid Genome This Example describes an *E. coli* pUC119 plasmid derivative, pPRV1, which forms the backbone of a plastid repeat transforming vector family. This plasmid carries a ptDNA fragment from the inverted repeat region of the plastid genome. The pPRV1 plasmid was developed into a family of versatile plastid vectors by the addition of two important components: (i) selectable spectinomycin resistance (aadA) genes for highly efficient recovery of plastid transformants and (ii) a multiple cloning site (MCS) to facilitate the introduction of linked passenger genes. The pPRV series are designed specifically for efficient gene delivery to plastids of higher plants, or for any organelle genome.

Materials and Methods

Vector Construction

Plasmid pPRv1 is based on a pUC119 plasmid derivative, pZS192, in which the ScaI site in the ampicillin resistance gene has been removed by oligonucleotide-directed mutagenesis (5-AGTACT-3' changed to 5'-AGTATT-3). The 2.9-kb EcoRI/BglII ptDNA fragment from pJS75 (Staub & Maliga, 1992, supra) was cloned into plasmid pZS192 digested with the EcoRI/BamHI restriction endonucleases. The EcoRI and BglII restriction sites in the tobacco ptDNA are at nucleotide positions 138,447 and 141,382, respectively (Shinozaki et al.) The spectinomycin-resistance mutation in the 16S rRNA gene was removed by replacing the EcoRI/ApaI fragment in the 2.9-kb EcoRI/BglII clone with the cognate wild-type ptDNA fragment. The EcoRI-site at one end of the ptDNA fragment was removed by digestion with EcoRI and filling-in the single-stranded overhangs. The BglII site at the other end was removed by ligating the BglII and BamHI sites. Subsequently, all remaining pUC119 cloning sites were removed by digestion with XbaI and HindIII and filling-in. For convenience, the DraI site in plasmid pJS75 was converted to a StuI restriction site by linker ligation (5'-CGAGGCCTCG-3'; Sequence I.D. No. 40).

Plasmids pPRV100A and pPRV100B were obtained by ligating the multiple cloning site (MCS) as a synthetic double-stranded oligonucleotide into the ScaI site of pPRV1. The oligonucleotide was obtained by annealing the 5'-AAGCTTGCATGCCTGCAGGTCGACTCTAGAGGAT CCCCGGGTACCGAGCTCGAATTC-3' (Sequence I.D. No. 41) sequence with its complementary strand, designed after the MCS in plasmid pUC18 (Yanisch-Perron et al., Gene 33: 103–19, 1985). The linker was ligated in both (A,B) orientations: The Eco RI site is proximal to the trnV gene in derivatives with the A orientation.

Selectable markers in the pPRV family are aadA genes expressed in different cassettes. The psbA-5'/psbA-3' cassette is a truncated derivative of the psbA cassette described in Example 4. The 5'-regulatory region includes nucleotides 1735 through 1596; the 3-region includes nucleotides 533 through 345 of the tobacco ptDNA (Shinozaki et al.) The Prrn-5'/rps16-3' cassette has the Prrn-5' region described in Examples 2 and 3, and the 3'-regulatory region of the rps16 ribosomal protein gene between nucleotides 5087 and 4939 of the tobacco ptDNA (Shinozaki et al.). The rps16-5'/rps16-3' cassette utilizes the expression signals of the rps16 plastid ribosomal protein gene. The rps16-5' regulatory region includes sequences between nucleotides 6656–6214; the 3' regulatory region contains sequences between nucleotides 5087 and 4939 of the tobacco ptDNA (Shinozaki et al.). Restriction sites within and adjacent to the cassettes were eliminated during plasmid construction. Subsequently, the oligonucleotide containing the pUC18 MCS was ligated next to the aadA gene. The expression cassettes are described in more detail in Example 7 herein.

To test transplastome stability, two constitutive expression cassettes were prepared. In plasmid pZS208, the N-terminus of the aadA coding region is translationally fused with the 5 N-terminal amino acids of the Rubisco large subunit, as decribed for kan in Example 3; the psbA 3'-region is derived from plasmid pJS25 (see Example 45). In plasmid pZS209, aadA is expressed from a chimeric trnV promoter. To ensure translation of the mRNA, a synthetic ribosome binding site was fused transcriptionally with the promoter fragment, as described for the Prrn promoter in Examples 2 and 3. Chimeric promoter sequences are included in the Results. The aadA mRNA was stabilized with the psbA 3'-region from plasmid pJS25.

Construction of a Chimeric uidA Reporter Gene

The light-regulated promoter (LRP) of the psbD operon (Christopher et al., Plant Cell 4: 785–89, 1992) was amplified from the tobacco ptDNA to include sequences from nucleotide 33,477 to 33,583, flanked by engineered SacI (5') and XbaI (3') restriction sites. The primers used in the PCR are 5'-CCAAGAGCTCCGAAAGGTTAGAAATCAAC-3' (Sequence I.D. No. 42) and 5'-CGATAGAGATGAAA TTGGAGCTCTAGACGG-3' (Sequence I.D. No. 43). This construct was cloned as a SacI/XbaI fragment upstream of a uidA gene with the following leader sequence: 5'-<u>GAGCTC</u> TAGAATTCAGTTGTAGGGAGGGAT<u>CCATGG</u>-3' (Sequence I.D. No. 44; XbaI/NcoI sites underlined). The translational initiation codon of uidA is included within an NcoI site (Example 4). This site was used to link the leader sequence to the uidA coding region. To stabilize the mRNA, the rps16-3'-region (above) was cloned downstream of the uidA coding region utilizing the appropriate XbaI restriction site (Example 5). This construct was cloned into pPRV111A and pPRV111B vectors for insertion into the ptDNA (below).

Production of Transplastomic Lines

Tobacco (N. tabacum) plants were grown aseptically on agar-solidified medium containing MS salts and sucrose (30 g/L), as described in Examples 1–5 above. For plastid transformation, the DNA was introduced on the surface of microscopic tungsten particles using the DuPont PDS1000He Biolistic gun, as described in the Examples above. Spectinomycin resistant calli and shoots were selected on RMOP medium containing 500 mg/mL of spectinomycin dihydrochloride. Resistant shoots were regenerated on the same selective medium, and rooted on MS agar medium, as described in the Examples above.

DNA and RNA Gel Blot Analysis

Total cellular DNA was digested with the appropriate restriction enzymes, electrophoresed on 0.7% agarose gels and transferred to nylon membrane (Amersham) using the PosiBlot Transfer apparatus (Stratagene), as described above. Blots were probed using Rapid Hybridization Buffer (Amersham) with 32P labeled probes generated by random priming (Boehringer-Mannheim).

RNA was extracted from frozen leaf tissue with the TRIzol Reagent (BRL) following the manufacturer's protocol. For Northern analysis 3 mg of total RNA was separated on a 1% agarose-formaldehyde gel and transferred to nylon membrane as above. Labeling of DNA for hybridization, and probing was carried out as described for DNA gel blots (above). Membranes were stripped in boiling 0.1% SDS prior to reprobing.

Testing of Seedling Phenotypes

Seedling phenotypes were determined by plating surface-sterilized seeds on MS salt medium with or without spectinomycin dihydrochloride (500 mg/mL), as described in the Examples above.

Results

Plastid Targeting Fragment

The original plastid transformation vector, pJS75, contains a mutant 16S rRNA gene conferring spectinomycin reistance, as well as a number of restriction sites engineered into the targeting DNA. Integration of a 6.2-kb ptDNA fragment from pJS75 into the plastid genome was monitored using the engineered RFLPs of pJS75. Some of the novel restriction sites were engineered in intergenic regions, so that the sites could be used for targeted insertion of heterologous DNA. Plasmid pPRV1 carries a 2.9-kb EcoRI/BglII ptDNA fragment from pJS75 with a unique StuI-site between trnV and the ribosomal RNA (rrn) operon, and a unique Sca I-site between trnV and the rps7/12 operon. The DNA sequence of the engineered ptDNA fragment in plasmid pPRV1 is shown in FIG. 16. The ScaI cloning site is in an open reading frame (ORF131); ligation of the decameric ScaI linker into the HincII-site (Staub & Maliga, 1992, supra) altered the frame of this ORF. Linker ligation in the HincII site separated the last two nucleotides of the TGA stop codon of ORF70B, which overlaps with ORF131, and is located on the opposite DNA strand. However, a new in-frame TAA stop codon was created by flanking the ScaI linker with appropriate nucleotides (FIG. 16). In pPRV1, both restriction sites are flanked by more than 1 kb of ptDNA targeting segment.

Figure 17A:
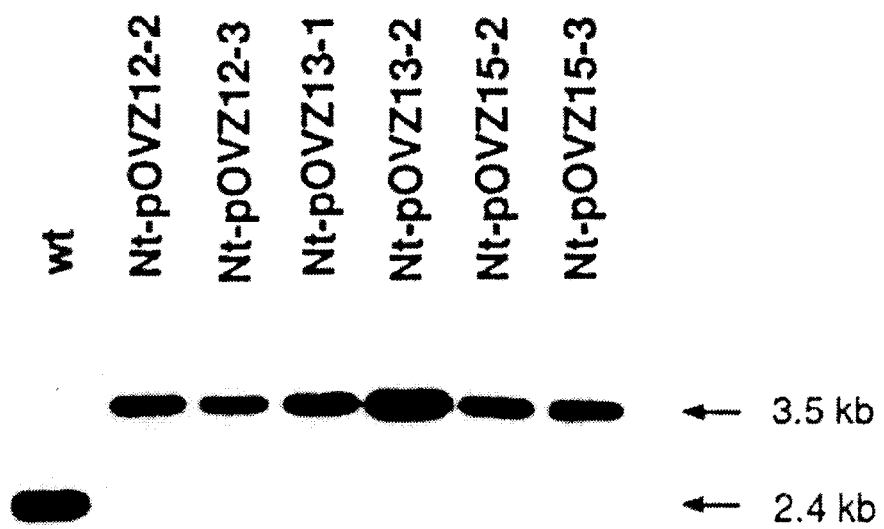
(FIG. 17A) the 3.5-kb EcoRI/EcoRV ptDNA fragment that is part of the EcoRI/BglII targeting fragment (P1), and (FIG. 17B) the 0.8-kb aadA coding region (P2).
Figure 17B:
Figure 17C:
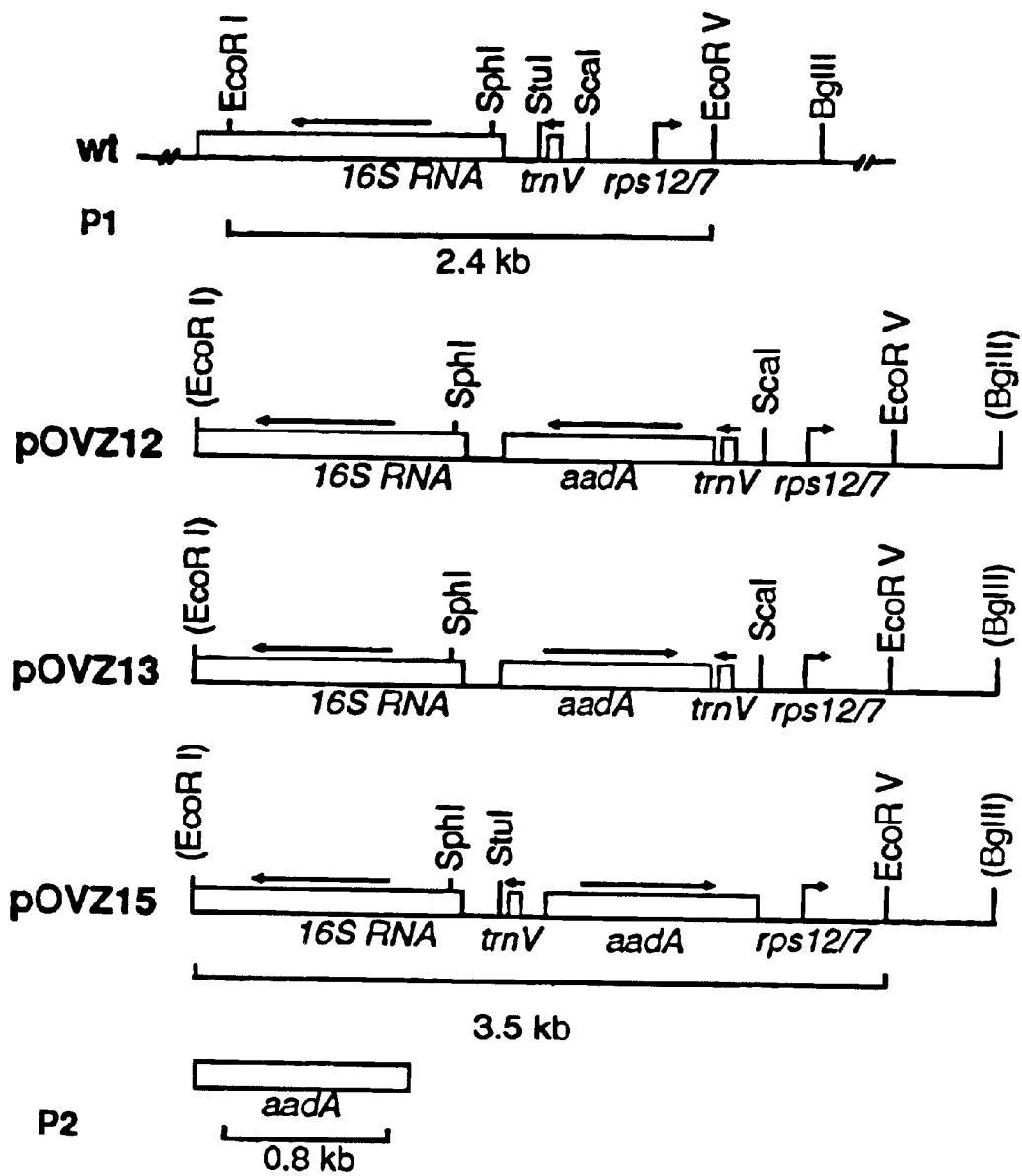
(FIG. 17C): Map of the ptDNA region containing the pPRV targeting fragment (wt), and of plasmids pOVZ12, pOVZ13 and pOVZ15, progenitors of the pPRV vectors. The P1 targeting sequences hybridize to a 2.4-kb fragment in the recipient plants and a larger, 3.5-kb fragment in the transplastomic lines. The aadA probe, P2, hybridizes only to the larger transplastomic fragment. The EcoRI site is blunted in the pOVZ plasmids, and the predicted size 3.5-kb fragment is obtained only if aadA has integrated in the ptDNA via flanking homologous sequences. Abbreviations: 16SrRNA, trnv, rps12/7 are plastid genes; EcoRI, SphI, StuI, ScaI, EcoRV and BglII mark restriction endonuclease cleavage sites. Arrows mark the direction of transcription.

As described in Example 2, a chimeric aadA gene was ~100 times more efficient for selection of plastid transformants than the spectinomycin-resistant 16S rRNA gene in pJS75. Therefore, the region of the 2.9-kb fragment containing the 16S rRNA spectinomycin resistance gene was replaced with the spectinomycin-sensitive allele to yield plasmid pPRV1. Subsequently, an aadA gene was ligated into the unique StuI or ScaI sites to yield plasmids pOVZ12 and pOVZ13, or pOVZ15, respectively (FIG. 17C). The aadA coding region in these plasmids is expressed from the truncated psbA-5'/psbA-3' cassette. The plasmids were then tested in plastid transformation experiments.

Plastid Transformation With the pOVZ Plasmids

To test the efficiency of plastid transformation with plasmids pOVZ12, pOVZ13 and pOVZ15, microscopic tungsten particles were coated with the plasmid DNAs, introduced into tobacco leaves by the biolistic process and the bombarded leaves were cultured on selective spectinomycin medium. With each of the constructs, on average, one plastid transformant was obtained per bombardment (data not shown). This frequency is comparable to that obtained with the previously tested chimeric aadA gene of Example 2.

Leaves were taken from shoots developing on the spectinomycin medium and inoculated onto the same selective spectinomycin medium for a second cycle of plant regeneration. After transformation with the aadA gene, about half of the plants obtained during the second regeneration cycle are expected to have a uniform population of transplastomes. Indeed, homoplasmic plastid transformants with the pOVZ plasmids were obtained without difficulty (FIG. 17).

The transplastomic pOVZ tobacco plants were transferred to the greenhouse where they were grown in soil, in the absence of spectinomycin selection. Seeds were collected after self pollination, and after crossing with the wild-type parental plants. The seeds were germinated on a selective spectinomycin medium to determine whether maintenance of the plants under non-selective conditions resulted in the elimination of the transplastomic aadA gene, and therefore the loss of spectinomycin resistance.

Data on seed transmission of the transplastomic spectinomycin resistance trait are summarized in Table 7. Uniform resistance to spectinomycin in the selfed seed progeny, and in the cross with the transplastomic plants as the female parent, indicated that the transplastomic aadA marker is stable. Lack of pollen transmission of spectinomycin resistance in the reciprocal cross, using the wild-type non-transformed parent as female and the transplastomic as pollen parent, was expected since plastids are not transmitted via pollen in tobacco.

TABLE 7

The Chimeric aadA Gene is Stable in the Plastid Genome of the Seed Progeny

| Line[a] | Progeny[b] | No drug[c] | | Sp500[d] | |
|---|---|---|---|---|---|
| | | Green | White | Green | White |
| Nt-pOVZ12-2 | Self | 816 | 0 | 920 | 0 |
| | F1 | 880 | 0 | 736 | 0 |
| | RF1 | 544 | 0 | 0 | 768 |
| Nt-pOVZ12-3 | Self | 960 | 0 | 640 | 0 |
| | F1 | 856 | 0 | 448 | 0 |
| | RF1 | 732 | 0 | 0 | 620 |
| Nt-pOVZ13-1 | Self | 680 | 0 | 512 | 0 |
| | F1 | 840 | 0 | 776 | 0 |
| | RF1 | 200 | 0 | 0 | 280 |
| Nt-pOVZ13-2 | Self | 560 | 0 | 544 | 0 |
| | F1 | 576 | 0 | 432 | 0 |
| | RF1 | 584 | 0 | 0 | 208 |
| Nt-pOVZ15-2 | Self | 960 | 0 | 720 | 0 |
| | F1 | 704 | 0 | 784 | 0 |
| | RF1 | 736 | 0 | 0 | 520 |
| Nt-pOVZ15-3 | Self | 744 | 0 | 488 | 0 |
| | F1 | 552 | 0 | 680 | 0 |
| | RF1 | 760 | 0 | 0 | 800 |

[a]Nt and the plasmid name indicates, with which plasmid the transplastomic line was obtained; the number added after the hyphen identifies an independently transformed line. For example, transplastomic tobacco line Nt-pOVZ12-2 was obtained by transformation with plasmid pOVZ12, and this is line No. 2.
[b]F1, cross in which resistant is female; RF1, cross in which resistant is pollen parent.
[c]No spectinomycin in the germination medium.
[d]Spectinomycin dihydrochloride at 500 μg/ml in the germination medium.

Testing Stability of Transplastomes With Short Direct Repeats

Figure 18A:
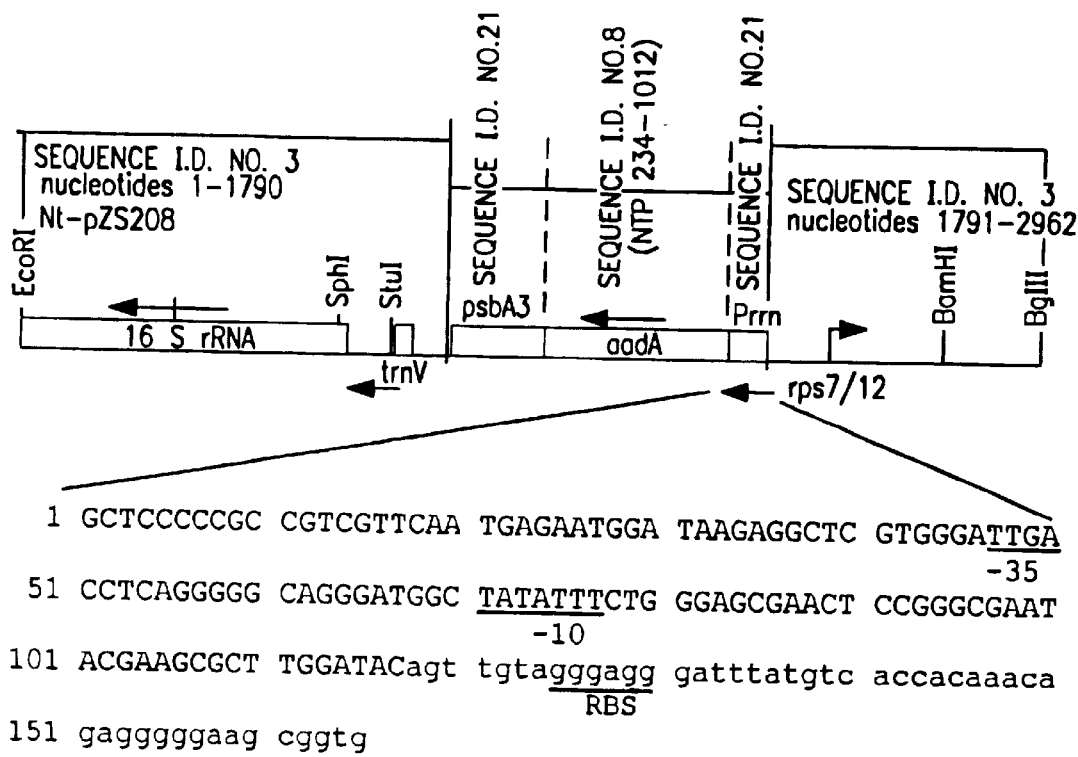
Figure 18B:
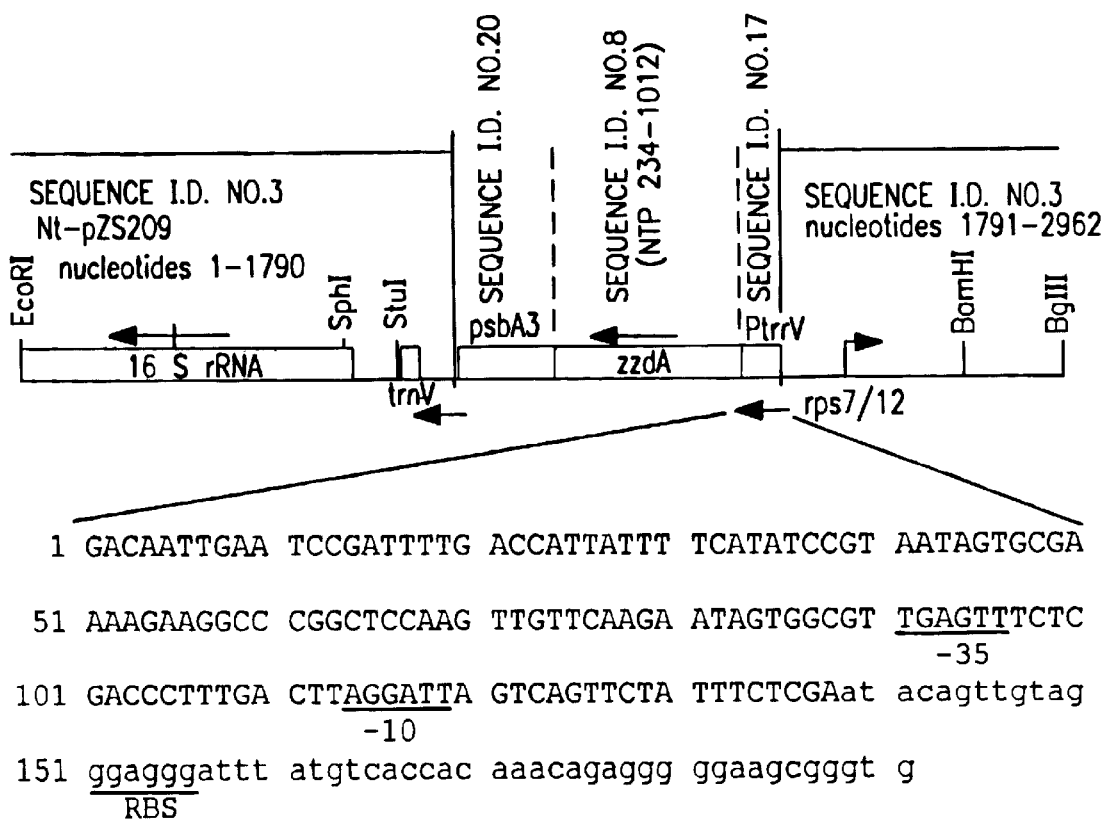
Figures 19A, 19B:
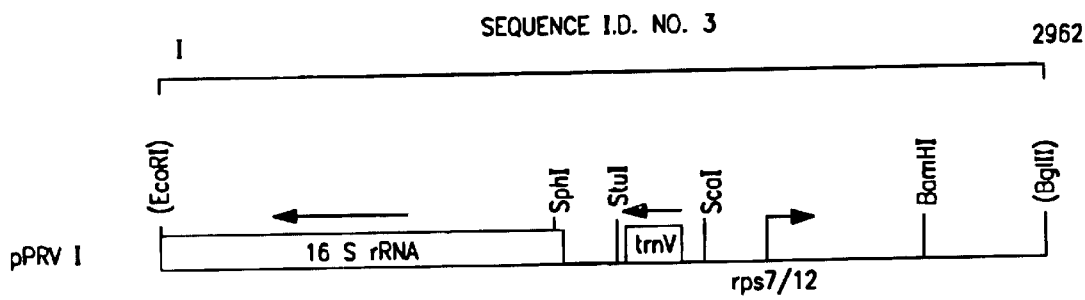
FIG. 19—The map of the transforming DNA in the pPRV vector family. Abbreviations: 16SrRNA, trnv, rps 12/7, and psb A are plastid genes; Prrn is the chimeric promoter derived from the ribosomal RNA operon promoter; BamHI, BglII, EcoRI, HindIII, KpnI, PstI, SacI, SalI, SphI, StuI are restriction enzyme recognition sites. The EcoRI and BglII sites that are present in the ptDNA, but were removed during construction, are in brackets. Arrows mark the direction of transcription of each gene.
Figure 19C:
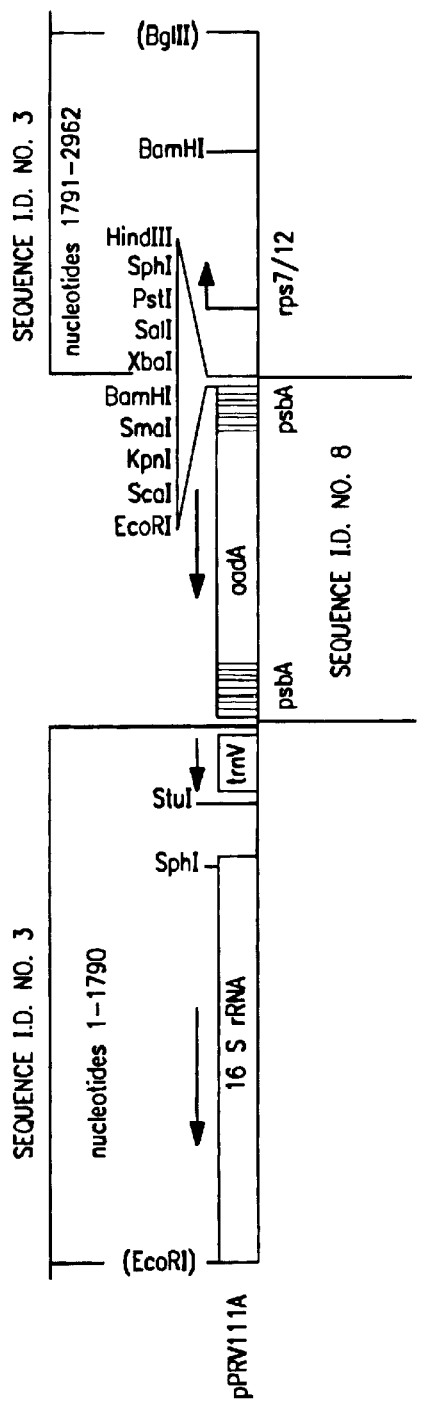
Figure 19D:
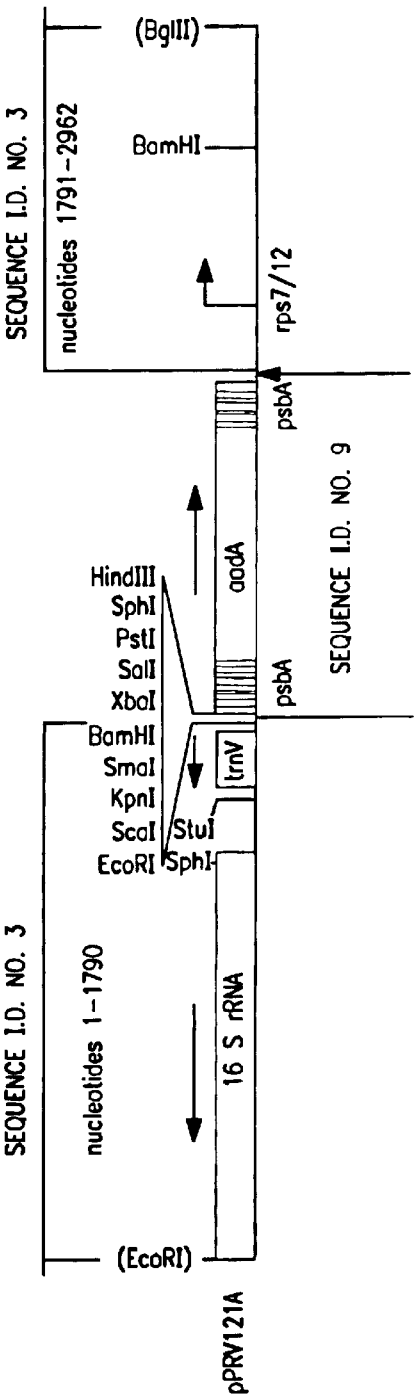
Figure 19E:
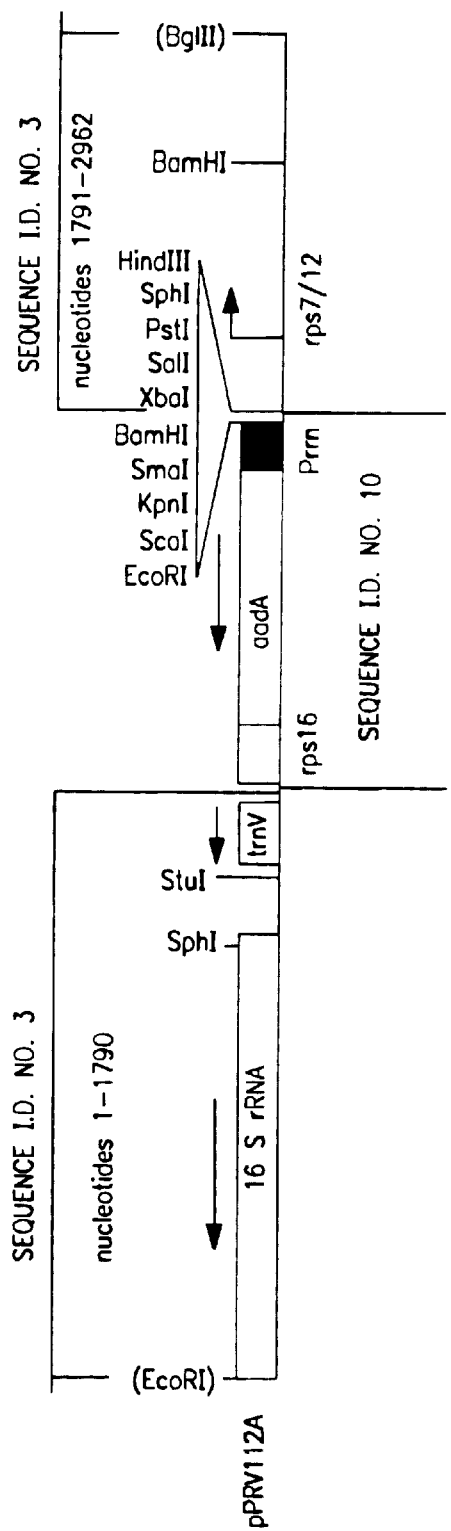
Figure 19F:
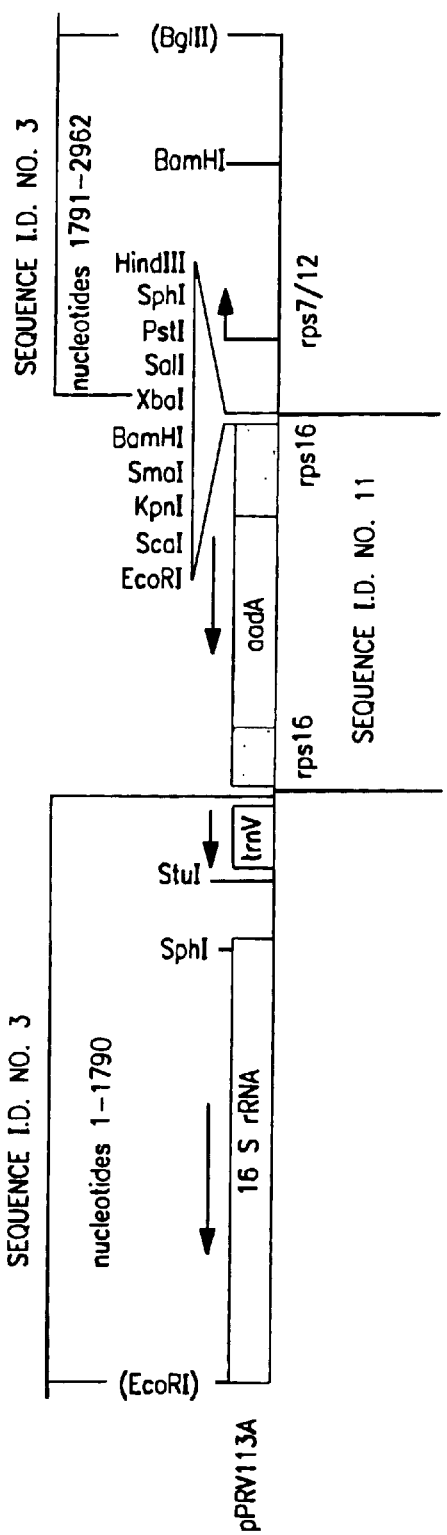
Figure 19G:
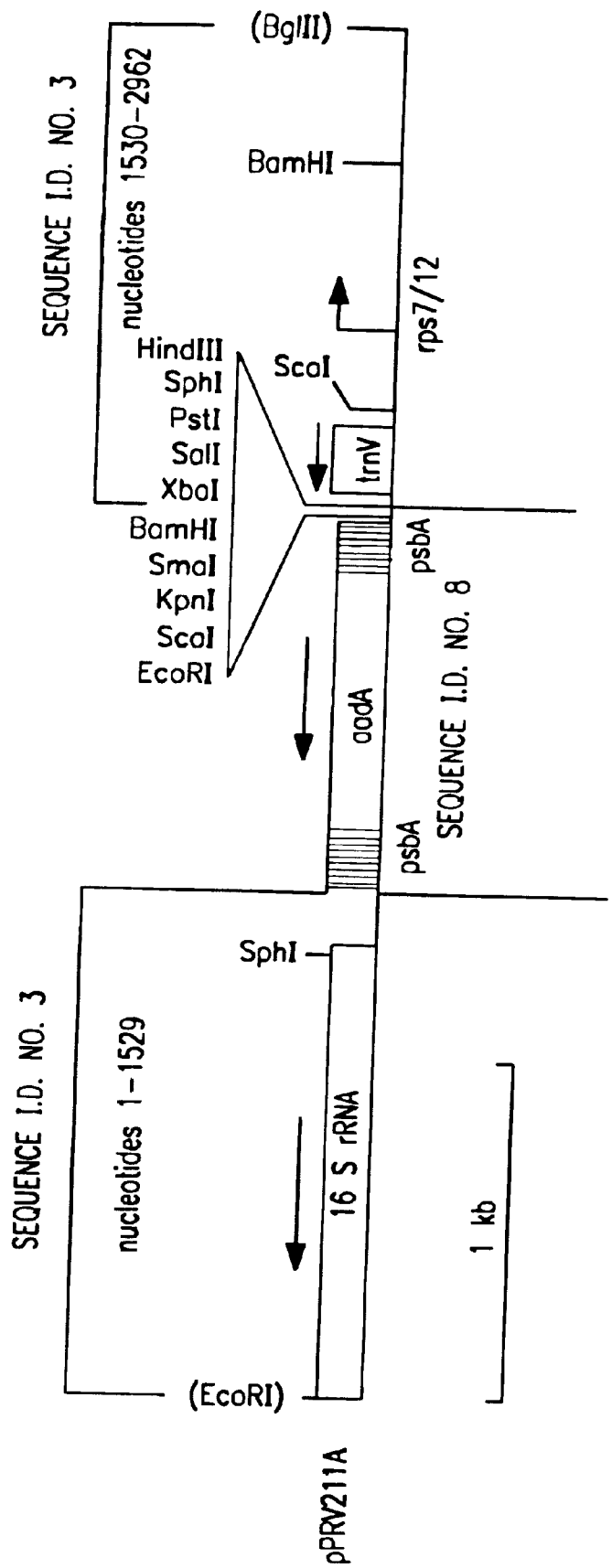

The pOVZ plasmids carry an aadA gene expressed in a psbA cassette (above). The psbA gene, the source of expression signals, is located relatively far, ~18-kb away from the pOVZ target site, in the large single-copy region of the plastid genome. However, other promoters that may be useful in these vectors are located in the inverted repeat, in close proximity to the StuI and ScaI insertion sites. Insertion of transgenes at these sites results in direct duplication of the promoter regions (FIG. 18). Such short direct and inverted repeats were shown to mediate plastid genome rearrangements on an evolutionary time-scale (Aldrich et al., Curr. Genet. 14: 137–46, 1988; Kanno et al., Theor. Appl. Genet. 86: 579–84, 1993). It was therefore prudent to test if duplication of the promoter regions results in transplastome instability.

Selectable aadA genes were cloned in expression cassettes with the strong constitutive promoter of the ribosomal RNA operon (Prrn), or the weak trnV gene, along with the psbA3'-region for mRNA stability. The chimeric genes were cloned in the ScaI site of the pPRV1 vector, and introduced into the plastid genome. The promoters of the transgenes and of the cognate endogenous promoters form a short direct repeat (FIG. 18). Deletion of aadA via the short direct repeats can be detected as the loss of spectinomycin resistance encoded in the transgene. To test if loss of aadA occurs, seeds were collected from plants transformed with plasmids pZS208 (Prrn5'/aadA/psbA3') and pZS209 (PtrnV5'/aadA/psbA3'). Seeds were then germinated on a selective spectinomycin medium to screen for spectinomycin sensitive seedlings by their white color. No sensitive seedlings were found in a population of 1,000 seedlings each, indicating that both transplastomes are stable. It was concluded therefore that duplication of sequences at or near the inverted repeat vector target site does not result in measurable instability of transformants.

The pPRV Plasmid Family

The pOVZ plasmids proved efficient for plastid transformation, and the foreign genes (aadA) were stably maintained in the plastid genome at the two sites targeted by the vector. To improve the utility of the vectors a series of plasmids was prepared with different cassettes driving the expression of the aadA gene. In addition, most major restriction sites have been removed from the plasmids and an MCS was inserted next to the aadA gene to provide unique cloning sites for passenger genes. An overview of the pPRV family is shown in FIG. 19; relevant DNA sequence features are given in FIG. 20.

Expression of Transgenes Between thetrnV Gene and the rps7/12 Operon

Foreign nonselectable genes can be introduced linked to aadA using the pPRV vector family. For the purposes of expression and mRNA stability, these genes should be provided with 5'- and 3'-regulatory regions from plastid genes. The 3' regions of plastid genes serve to stabilize the mRNAs, but are inefficient transcriptional terminators (Gruissem & Tonkyn, Critical Reviews in Plant Sciences 12: 19–55, 1993). Therefore, insertion at most intergenic regions is likely to yield transgenes which are expressed not only from their own engineered promoter, but also as readthrough transcripts from upstream endogenous promoters. Significant levels of readthrough transcription may interfere with the regulated transcription of plastid transgenes from engineered promoters, which may be undesirable for some applications of these vectors. Therefore, it was important to determine whether the MCS in one member of the pPRV family is located in a transcriptionally silent region suitable for targeting chimeric passenger genes without readthrough transcription.

Figures 21A, 21B:
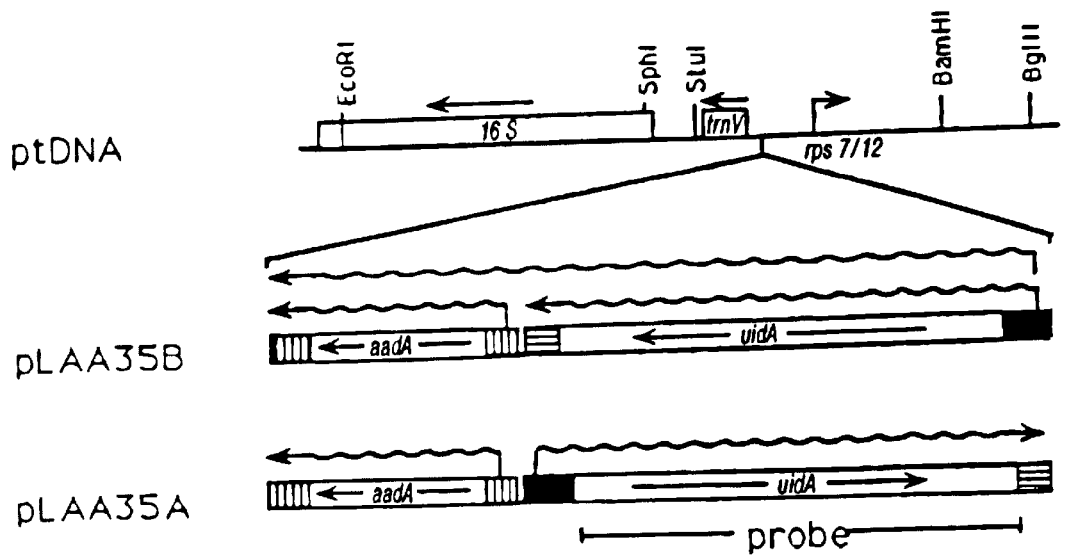
FIGS. 21A–21C—Transcription pattern of transgenes located between the trnV promoter and the rps7/12 operon.

The ScaI restriction site in pPRV1 is located between the divergently transcribed trnV gene and the rps12/7 operon. To test whether foreign genes inserted at this location are transcribed only from their own promoters, uidA transgenes were introduced into the plastid genome with pPRV111A and pPRV111B vectors. The uidA coding region in these constructs is expressed from the LRP, the strong, light-regulated promoter of the psbD operon. In the light, the mRNA for the chimeric uidA gene accumulates to high levels. RNA gel blots indicate that only a monocistronic mRNA is present when the uidA gene is transcribed towards the rps12/7 operon (FIG. 21). This finding is consistent with no readthrough transcription from the trnV plastid gene or the chimeric aadA gene. When the uidA gene is transcribed towards the aadA gene, a dicistronic message is formed, as expected due to inefficient termination through the rps16-3'-regulatory region of the uidA gene (Gruissem & Tonkyn, 1993, supra). The absence of uidA message in dark-adapted plants indicates that in this location the chimeric LRP mimics the light-regulation of its endogenous plastid counterpart (Christopher et al., 1992, supra). Furthermore, it is evident that there is no transcription of the region from outside non-regulated promoters in the dark. This finding indicates that this location is suitable for insertion of foreign genes whose transcription is designed to be regulated only by the chimeric promoter.

Discussion

Described in this Example are vectors that direct insertion of foreign genes at two different locations in the inverted repeat. An attractive feature of targeting transgenes into the repeated regions is their automatic duplication by the highly efficient gene conversion/copy correction mechanism operating in plastids (see Examples 1 and 2). Duplication of the transgenes is an advantage if high levels of expression are desirable.

In the pPRV series, the targeting ptDNA fragments are at least 1.2-kb to 1.5-kb in size on either side of the selectable aadA gene (FIG. 16). Targeting fragments of this size were sufficient to direct the integration of heterologous fragments up to 5-kb, without a significant reduction in the frequency of plastid transformation.

The integrated aadA gene was stable both at the StuI site (corresponds to DraI site in plasmid pJS75) and the ScaI site in the plastid genome. Insertion of a 2.5-kb chimeric uidA gene into the StuI-site was described in Example 4; information on the utility of the ScaI site is reported in this Example. Both of these insertion sites are located in the repeated region of the plastid genome.

Given that the 3'regions of plastid genes terminate transcription inefficiently, some degree of read-through transcription may be expected when inserting the transgenes at almost any location into the ptDNA. As described in this Example, the ScaI site in the pPRV series is unique, being the only characterized insertion site with no detectable read-through transcription when the transgene is oriented towards the rps12/7 operon. Since all transcripts from transgenes introduced at the ScaI location reflect the activity of the transgenic promoter, this site is uniquely suited to study transcriptional regulation using the transgenic approach. In addition, the availability of an insertion site such as this makes feasible novel applications, such as tissue-specific transcriptional regulation of plastid transgenes by nuclear genes, utilizing heterologous prokaryotic regulatory elements (Gossen et al., Trends in Biochem. Sci. 18: 471–75, 1993).

The pPRV family includes aadA genes expressed from different plastid regulatory sequences. The efficiency of transformation with each of these constructs is essentially identical, and is as high as described in Example 2 for the transformation of the large single copy region. The utility of the vector series is that it gives the option to choose vectors with the aadA gene expressed from signals other than those included in the passenger gene constructs. Given that the plastid genome of higher plants is highly conserved (Palmer, Trends in Genetics 6: 115–120, 1990; Sugiura, Plant Mol. Biol. 19: 149–168, 1992), the vectors are likely to find applications in a large number of species.

EXAMPLE 7

Development of 5' and 3' Regulatory Segments of Expression Cassettes for Optimum Expression of Foreign Proteins in Transformed Plastids Because higher plant cells contain multiple plastid genome copies, introduction of foreign genes into plastids automatically leads to their amplification to a high copy number, and the potential over-expression of their protein products. In order to maximize the potential of the plastid compartment for foreign gene expression, the 5' regulatory segment of a plastid expression cassette should produce large quantities of transgenic mRNA. In vivo transcription rates, determined in roots and leaves for several plastid genes (Mullet, Plant Physiol., 103: 309–13, 1993; Gruissem & Tonkyn; 1993, supra), have revealed that the 16S ribosomal RNA operon (rrn) and the rbcL and psbA genes have the strongest promoters (Deng & Gruissem, 1987, 1988; Rapp et al., 1992; Baumgartner et al., 1993). While the proteins encoded in the photosynthetic genes rbcL and psbA are translated efficiently in leaves, there is no accumulation of the encoded polypeptides in root tissue (Gruissem & Tonkyn, 1993, supra). Transgenes expressed from the psbA 5'-regulatory region are subject to the same posttranscriptional controls as the endogenous psbA gene (see Example 4). To obtain high levels of protein expression in non-photosynthetic tissues therefore, expression of transgenes from constitutive non-photosynthetic promoters is desirable.

The mRNA for the rrn operon accumulates to higher levels in leaves and roots than the mRNA for any other non-photosynthetic plastid gene, making this promoter ideal for constitutive expression cassettes (Deng & Gruissem, EMBO J., 7: 3301–08, 1988). Since the transcript of the rrn operon is not translated, expression of proteins from this promoter requires the addition of signals directing translation of the chimeric mRNA. In this Example, we have modified the rrn operon 5'-region for protein expression. Through the use of plastid transgenes we provide direct, in vivo evidence for the critical role of mRNA leader sequences, and the N-terminal portion of the coding region, for high levels of protein accumulation.

Materials and Methods

Production of transplastomic lines, RNA and protein gel blot analysis, and GUS assays have been described Examples 2, 3 and 4.

Construction of Promoter Fragments

Promoter fragments for the expression cassettes were prepared so that they can be excised with EcoRI, SacI or SalI at their 5'-ends, and by NcoI at their 3'-ends. The NcoI site (5'-CCATGG-3') includes the translation initiation codon.

The PpsbA(L) fragment contains the psbA gene promoter in a long segment (from nucleotides 1819 to 1596 in the ptDNA), and can be excised from plasmid pJS25 with the EcoRI/NcoI restriction enzymes (FIG. 23). The 5'-end of the fragment was excised from the plastid genome by SmaI at nucleotide position 1817; the NcoI site was created by oligonucleotide-directed mutagenesis, as described in Example 4.

The PpsbA(S) fragment contains the psbA gene promoter in a short segment (from nucleotides 1735 to 1596 in the ptDNA), and can be excised from plasmid pOVZ20 with the EcoRI/NcoI restriction enzymes (FIG. 23). The 5'-end of the fragment was created utilizing the BglII site at nucleotide position 1731; the NcoI site is derived from the PpsbA(L) fragment (see Example 6).

The PrbcL fragment contains the rbcL gene promoter from nucleotides 57,319 to 57,584 in the ptDNA, and can be excised from plasmid pIK100 with the SalI/NcoI restriction enzymes (FIG. 23). The 5'-end of the fragment was excised from the plastid genome by AccI at nucleotide position 59,026; the NcoI site was created by oligonucleotide-directed mutagenesis.

The Prps16 fragment contains the rps16 gene promoter from nucleotides 6,656 to 6,214 in the ptDNA, and can be excised from plasmid pHC61 with the EcoRI/NcoI restriction enzymes (FIG. 23). The 5'-end of the fragment was excised from the plastid genome by BclI at nucleotide position 6,652; the NcoI site was created by oligonucleotide-directed mutagenesis.

The PtrnVrbcL(S) fragment contains the trnV gene promoter from nucleotides 102,310 to 102,447, and is fused with a synthetic leader sequence designed after the rbcL gene leader between nucleotides 57,569 to 57,584 in the ptDNA. The PtrnVrbcL(S) fragment can be excised from plasmid pZS196 with the EcoRI/NcoI restriction enzymes (FIG. 23). The 5'-end of the fragment was excised from plasmid pJS75 (Staub and Maliga, 1992) with the ScaI restiction enzyme. This site was created by linker-ligation into a HincII-site in the plastid genome at nucleotide position 102,307; the NcoI site is part of the synthetic leader sequence (see Example 6).

The Prrn(L)rbcL(S) fragment contains the long rrn operon promoter fragment from nucleotides 102,561 to 102,677, and is fused with a synthetic leader sequence designed after the rbcL gene leader between nucleotides 57,569 to 57,584 in the ptDNA. The Prrn(L)rbcL(S) fragment can be excised from plasmid pZS195 with the EcoRI/NcoI restriction enzymes (FIG. 23). The 5'-end of the fragment was excised from plasmid pJS75 (Staub and Maliga, 1992) with the DraI restiction enzyme. This site was created by oligonucleotide-directed mutagenesis, inserting an AAA sequence between nucleotides 102,560 and 102,561; the NcoI site is part of the synthetic leader sequence. This plasmid is a progenitor of plasmid pZS197, which was described in Example 2.

The Prrn(S)rbcL(S) fragment is a derivative of the Prrn (L)rbcL(S) fragment, and contains the rrn promoter in a shorter fragment between nucleotides 102,561 to 102,660. In this construct the promoter region is separated from the leader region by an EcoRI site. The Prrn(S)rbcL(S) fragment can be excised from plasmid pZS177 with the SacI/NcoI restriction enzymes (FIG. 23).

Figure 26:
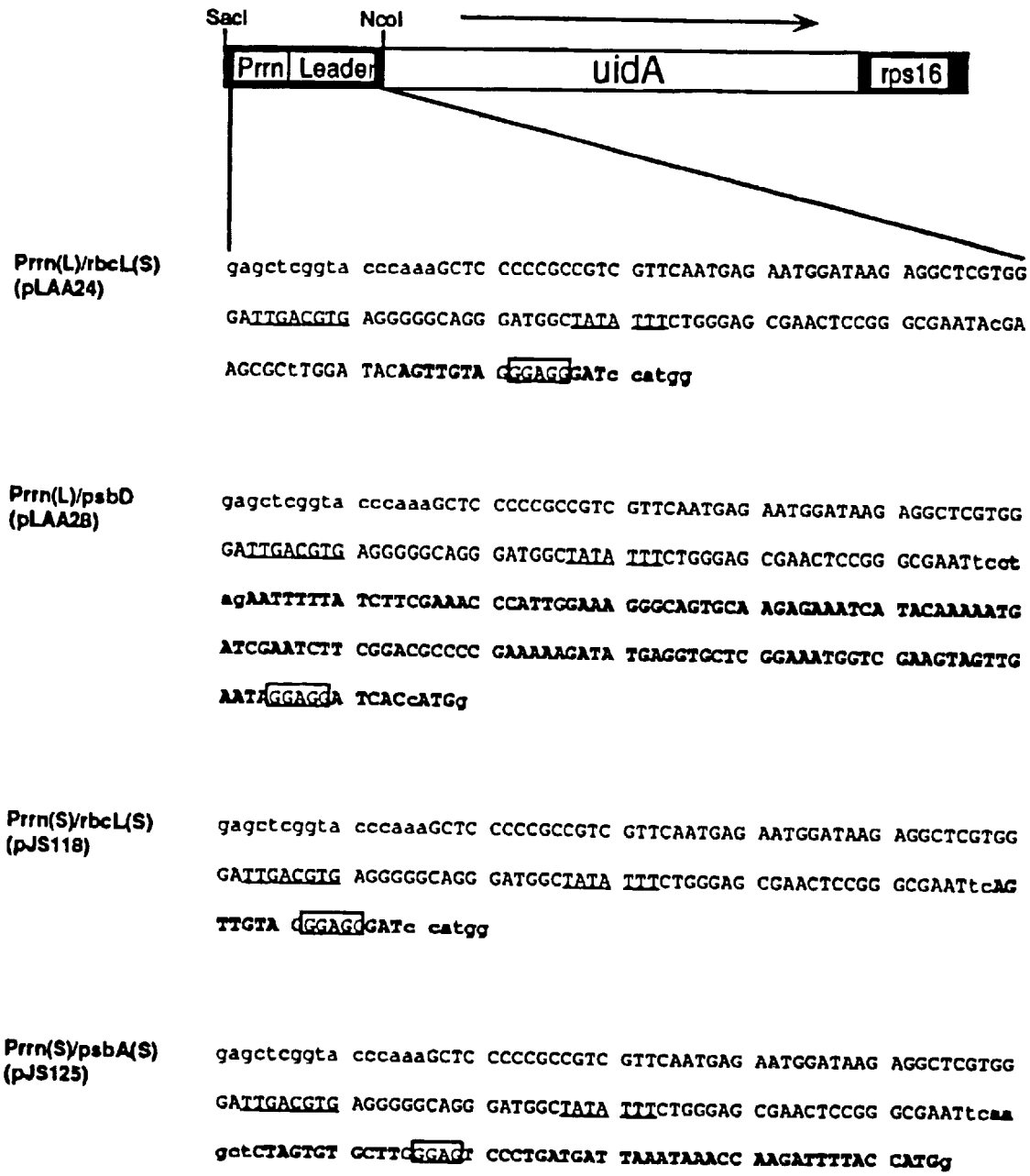
FIG. 26—DNA sequences of the Prrn 5'-regulatory regions with a segment of the RBS-containing 5' UTR of highly-expressed plastid genes. Shown above is a schematic representation of the uidA reporter genes. Below are listed DNA sequences of the Prrn(L)rbcL(S) (Sequence I.D. No. 18), Prrn(L)psbD, (Sequence I.D. No. 24) Prrn(S)rbcL(S) (Sequence I.D. No. 25), and Prrn(S)psbA(S) (Sequence I.D. No. 26) 5'-regulatory regions. Bold type represents sequences from the plastid rbcL leader region; plain type indicates sequences derived from the rrn operon 5' regulatory region; capital letters are equivalent to sequences in the tobacco ptDNA; sequence changes introduced by engineering are represented by lower case letters. The Prrn −35 and −10 consensus promoter elements are underlined, while the predicted ribosome binding site for each leader region is boxed.
Figure 27A:
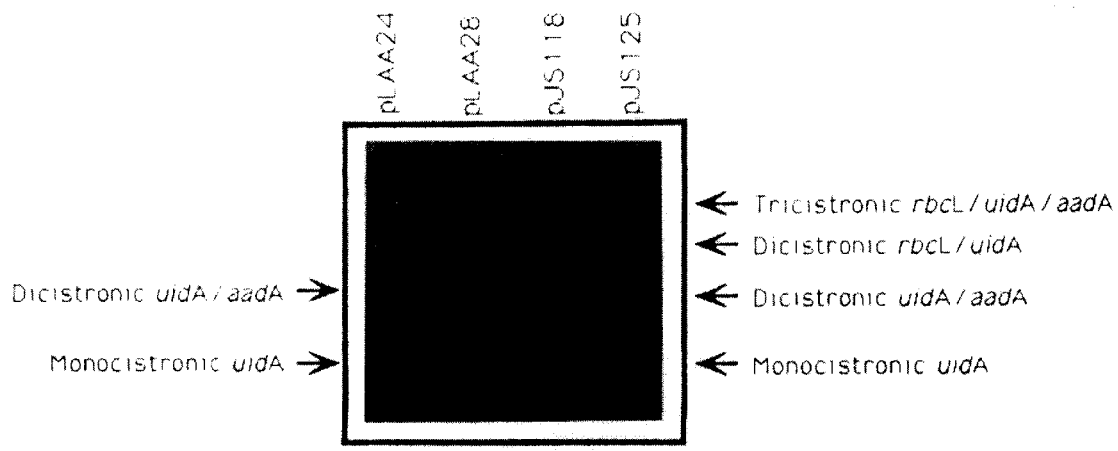
FIGS. 27A–B—Expression of uidA reporter genes with different Prrn-leader combinations. Relevant DNA sequences are shown in FIGS. 23 and 26.
Figure 27B:
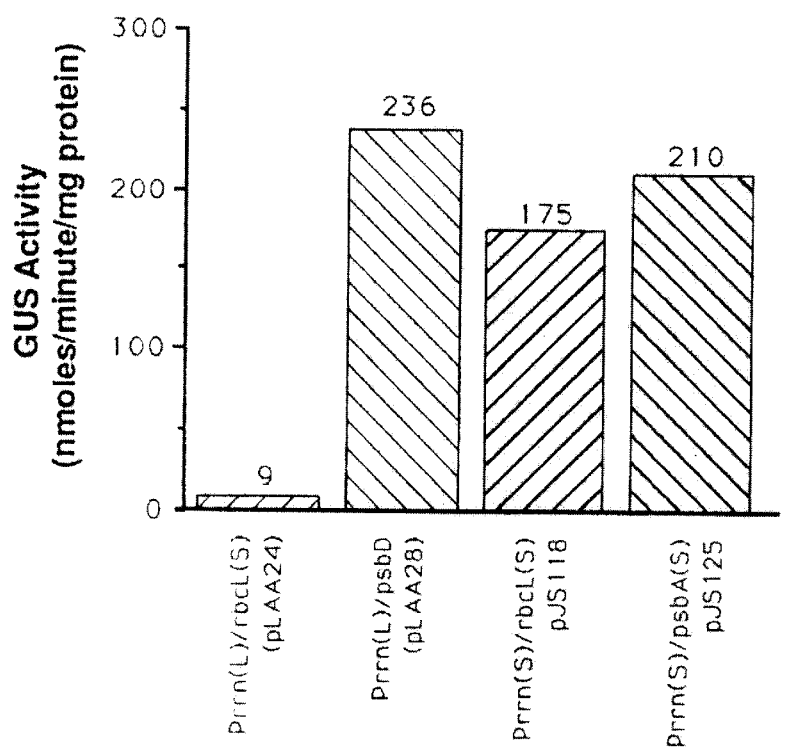

The Prrn(S)psbA(S) fragment contains the rrn promoter in a short fragment between nucleotides 102,561 to 102,660. The Prrn(S)psbA(S) fragment was obtained by ligating the filled-in SpeI-site in the psbA leader of pJS25 (Example 4) to the filled-in HindIII site of a Prrn(S)rbcL(S) fragment, in which the EcoRI-site was converted to a HindIII site by linker-ligation (5'-CAAGCTTG-3'). The sequence of the Prrn(S)psbA(S) fragment in plasmid pJS125 is shown in FIG. 26.

The Prrn(S)psbD fragment contains the rrn promoter in a short fragment between nucleotides 102,561 to 102,660. The Prrn(S)psbD(S) fragment was obtained by ligating the filled-in EcoRI-site in a Prrn(S)rbcL(S) fragment (see above plasmid pZS177) to an XbaI/NcoI fragment containing the psbD leader sequence. Before ligation, the XbaI-site was filled in. The XbaI/NcoI fragment was obtained by PCR-amplification of ptDNA, using oligonucleotides 5'-CCCTCTAGAATTTTTATCTTCGAAACCC-3' (Sequence I.D. No. 45) and 5'-CCCCAAGCTTCCATGGTGATCCTCCTATTCAAC-3' (Sequence I.D. No. 46). In the construct psbD leader sequences between nucleotides 34,330 to 34,460 are included (FIG. 26). The Prrn(S)psbD fragment can be excised from plasmid pLAA28 with the SacI/NcoI enzymes.

Construction of Terminator Fragments

Terminator fragments for the expression cassettes were prepared so that they can be excised with XbaI at their 5'-ends, and by HindIII at their 3'-ends.

The TpsbA(L) fragment contains the psbA gene 3'-regulatory region in a long segment (from nucleotides 533 to 142 in the ptDNA), and can be excised from plasmid pJS25 with the XbaI/HindIII restriction enzymes (FIG. 23). The 5'-end of the fragment was excised from the plastid genome at a Sau3AI site, the 3'-end at an AsuII site at nucleotide positions 530 and 140, respectively. Plasmid pJS25 was described in Example 4.

The TpsbA(S) fragment contains the psbA gene 3'-regulatory region in a short segment (from nucleotides 533 to 345 in the ptDNA), and can be excised from plasmid pOVZ20 with the XbaI/HindIII restriction enzymes (FIG. 23). The 5'-end of the fragment was excised from the plastid genome at a Sau3AI site, the 3'-end at a BspHI site at nucleotide positions 530 and 344, respectively. Plasmid pOVZ20 is described in Example 6. In plasmids pJS95, pJS118 and pJS139 the TpsbA(S) terminator was obtained by using the DraI site (at nucleotide 309) instead of the BspHI site (at nucleotide 344).

The TrbcL(L) fragment contains the rbcL gene 3'-regulatory region from nucleotides 59,028 to 59,238 in the ptDNA, and can be excised from plasmid pIK100 with the XbaI/HindIII restriction enzymes (FIG. 23). The 5'-end of the fragment was excised from the plastid genome at an AccI site, the 3'-end at an XbaI site at nucleotide positions 59,026 and 59,224, respectively.

The Trps16 fragment contains the rps16 gene 3'-regulatory region from nucleotides 5,087 to 4,939 in the ptDNA, and can be excised from plasmid pHC61 with the XbaI/HindIII restriction enzymes (FIG. 23). The XbaI site at the 5'-end was created by oligonucleotide-directed mutagenesis; the 3'-end of the fragment was excised from the plastid genome at an EcoRI site at nucleotide positions 4,938.

Construction of Promoterless uidA Construct in Plasmid pJS139

DNA sequence shown in FIG. 30 for plasmid pJS139 carrying the promoterless uidA construct was obtained by ligating an rbcL(S) leader/uidA/TpsbA(S) as an EcoRI (filled in)/DraI fragment into a plasmid pZS167 derivative. The EcoRV site of plasmid pZS167 (below) was converted to an EcoRI site by linker ligation (5'-CCGAATTCGG-3'; Sequence I.D. No. 47), and this site was filled-in prior to ligating to the EcoRI/HindIII fragment.

Chimeric Reporter Genes

The coding region of the uidA reporter gene, encoding β-glucuronidase, is available as an NcoI/XbaI fragment in plasmid pJS25 (Example 4). The NcoI site includes the translational initiation codon (ATG). The XbaI site is downstream of the stop codon. The expression cassettes are designed to accept such coding regions as an NcoI/XbaI fragments. The coding region of the kan gene, encoding neomycin phosphotransferase (NPTII) can also be excised as an NcoI/XbaI fragment from plasmid pTNH4 (Example 3) for expression in the cassettes. Plasmid pHC85 was obtained by inserting this NcoI/XbaI fragment in a Prrn(L) rbcL(S)/TrbcL cassette in vector pPRV211B. Construction of the kan chimeric gene in pTNH32 is described in Example 3.

Plastid Targeting Vectors

Insertion of reporter genes between the rbcL and accD (formerly ORF512) was obtained by ligating the reporter genes next to an selectable aadA gene in the unique EcoRV site of plasmid pZS167. This plasmid carries a 2.8-kb SacII/EcoRV targeting ptDNA fragment from nucleotides 57,750 to 60,593, respectively (both sites eliminated during construction). Within the fragment 1.5-kb and 1.3-kb segments flank the EcoRV site, which was created by linker-ligation into a BamHI site at nucleotide position 59,286 of the tobacco ptDNA (Shinozaki et al.). Plasmid pZS167 is the progenitor of the previously described plasmid pZS197 (Example 2).

Chimeric genes were inserted into the inverted repeat region between the trnV gene and the rps12/7 operon using plasmid pPRV111B (Example 6).

Results
Expression of Chimeric uidA From the Prrn Promoter

The rrn operon promoter has previously been engineered for expression of the spectinomcin resistance gene, aadA, for use as a selectable marker in transformation of tobacco plastids (see Example 2; FIG. 5, Sequence I.D. No. 1). The chimeric promoter, Prrn(L), contains a 117 nucleotide segment of the rrn operon 5'-region, including the −10 and −35 promoter elements, fused with 16 nucleotides of the highly-expressed rbcL untranslated leader sequence (nucleotides −18 to −3, 5' to the AUG translational initiation codon) designated as rbcL(S), that includes the GGGUGGG ribosome binding site (RBS). The chimeric 5-regulatory region, referred to in the earlier example simply as Prrn, will be referred to in this Example as Prrn(L)rbcL(S) region (or segment) to distinguish it from other modifications described in this Example. Expression of aadA from this cassette was sufficient for the efficient recovery of spectinomycin-resistant plastid transformants (Example 2). However, the amount of aminoglycoside-3"-adenyltransferase, the protein encoded in aadA, was not determined in Example 2.

Figure 22A:
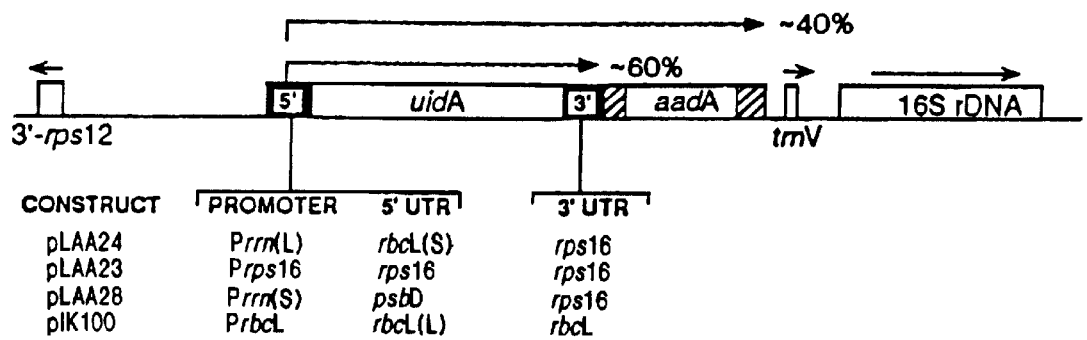
FIGS. 22A–22C—Schematic representation of chimeric uidA genes in the plastid genome.
Figure 22B:
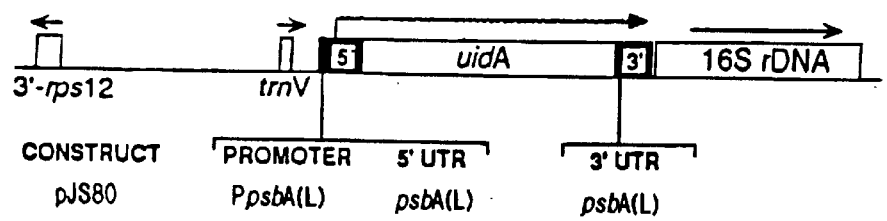

In order to evaluate levels of protein expression from this chimeric promoter, the aadA coding sequence was replaced with that of the reporter gene, uidA, encoding the easily assayable protein β-glucuronidase (GUS). To stabilize the uidA mRNA, the 3'-untranslated region (3'UTR) of the rps16 ribosomal protein gene was cloned downstream of the uidA transcription termination codon. The chimeric gene was cloned into a plastid transformation vector, pPRV111B, which targets insertion of passenger genes in the trnV and rps12/7 intergenic region, as described in Example 6. The expression of this uidA gene in plasmid pLAA24 was compared to the expression of other uidA constructs under control of the 5' and 3' regulatory sequences of well-characterized plastid genes. Chimeric genes were constructed by inserting the uidA coding region in place of the coding region of the following plastid genes: rbcL and psbA, two highly expressed photosynthetic genes, and rps16, a weakly-expressed non-photosynthetic gene encoding a ribosomal protein. Transgenic plants with the rbcL (plasmid pIK100) and rps16 (pLAA23) constructs are reported here; those with the psbA construct (pJS80) have been previously described in Example 4. Constructs are summarized in FIGS. 22A, B, and the DNA sequence of the 5'- and 3'-regulatory regions are shown in FIG. 23.

Figure 24A:
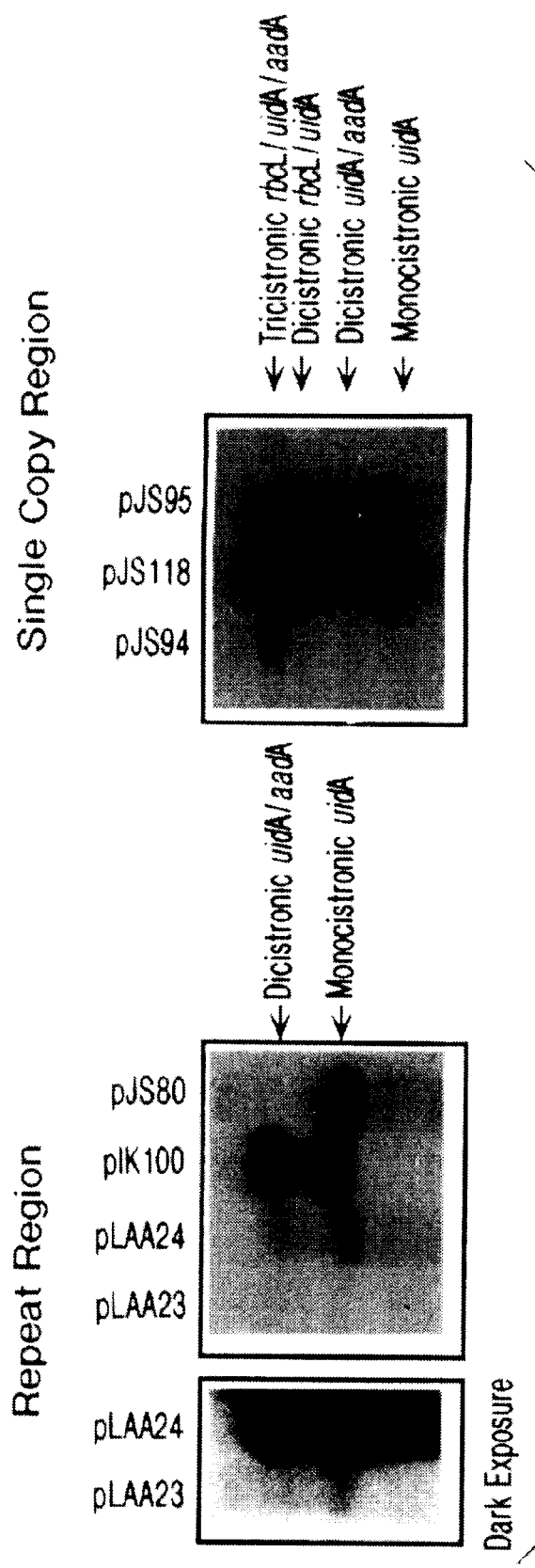
FIGS. 24A–B—Expression of chimeric uidA genes In leaves of transgenic plants.

Comparison of steady-state mRNA levels by gel blot analysis showed that the uidA constructs with the Prrn(L) rbcL(S), rbcL and psbA 5' regions are expressed at a high level, whereas the rps16-construct exhibits low level expression (FIG. 24). The promoter strength of chimeric uidA genes reflects the relative strength of that of the endogenous promoters (PpsbA≡Prrn≡PrbcL>>Prps16; Deng & Gruissem, Cell, 49: 379–87, 1987; Rapp et al., J. Biol. Chem., 267: 21404–11, 1992). In each case, the levels of uidA-containing message were normalized to the levels of endogenous 16S rRNA in the RNA sample, as detected by probing with a 16SrDNA probe (data not shown). The uidA probe on gel blots with RNA of pLAA23, pLAA24 and pIK100 transgenic plants hybridized to two transcripts; the smaller transcript is the size of a monocistronic uidA message, the larger is a dicistronic message including aadA (FIG. 24A). When probed with aadA, only the larger transcript is detected (data not shown). The dicistronic message forms as the result of inefficient termination of transcription at the rps16 or rbcL 3' regions.

Figure 24B:
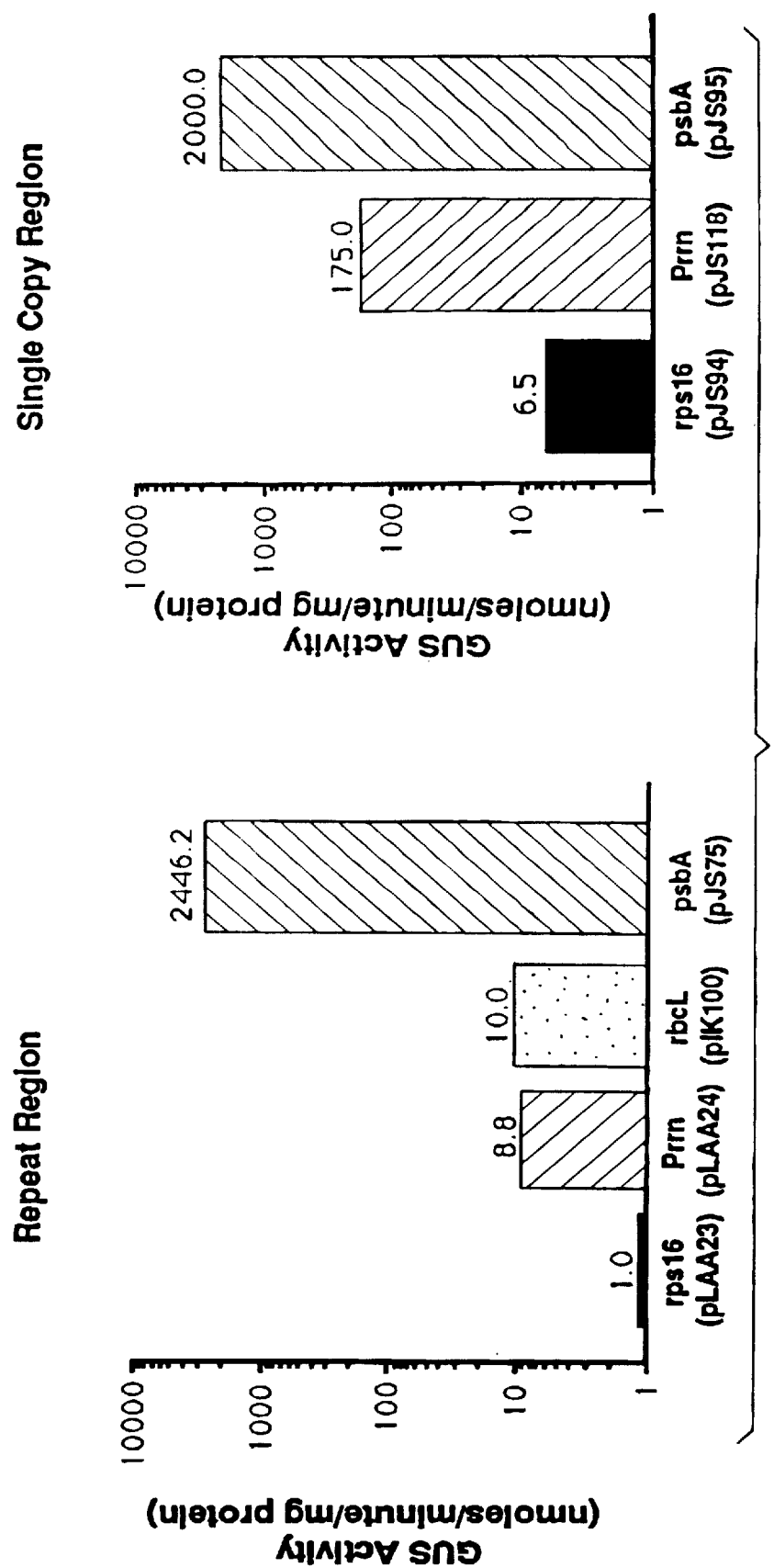

GUS activities were also determined in protein extracts from the leaves of the transgenic plants. High activities were measured in plants expressing uidA in the psbA cassette (pJS80), while significantly lower (200 to 2000 fold) activities were detected in plants with the Prrn(L)rbcL(S), rbcL and rps16 constructs (FIG. 24B)

A similar trend in GUS accumulation was observed when the genes were inserted at a different location, in the large single-copy region of the ptDNA. The rps16 and psbA chimeric genes were identical with those tested in the repeated region, and are carried in targeting plasmids pJS94 and pJS95, respectively. The 5' regulatory region of the rrn promoter cassette, Prrn(S)rbcL(S), contains a shorter (103 nt) version of the rrn promoter (FIG. 23B); the uidA message in plasmid pJS118 is stabilized by the addition of the psbA 3'-end. The transgenes were introduced into the plastid genome in the intergenic region between rbcL and accD, linked to a selectable aadA gene (Examples 2, 3; diagrammed in FIG. 22C).

At both locations, the amount of GUS produced from the Prrn cassettes is disproportionately low given the high amounts of uidA mRNA accumulated. Inefficient mRNA translation is due to posttranscriptional regulation that may operate through the 5' UTR, the coding sequence or the 3' UTR. Transgenes have been designed to investigate the contribution of each of these sequences to translational efficiency.

The 3' UTR Does Not Exert a Major Effect on Transgene Expression

The 3' UTR of the uidA gene in pLAA24 derives from the weakly-expressed (Baumgartner et al., 1993, supra) rps16 ribosomal protein gene. We tested therefore if this 3' UTR could be responsible for the low levels of GUS observed. A series of constructs (FIG. 22C) was prepared containing the same 5'-region (psbA) expressing the same reporter enzyme (GUS), but with the 3' UTR derived from different plastid genes: the highly-expressed psbA (pJS95) and rbcL (pJS127) genes, and the rps16 gene (pJS93). The transgenes were introduced into the plastid genome in the intergenic region between rbcL and accD, linked to a selectable aadA gene.

Figure 21C:
Figure 25A:
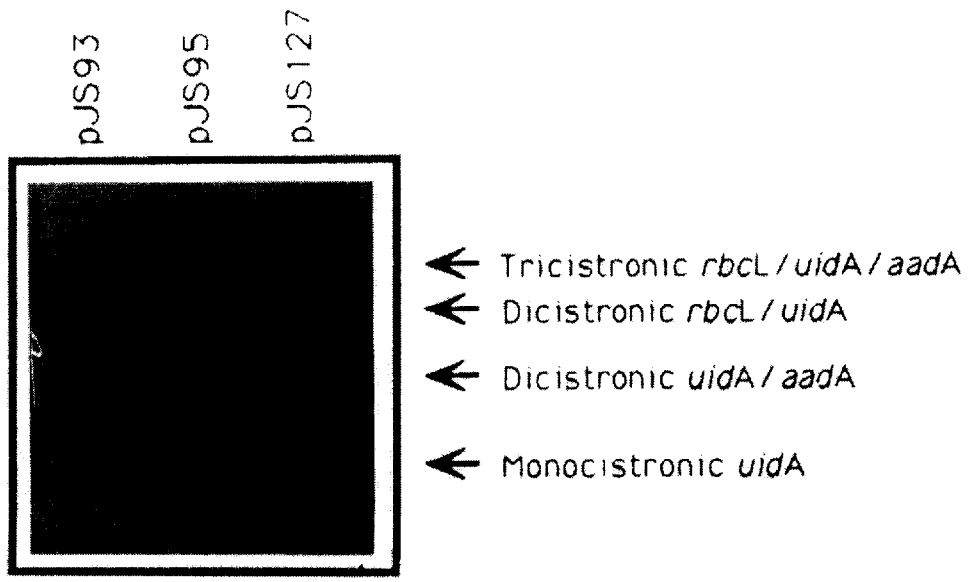
FIGS. 25A–B—Expression of uidA transgenes with different 3' UTR sequences.
Figure 25B:
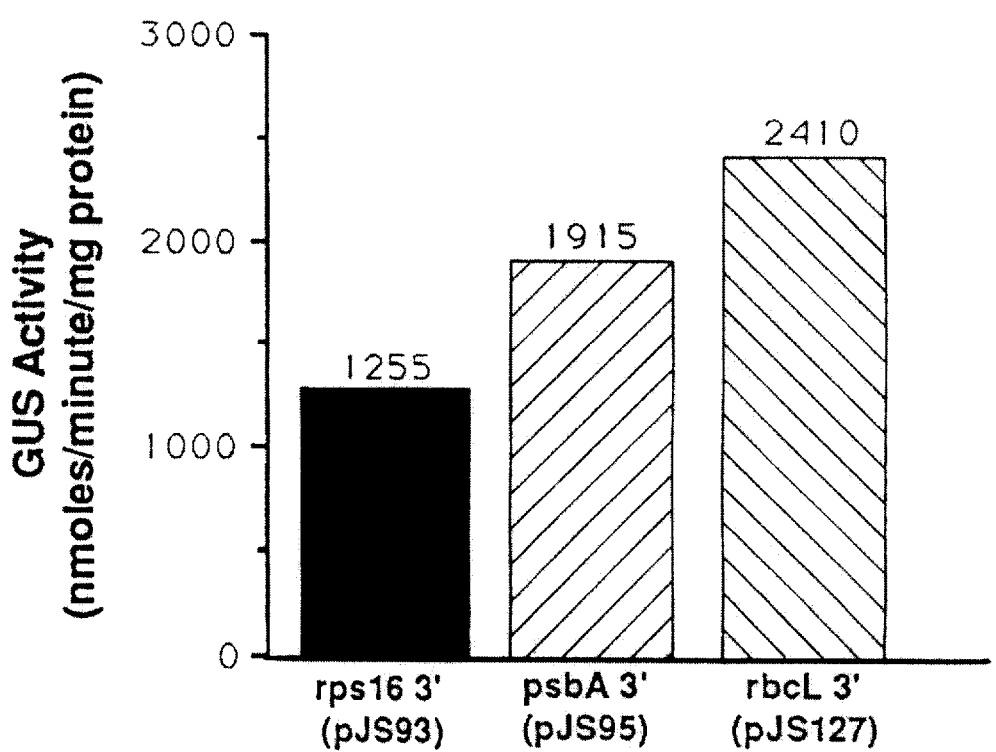

Probing of RNA gel blots with the uidA coding region detected a series of uidA-containing transcripts in each of the transgenic lines. The most abundant are the monocistronic messages derived from the psbA promoter, and the dicistronic messages originating from the rbcL promoter and reading through ithe uidA transgene (FIG. 21C). Additional, less abundant messages are derived from additional readthrough into the aadA and accD genes (FIG. 21C). Among the different uidA 3' UTR constructs differences were observed only in steady-state level of mRNA species with uidA as the terminal cistron (FIG. 25). The highest mRNA levels were obtained with TrbcL, followed by Tpsba (S) and Trps16. The mRNA levels varied in the 2-fold range reflected in the GUS activities measured for each transgenic line. Therefore, by changing the 3' UTR differences we could increase the levels of GUS accumulation by two-fold at this ptDNA location.

Improved GUS Accumulation From Prrn by Addition of Chimeric Leader Sequences

The 5' UTR has been shown to regulate translation of mRNAs for plastid photosynthetic genes in Chlamydomonas (Rochaix, Ann. Rev. Cell Biol., 8: 1–28, 1992). To test the feasibility of improving the translation of uidA mRNA, we replaced the rbcL(S) leader in the chimeric rrn 5'-region with portions of leader sequences (including the RBS) of psbA and psbD, two other highly expressed photosynthetic genes (FIG. 26). Therefore, these chimeric genes contain the same promoter, Prrn(S) and coding region (uidA) but differ in their leader sequences.

The reference uidA gene with the Prrn(L)rbcL(S) 5' region (pLAA24) and the Prrn(L)psbD constructs were introduced into the repeated region of ptDNA. The exchange of the leader sequence resulted in a 25-fold increase in GUS accumulation, while the mRNA levels increased in a 2-fold range.

Figure 22C:
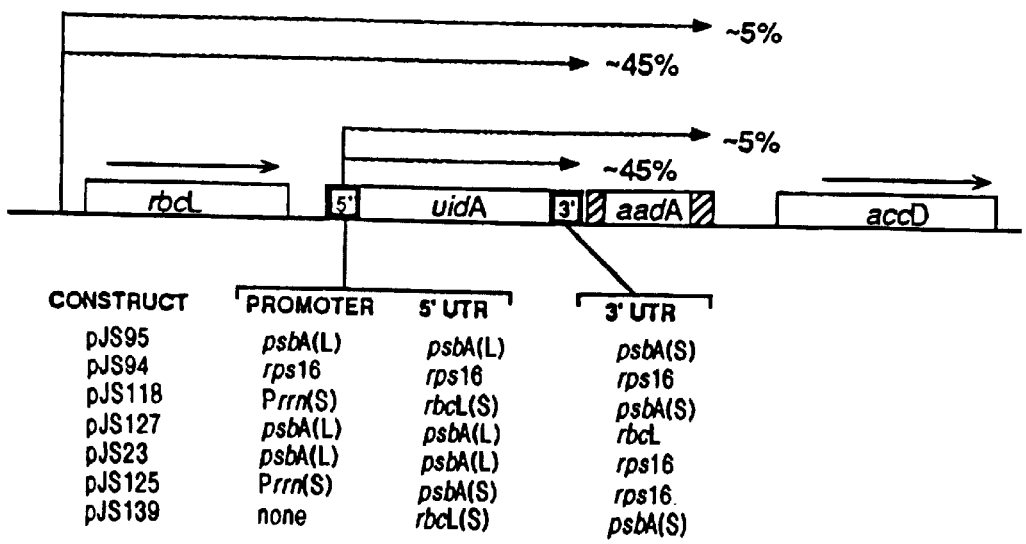

Prrn(S)rbcL(S) and Prrn(S)psbA(S) constructs in plasmids pJS118 and pJS125, respectively, were tested for expression in the single-copy region, between rbcL and accD of ptDNA (FIG. 22C). GUS accumulation from the Prrn(S)psbA(S) 5'-region was slightly higher than from the reference construct Prrn(S)rbcL(S), even though the mRNA levels for the reference gene were ~5-fold higher. These data indicate that the modification of the leader sequence can significantly (5- to 25-fold) increase the amount of protein produced from the same message.

Coding Region Affects Protein Expression From Prrn(L) rbcL(S) 5'-region

Stem-loop structures in the 5' UTR were shown to be important for the expression of plastid genes in Chlamydomonas (Rochaix, 1992, supra). Secondary mRNA structures may also form by interaction of the 5' UTR with the coding region of the mRNA, thereby modifying translability of the message. It was of interest, therefore, to test expression of a protein coding region other than uidA from the Prrn(L)rbcL(S) 5'-region. Neomycin phosphotransferase (NPTII), encoded in the bacterial gene kan, was expressed in cassettes with the Prrn(L)rbcL(S) 5'-region. Two versions of the kan coding sequence were engineered. Plasmid pHC85 carries a kan gene which was mutagenized to create an NcoI-site encompassing the translation initiation codon ATG. In plasmid pTNH32, the NcoI site was removed, and the five N-terminal amino acids of the ribulose-1,5-bisphopsphate carboxylase/oxygenase (Rubisco) large subunit were fused with NPTII (FIG. 28; see Example 3).

Figure 29A:
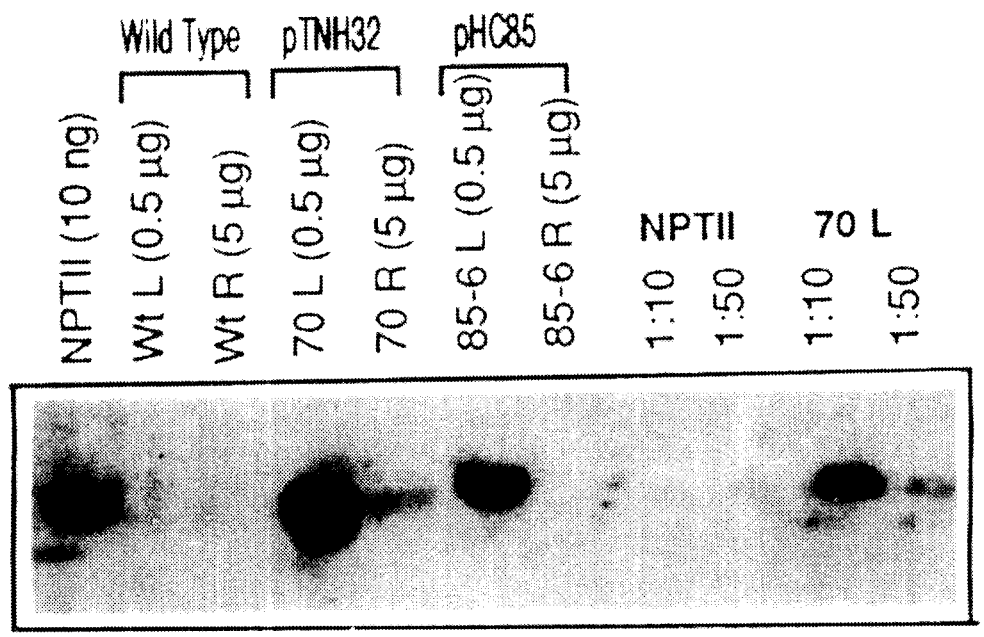
FIGS. 29A–B—Expression of the bacterial gene kan in transgenic tobacco plants.
Figure 29B:
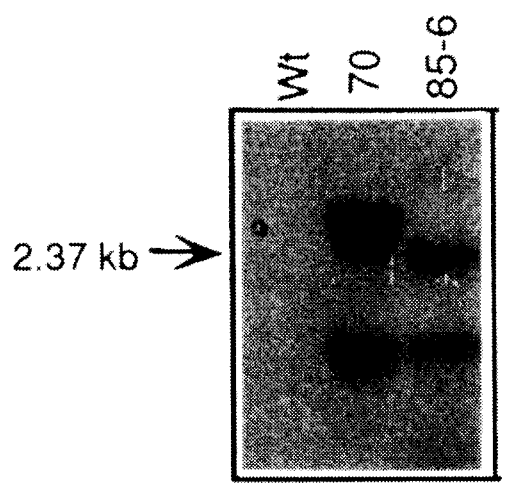

Protein gel blots detected high levels of NPTII accumulation for both constructs. In plants transformed with pTNH32, NPTII is present as ~1% of the total leaf protein (FIG. 29A). Levels of NPTII were ~10-fold higher in the plants transformed with plasmid pTNH32, carrying the construct with the five additional N-terminal amino acids. The mRNA levels, however, were only ~3-fold higher for this construct (FIG. 29B). Increased protein accumulation with the added five amino acids may be due to the altered sequence context of the translational initiation codon AUG, and/or due to increased stability of NPTII as a result of the N-terminal fusion. In addition, these results demonstrate that, when using a different reporter gene region (kan instead of uidA), high levels of protein expression can be obtained with the Prrn(L)rbcL(S) 5'-region.

Protein Expression in Roots Using the Prrn Promoter

One objective of the present study was to identify plastid regulatory elements promoting the expression of foreign proteins in the roots of transgenic plants. Since neither the psbA nor the rbcL cassettes give detectable GUS accumulation in roots (see Example 4), it was of interest to test the potential of chimeric Prrn cassettes for expression in roots. We examined the root expression of the kan gene in pTNH32 regulated by the Prrn(L)rbcL(S) chimeric 5' region, a construct which yielded high protein levels in leaves. For this construct, the level of protein accumulation in roots, although lower than that in leaves, was readily detectable (FIG. 29A). Accumulation of Prrn(S)psbA(S) 5'-region plants transformed with pJS125 construct is ~50-fold lower in roots than in leaves (not shown). These data clearly demonstrate the potential of the constitutive Prrn promoters for root expression of foreign proteins.

Polycistronic mRNAs Are Translated in Plastids

Figure 30A:
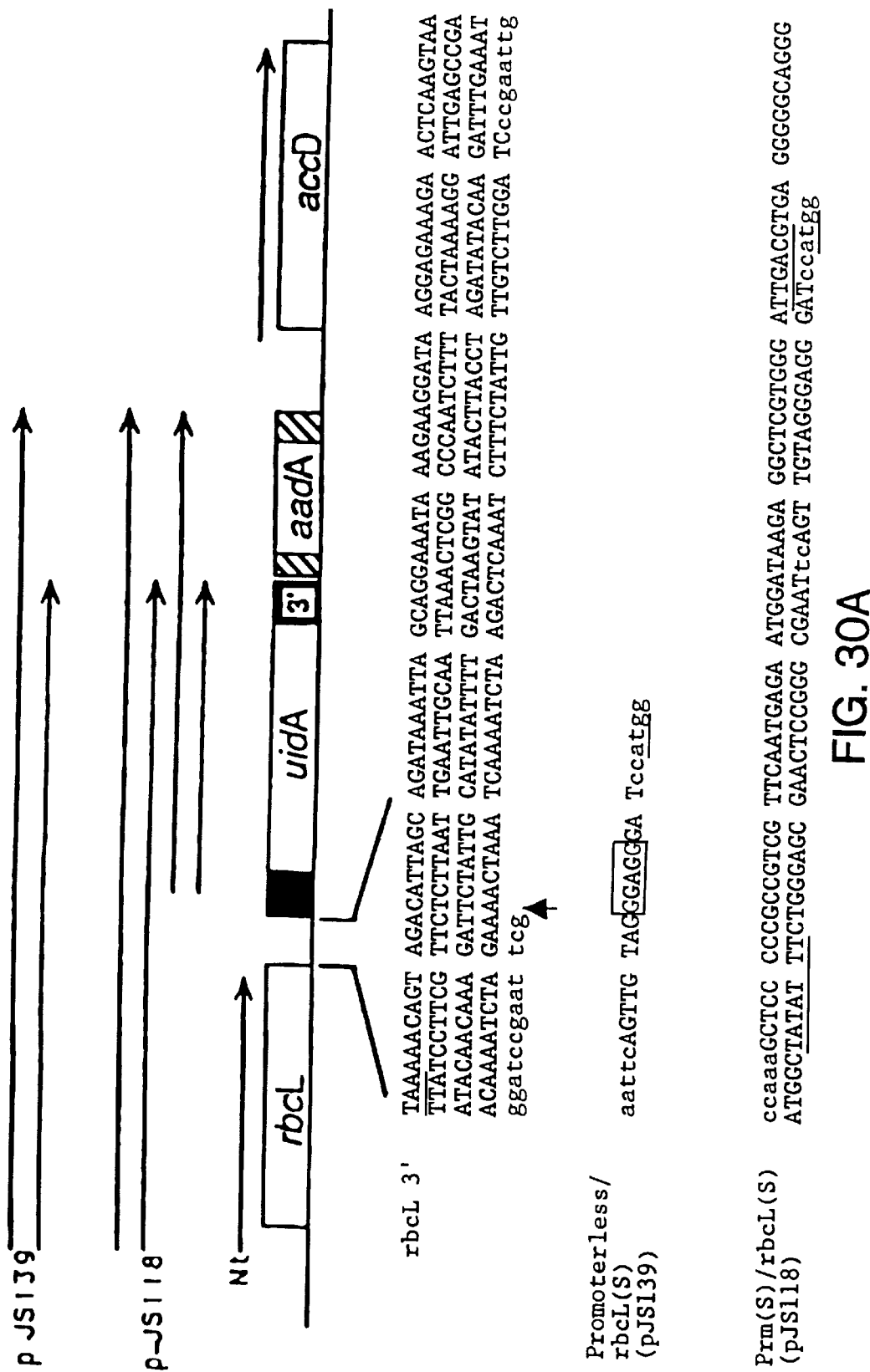
FIGS. 30A–B—Expression of uidA from a promoter-distal cistron in plastids.
Figure 30B:
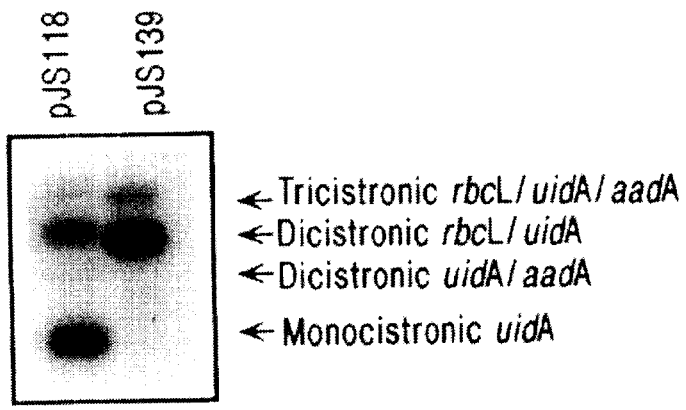
Figure 30C:
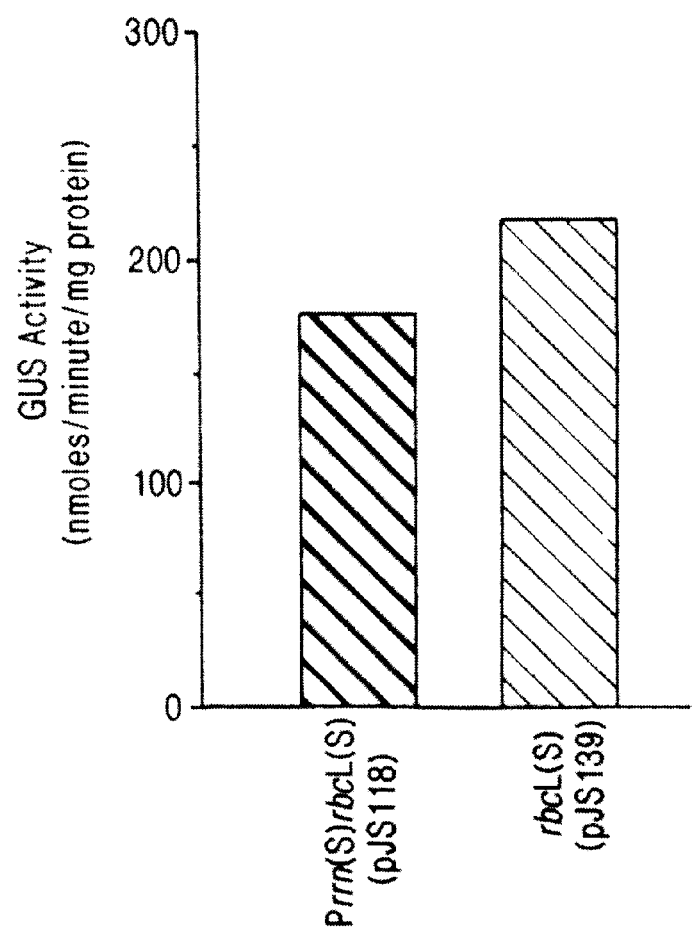
(FIG. 30C): GUS accumulation in pJS139 plants from polycistronic mRNAs.

Transgenes targeted to the rbcL-accD intergenic region are expressed both as monocistronic and polycistronic transcripts (FIGS. 24 and 25). To determine whether the second cistron of a polycistronic mRNA is translated, a uidA transgene bearing an RBS, but lacking a promoter, was cloned downstream of rbcL so that uidA coding region is transcribed by readthrough from the rbcL promoter. In this construct (pJS139), there are no in frame AUG codons between the stop codon of the rbcL sequence, and the initiating AUG of the uidA (FIG. 30A). Examination of transgenic plant mRNA revealed the absence of any monocistronic uidA transcripts, as predicted due to the absence of a promoter driving uidA. However, the polycistronic readthrough transcripts initiation from the upstream rbcL promoter were readily apparent (FIG. 30B). High levels of GUS activity were detected in these transgenic plants (FIG. 30C), demonstrating that the second cistron of this polycistronic message can be efficiently translated in plastids.

Discussion

We have used plastid reporter genes to investigate the contribution of regulatory sequences to the expression of foreign proteins in plastids. Steady-state leaf mRNA levels for transgenes were high when expressed from the psbA, Prrn and rbcL promoters, but were low when driven by the rps16 promoter. The mRNA levels obtained for the transgenes transcribed from these promoters therefore directly reflect the promoter strengths in their natural plastid gene contexts (Rapp et al., 1992, supra). Consequently, by choosing an appropriate plastid promoter we can manipulate the steady-state mRNA levels for transgenes over a wide (~100 fold) range.

The 3' UTR was shown to stabilize the plastid mRNAs (Gruissem and Tonkyn, 1993, supra). In the tested constructs, the stead-state mRNA levels were primarily determined by promoter strength. The 3' UTRs slightly differed in their efficiency in stabilizing mRNA levels, the TrbcL being the most efficient, followed by TpsbA and Trps16.

High levels of mRNA do not guarantee high levels of protein accumulation. From the Prrn promoters, we obtained comparatively low levels of GUS expression when providing the RBS and a short segment of the rbcL 5' UTR. The GUS expression levels could be increased by using the equivalent regions of other highly expressed genes, psbA and psbD. It should be mentioned that the rbcL gene has a good consensus ribosome binding site, GGAGG, positioned at nucleotide −6 upstream of the AUG, and presumed to be optimal for translation initiation (Bonham-Smith & Bourque, Nucleic Acids Res., 17: 2057–78, 1989), whereas the psbA RBS (GGAG) is irregularity spaced at nucleotide position −33. Based on the RBS alone, we would have expected higher levels of GUS accumulation from the rbcL(S) than from the psbA(S) Prrn-leader fusion. The spacing and sequence of the psbD RBS, GGAGG, is similar to that of rbcL (Shinozaki et al.), but the uidA transgene with this leader accumulates significantly higher levels of GUS (25×) than that with the rbcL leader. Apparently, efficiency of mRNA translation is also influenced by other factors, such as the folding of mRNA, and the interaction of the folded structures with translational control factors.

The efficiency of the Prrn (L)-rbcL (S) 5'-regulatory region for directing translation appears to depend to an extent upon the coding region being expressed. While inefficient for expressing GUS, accumulation of NPTII was high, ~1% of the total cellular protein, as long as the enzyme was translationally fused at its N-terminus with 5 amino acids of the rbcL coding region. NPTII in this case was translated from an mRNA containing the rbcL leader sequence from nucleotides −18 to +18 around the rbcL translation initiation codon, A of the ATG being +1. This finding supports the importance of the AUG context for translation, including the N-terminal portion of the coding region (Bonham-Smith & Bourque, 1989, supra). The importance of sequences downstream of AUG for mRNA translation was also observed in Chlamydomonas plastids where fusion of the aadA coding region with N-terminal portions of plastid photosynthetic genes was necessary to obtain phenotypic resistance (Goldschmidt-Clermont, 1991, supra). The difference in translational apparatus in Chlamydomonas and higher plant plastids is highlighted by the fact that in tobacco no translational fusion was necessary to obtain phenotypic resistance with aadA in any of the three cassettes tested (see Example 6).

Plastid genes are targeted in a precise location in the plastid genome. In contrast to nuclear genes, the expression of transgenes is predictable, and depends on the flanking genes. If the transgene is isolated transcriptionally, transcription and steady-state mRNA levels are dependent only on its 5'- and 3'-regulatory regions. The rrn and rps12/7 operon intergenic region used in this study represents such a transcriptionally silent location (see Example 6). In contrast, if the transgene is cloned downstream of an abundantly transcribed gene such as rbcL or psbA, the transgene is transcribed not only from its own promoter but also from the upstream promoter due to inefficient termination of transcription at the upstream 3' UTR. Since promoter-distal cistrons in polycistronic mRNAs are also translated (below), expression from the upstream promoters contributes to the pool of translatable mRNAs. A dramatic example is the Prps16/uidA/Trps16 construct, with 5-fold higher levels of GUS when downstream of rbcL as compared to when it is expressed from its own promoter in the repeated region (FIG. 24).

Given the large number of readthrough transcripts, we tested translation of promoter-distal cistrons by fusing a promoterless uidA coding region with the rbcL 3' UTR. Accumulation of GUS to high levels in plastids containing this construct indicates that the downstream ORFs of polycistronic messages are translated. This is direct in vivo confirmation of previously reporter biochemical evidence for the translation of each of the reading frames in polycistronic plastid messages (Barkan, EMBO J., 7: 2637–44, 1988). Since polycistronic messages are translated efficiently, it is not necessary to include promoter fragments for expression of foreign proteins as long as the coding region is properly fused to an upstream region. The demonstration that polycistronic mRNAs are efficiently translated opens the way to incorporate gene clusters, encoding complex metabolic pathways, into the plastid genome. Tissue-specific or light-regulation of such transgenes may be ensured by translational coupling with an appropriate plastid gene. A naturally-occurring example of this expression mechanism is translational coupling of the atpB/atpE genes (Shinozaki et al., Gene, 24: 147–55, 1983).

Root expression of reporter enzymes was detected when using derivatives of the constitutive rrn promoter. This demonstrates the potential of the expression cassettes for production of proteins in non-photosynthetic tissues. Given the lower number of plastid genome copies in roots (Bedich, BioEssays, 6: 279–82, 1987), it was not surprising to find a relatively low level of protein expression in roots. Given the ability to increase GUS accumulation by modifying the 5' UTR, a logical approach to boost root expression is incorporation of leader sequences of highly expressed mRNAs, such as the omega sequence of the TMV coat protein gene.

By fusing the Prrn promoter with RBS-containing segments of the 5' UTR of highly-expressed plastid photosynthetic genes, we constructed a series of chimeric 5' regulatory regions for constitutive, high-level protein expression in plastids. For optimizing expression of new genes, many options are available. These cassettes can be utilized to drive expression of selectable marker genes in plastid transformation vectors, and for the expression of foreign genes for crop improvement.

As one example, biosynthesis of polyhydroxybutyrate (PHB), biodegradable thermoplastic, has been shown in *Arabidopsis thaliana* as the result of the expression of *Alcaligenes eutrophus* genes in the nucleus (Y. Poirier et al., Science 256: 520523, 1992). The vectors described would be useful for high expression of the PHB biosynthetic genes in potato tubers, by inserting the bacterial genes in the potato plastid genome. The expression of the bacterial genes in the plastid genome will be limited to tuber tissue by regulating their expression via the cognate T7 bacteriophage promoter. The T7 RNA polymerase will be inserted in the potato nucleus under control of a tuber-specific promoter. The RNA polymerase will be fused at its N-terminus with the transit peptide of the Rubisco small subunit, which will target the T7 polymerase to plastids, including the amyloplasts in the potato tubers. Expression of the engineered T7 RNA polymerase will lead to expression of the bacterial genes in plastids under the cognate promoter. This will in turn lead to accumulation of PHB at high levels in the tubers in a form which is suitable for storage. Since inserted at a transcriptionally isolated location, the bacterial genes will not be transcribed in the potato leaves or in other plant parts, thereby not affecting adversely plant growth and productivity.

While certain preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An expression cassette suitable for use in higher plants for producing a chimeric gene for expression in stably transformed plastids having genomes containing said chimeric gene, which comprises:
    a) a 5' regulatory segment for controlling expression of a coding segment in plastids;
    b) a 3' regulatory segment for promoting stability of mRNA produced during said 5' regulatory segment-controlled expression of said coding segment in said plastids; and
    c) a cloning segment operably linked to said 5' regulatory segment and said 3' regulatory segment, said cloning segment being adapted for insertion of a coding segment, such that said expression of said inserted coding segment is controlled by said 5' regulatory segment and said mRNA produced during said expression is stabilized by said 3' regulatory segment, wherein said 5' regulatory segment comprises a nucleotide sequence selected from the group consisting of SEQ ID NO: 5, SEQ ID NO: 12, SEQ ID NO: 13, SEQ ID NO: 14, SEQ ID NO: 15, and SEQ ID NO: 17.

2. An expression cassette suitable for use in higher plants for producing a chimeric gene for expression in stably transformed plastids having genomes containing said chimeric gene, which comprises:
    a) a 5' regulatory segment for controlling expression of a coding segment in plastids;
    b) a 3' regulatory segment for promoting stability of mRNA produced during said 5' regulatory segment-controlled expression of said coding segment in said plastids; and
    c) a cloning segment operably linked to said 5' regulatory segment and said 3' regulatory segment, said cloning segment being adapted for insertion of a coding segment, such that said expression of said inserted coding segment is controlled by said 5' regulatory segment and said mRNA produced during said expression is stabilized by said 3' regulatory segment, wherein said 5' regulatory segment includes a rrn promoter and comprises a nucleotide sequence selected from the group consisting of Sequence I.D. No. 1, Sequence I.D. No. 2, Sequence I.D. No. 4, Sequence I.D. No. 18, Sequence I.D. No. 19, Sequence I.D. No. 24, Sequence I.D. No. 25 and Sequence I.D. No. 26.

3. An expression cassette suitable for use in higher plants for producing a chimeric gene for expression in stably transformed plastids having genomes containing said chimeric gene, which comprises:
   a) a 5' regulatory segment for controlling expression of a coding segment in plastids;
   b) a 3' regulatory segment for promoting stability of mRNA produced during said 5' regulatory segment-controlled expression of said coding segment in said plastids; and
   c) a cloning segment operably linked to said 5' regulatory segment and said 3' regulatory segment, said cloning segment being adapted for insertion of a coding segment, such that said expression of said inserted coding segment is controlled by said 5' regulatory segment and said mRNA produced during said expression is stabilized by said 3' regulatory segment, wherein said 3' regulatory segment comprises a nucleotide sequence selected from the group consisting of SEQ ID NO: 20, SEQ ID NO: 21, SEQ ID NO: 22, SEQ ID NO: 23 and SEQ ID NO: 29.

4. A chimeric gene comprising the expression cassette of claim 2, having said at least one coding segment inserted into said cloning segment.

5. A chimeric gene as claimed in claim 4, wherein said at least one coding segment is a reporter coding segment encoding a detectable gene product.

6. A chimeric gene as claimed in claim 5, wherein said reporter coding segment comprises a coding region of a uidA gene.

7. An expression cassette as claimed in claim 1, wherein said 5' regulatory segment comprises a nucleotide sequence selected from the group consisting of SEQ ID NO: 13 and SEQ ID NO: 14.

8. An isolated 5' regulatory segment for constitutive expression of a coding segment, wherein said 5' regulatory segment includes an rrn promoter and comprises a nucleotide sequence selected from the group consisting of SEQ ID NO: 1, SEQ ID NO: 2, SEQ ID NO: 4, SEQ ID NO: 18, SEQ ID NO: 19, SEQ ID NO: 24, SEQ ID NO: 25 and SEQ ID NO: 26.

9. An expression cassette for producing a chimeric gene for expression in stably transformed plastids having genomes containing said chimeric gene, which comprises:
   a) a 5' regulatory segment for controlling expression of a coding segment in plastids, said segment comprising a plastid gene promoter and a translational control region, wherein said translational control region is selected from the group consisting of an omega sequence from tobacco mosaic virus coat protein, and untranslated leader sequences from alfalfa mosaic virus RNA4 or brome mosaic virus RNA3;
   b) a 3' regulatory segment; and
   c) a cloning segment operably linked to said 5' regulatory segment and said 3' regulatory segment, said cloning segment being adapted for insertion of a coding segment, such that said expression of said inserted coding segment is controlled by said 5' regulatory segment and said mRNA produced during said expression is stabilized by said 3' regulatory segment.

10. An expression cassette as claimed in claim 2, wherein said coding segment encodes an oxygen scavenging enzyme selected from the group consisting of peroxidase and superoxide dismutase.

11. A chimeric gene comprising the expression cassette of claim 1, having said at least one coding segment inserted into said cloning segment.

12. A chimeric gene as claimed in claim 11, wherein said at least one coding segment is a reporter coding segment encoding a detectable gene product.

13. A chimeric gene as claimed in claim 12, wherein said reporter coding segment comprises a coding region of a uidA gene.

14. A chimeric gene comprising the expression cassette of claim 3, having said at least one coding segment inserted into said cloning segment.

15. A chimeric gene as claimed in claim 14, wherein said at least one coding segment is a reporter coding segment encoding a detectable gene product.

16. A chimeric gene as claimed in claim 15, wherein said reporter coding segment comprises a coding region of a uidA gene.

17. A chimeric gene comprising the expression cassette of claim 7, having said at least one coding segment inserted into said cloning segment.

18. A chimeric gene as claimed in claim 17, wherein said at least one coding segment is a reporter coding segment encoding a detectable gene product.

19. A chimeric gene as claimed in claim 18, wherein said reporter coding segment comprises a coding region of a uidA gene.

* * * * *

```
                          SEQUENCE LISTING (1) GENERAL INFORMATION:

(iii) NUMBER OF SEQUENCES: 47

(2) INFORMATION FOR SEQ ID NO:1:

(i) SEQUENCE CHARACTERISTICS:
         (A) LENGTH: 150 base pairs
         (B) TYPE: nucleic acid
         (C) STRANDEDNESS: single
         (D) TOPOLOGY: Not Relevant (ii) MOLECULE TYPE: DNA (genomic)

(iii) HYPOTHETICAL: NO (iv) ANTI-SENSE: NO (xi) SEQUENCE DESCRIPTION: SEQ ID NO:1:

GCTCCCCCGC GCTCGTTCAA TGAGAATGGA TAAGAGGCTC GTGGGATTGA CGTGAGGGGG         60

CAGGGATGGC TATATTTCTG GGAGCGAACT CCGGGCGAAT ACGAAGCGCT TGGATACAGT        120

TGTAGGGAGG GATTTATGGC AGAAGCGGTG                                         150

(2) INFORMATION FOR SEQ ID NO:2:

(i) SEQUENCE CHARACTERISTICS:
         (A) LENGTH: 168 base pairs
         (B) TYPE: nucleic acid
         (C) STRANDEDNESS: single
         (D) TOPOLOGY: Not Relevant (ii) MOLECULE TYPE: DNA (genomic)

(iii) HYPOTHETICAL: NO (iv) ANTI-SENSE: NO (xi) SEQUENCE DESCRIPTION: SEQ ID NO:2:

GCTCCCCCGC CGTCGTTCAA TGAGAATGGA TAAGAGGCTC GTGGGATTGA CGTGAGGGGG         60

CAGGGATGGC TATATTTCTG GGAGCGAACT CCGGGCGAAT ACGAAGCGCT TGGATACAGT        120

TGTAGGGAGG GATTTATCTC ACCACAAACA GAGGGGATTG AACAAGAT                     168
```

(2) INFORMATION FOR SEQ ID NO:3:

(i) SEQUENCE CHARACTERISTICS:
        (A) LENGTH: 2962 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

```
AATTCACCGC CGTATGGCTG ACCGGCGATT ACTAGCGATT CCGGCTTCAT GCAGGCGAGT      60

TGCAGCCTGC AATCCGAACT GAGGACGGGT TTTTGGGGTT AGCTCACCTC GCGGGATCGC     120

GACCCTTTGT CCCGGCCATT GTAGCACGTG TGTCGCCCAG GGCATAAGGG GCATGATGAC     180

TTGACGTCAT CCTCACCTTC CTCCGGCTTA TCACCGGCAG TCTGTTCAGG GTTCCAAACT     240

CAACGATGGC AACTAAACAC GAGGGTTGCG CTCGTTGCGG GACTTAACCC AACACCTTAC     300

GGCACGAGCT GACGACAGCC ATGCACCACC TGTGTCCGCG TTCCCGAAGG CACCCCTCTC     360

TTTCAAGAGG ATTCGCGGCA TGTCAAGCCC TGGTAAGGTT CTTCGCTTTG CATCGAATTA     420

AACCACATGC TCCACCGCTT GTGCGGGCCC CCGTCAATTC CTTTGAGTTT CATTCTTGCG     480

AACGTACTCC CCAGGCGGGA TACTTAACGC GTTAGCTACA GCACTGCACG GGTCGATACG     540

CACAGCGCCT AGTATCCATC GTTTACGGCT AGGACTACTG GGGTATCTAA TCCCATTCGC     600

TCCCCTAGCT TTCGTCTCTC AGTGTCAGTC TCGGCCCAGC AGAGTGCTTT CGCCGTTGGT     660

GTTCTTTCCG ATCTCTACGC ATTTCACCGC TCCACCGGAA ATTCCCTCTG CCCCTACCGT     720

ACTCCAGCTT GGTAGTTTCC ACCGCTGTC CAGGGTTGAG CCCTGGGATT TGACGGCGGA      780

CTTAAAAAGC CACCTACAGA CGCTTTACGC CCAATCATTC CGGATAACGC TTGCATCCTC     840

TGTATTACCG CGGCTGCTGG CACAGAGTTA GCCGATGCTT ATTCCCCAGA TACCGTCATT     900

GCTTCTTCTC CGGGAAAAGA AGTTCACGAC CCGTGGGCCT CTACCTCCA CGCGGCATTG      960

CTCCGTCAGC TTTCGCCCAT TGCGGAAAAT TCCCCACTGC TGCCTCCCGT AGGAGTCTGG    1020

GCCGTGTCTC AGTCCCAGTG TGGCTGATCA TCCTCTCGGA CCAGCTACTG ATCATCGCCT    1080

TGGTAAGCTA TTGCCTCACC AACTAGCTAA TCAGACGCGA GCCCCTCCTC GGGCGGATTC    1140

CTCCTTTTGC TCCTCAGCCT ACGGGGTATT AGCAGCCGTT TCCAGCTGTT GTTCCCCTCC    1200

CAAGGGCAGG TTCTTACGCG TTACTCACCC GTCCGCCACT GGAAACACCA CTTCCCGTCC    1260

GACTTGCATG TGTTAAGCAT GCCGCCAGCG TTCATCCTGA GCCAGGATCG AACTCTCCAT    1320

GAGATTCATA GTTGCATTAC TTATAGCTTC CTTGTTCGTA GACAAAGCGG ATTCGGAATT    1380

GTCTTTCATT CCAAGGCATA ACTTGTATCC ATGCGCTTCA TATTCGCCCG GAGTTCGCTC    1440

CCAGAAATAT AGCCATCCCT GCCCCCTCAC GTCAATCCCA CGAGCCTCTT ATCCATTCTC    1500

ATTGAACGAC GGCGGGGAG CTTTCGAGGC CTCGAAATCC AACTAGAAAA ACTCACATTG     1560

GGCTTAGGGA TAATCAGGCT CGAACTGATG ACTTCCACCA CGTCAAGGTG ACACTCTACC    1620

GCTGAGTTAT ATCCCTTCCC CGCCCCATCG AGAAATAGAA CTGACTAATC CTAAGTCAAA    1680

GGGTCGAGAA ACTCAACGCC ACTATTCTTG AACAACTTGG AGCCGGGCCT TCTTTTCGCA    1740

CTATTACGGA TATGAAAATA ATGGTCAAAA TCGGATTCAA TTGTCAAAGT ACTTTAACTG    1800

CCCCTATCGG AAATAGGATT GACTACCGAT TCCGAAGGAA CTGGAGTTAC ATCTCTTTTC    1860

CATTCAAGAG TTCTTATGCG TTTCCACGCC CCTTTGAGAC CCCGAAAAAT GGACAAATTC    1920
```

```
CTTTTCTTAG GAACACATAC AAGATTCGTC ACTACAAAAA GGATAATGGT AACCCTACCA    1980

TTAACTACTT CATTTATGAA TTTCATAGTA ATAGAAATAC ATGTCCTACC GAGACAGAAT    2040

TTGGAACTTG CTATCCTCTT GCCTAGCAGG CAAAGATTTA CCTCCGTGGA AAGGATGATT    2100

CATTCGGATC GACATGAGAG TCCAACTACA TTGCCAGAAT CCATGTTGTA TATTTGAAAG    2160

AGGTTGACCT CCTTGCTTCT CTCATGGTAC ACTCCTCTTC CCGCCGAGCC CCTTTTCTCC    2220

TCGGTCCACA GAGACAAAAT GTAGGACTGG TGCCAACAAT TCATCAGACT CACTAAGTCG    2280

GGATCACTAA CTAATACTAA TCTAATATAA TAGTCTAATA TATCTAATAT AATAGAAAAT    2340

ACTAATATAA TAGAAAAGAA CTGTCTTTTC TGTATACTTT CCCCGGTTCC GTTGCTACCG    2400

CGGGCTTTAC GCAATCGATC GGATTAGATA GATATCCCTT CAACATAGGT CATCGAAAGG    2460

ATCTCGGAGA CCCACCAAAG TACGAAAGCC AGGATCTTTC AGAAACGGA TTCCTATTCA     2520

AAGAGTGCAT AACCGCATGG ATAAGCTCAC ACTAACCCGT CAATTTGGGA TCCAAATTCG    2580

AGATTTTCCT TGGGAGGTAT CGGGAAGGAT TTGGAATGGA ATAATATCGA TTCATACAGA    2640

AGAAAAGGTT CTCTATTGAT TCAAACACTG TACCTAACCT ATGGGATAGG GATCGAGGAA    2700

GGGGAAAAAC CGAAGATTTC ACATGGTACT TTTATCAATC TGATTTATTT CGTACCTTTC    2760

GTTCAATGAG AAAATGGGTC AAATTCTACA GGATCAAACC TATGGGACTT AAGGAATGAT    2820

ATAAAAAAAA GAGAGGGAAA ATATTCATAT TAAATAAATA TGAAGTAGAA GAACCCAGAT    2880

TCCAAATGAA CAAATTCAAA CTTGAAAAGG ATCTTCCTTA TTCTTGAAGA ATGAGGGCA    2940

AAGGGATTGA TCAAGAAAGA TC                                           2962

(2) INFORMATION FOR SEQ ID NO:4:

(i) SEQUENCE CHARACTERISTICS:
        (A) LENGTH: 165 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

GCTCCCCCGC CGTCGTTCAA TGAGAATGGA TAAGAGGCTC GTGGGATTGA CGTGAGGGGG     60

CAGGGATGGC TATATTTCTG GGAGCGAACT CCGGGCGAAT ACGAAGCGCT TGGATACAGT    120

TGTAGGGAGG GATTTATGTC ACCACAAACA GAGGGGGAAG CGGTG                   165

(2) INFORMATION FOR SEQ ID NO:5:

(i) SEQUENCE CHARACTERISTICS:
        (A) LENGTH: 191 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

GACAATTGAA TCCGATTTTG ACCATTATTT TCATATCCGT AATAGTGCGA AAAGAAGGCC     60
```

| | |
|---|---|
| CGGCTCCAAG TTGTTCAAGA ATAGTGGCGT TGAGTTTCTC GACCCTTTGA CTTAGGATTA | 120 |
| GTCAGTTCTA TTTCTCGAAT ACAGTTGTAG GGAGGGATTT ATGTCACCAC AAACAGAGGG | 180 |
| GGAAGCGGGT G | 191 |

(2) INFORMATION FOR SEQ ID NO:6:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

| | |
|---|---|
| TTGTCAAAGT GAATTCGAGC TCGGTACCCG GGATCCTCT AGAGTCGACC TGCAGGCATG | 60 |
| CAAGCTTACT TTAACTG | 77 |

(2) INFORMATION FOR SEQ ID NO:7:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

| | |
|---|---|
| TTGTCAAAGT AAGCTTGCAT GCCTGCAGGT CGACTCTAGA GGATCCCCGG GTACCGAGCT | 60 |
| CGAATTCACT TTAACTG | 77 |

(2) INFORMATION FOR SEQ ID NO:8:

(i) SEQUENCE CHARACTERISTICS:
        (A) LENGTH: 1232 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

| | |
|---|---|
| TTGTCAAAGT GATCCCCCAT GAATAAATGC AAGAAAATAA CCTCTCCTTC TTTTTCTATA | 60 |
| ATGTAAACAA AAAAGTCTAT GTAAGTAAAA TACTAGTAAA TAAATAAAAA GAAAAAAAGA | 120 |
| AAGGAGCAAT AGCACCCTCT TGATAGAACA AGAAAATGAT TATTGCTCCT TTCTTTTCAA | 180 |
| AACCTCCTAT AGACTAGGCC AGGATCGCTC TAGCTAGACA TTATTTGCCG ACTACCTTGG | 240 |
| TGATCTCGCC TTTCACGTAG TGGACAAATT CTTCCAACTG ATCTGCGCGC GAGGCCAAGC | 300 |
| GATCTTCTTC TTGTCCAAGA TAAGCCTGTC TAGCTTCAAG TATGACGGGC TGATACTGGG | 360 |
| CCGGCAGGCG CTCCATTGCC CAGTCGGCAG CGACATCCTT CGGCGCGATT TTGCCGGTTA | 420 |

| | |
|---|---|
| CTGCGCTGTA CCAAATGCGG GACAACGTAA GCACTACATT TCGCTCATCG CCAGCCCAGT | 480 |
| CGGGCGGCGA GTTCCATAGC GTTAAGGTTT CATTTAGCGC CTCAAATAGA TCCTGTTCAA | 540 |
| GAACCGGATC AAAGAGTTCC TCCGCCGCTG GACCTACCAA GGCAACGCTA TGTTCTCTTG | 600 |
| CTTTTGTCAG CAAGATAGCC AGATCAATGT CGATCGTGGC TGGCTCGAAG ATACCTGCAA | 660 |
| GAATGTCATT GCGCTGCCAT TCTCCAAATT GCAGTTCGCG CTTAGCTGGA TAACGCCACG | 720 |
| GAATGATGTC GTCGTGCACA ACAATGGTGA CTTCTACAGC GCGGAGAATC TCGCTCTCTC | 780 |
| CAGGGGAAGC CGAAGTTTCC AAAAGGTCGT TGATCAAAGC TCGCCGCGTT GTTTCATCAA | 840 |
| GCCTTACGGT CACCGTAACC AGCAAATCAA TATCACTGTG TGGCTTCAGG CCGCCATCCA | 900 |
| CTGCGGAGCC GTACAAATGT ACGGCCAGCA ACGTCGGTTC GAGATGGCGC TCGATGACGC | 960 |
| CAACTACCTC TGATAGTTGA GTCGATACTT CGGCGATCAC CGCTTCCCTC ATGGTAAAAT | 1020 |
| CTTGGTTTAT TTAATCATCA GGGACTCCCA AGCACACTAG TTTTCTACAA ATCAAAATAG | 1080 |
| AAAATAGAAA ATGGAAGGCT TTTTATTCAA CAGTATAACA TGACTTATAT ACTCGTGTCA | 1140 |
| ACCAAGGTGT ATGTAGATCG GGAATTCGAG CTCGGTACCC GGGGATCCTC TAGAGTCGAC | 1200 |
| CTGCAGGCAT GCAAGCTTCG AGACTTTAAC TG | 1232 |

(2) INFORMATION FOR SEQ ID NO:9:

(i) SEQUENCE CHARACTERISTICS:
        (A) LENGTH: 1232 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

| | |
|---|---|
| TTGTCAAAGT CTCGGAATTC GAGCTCGGTA CCCGGGGATC CTCTAGAGTC GACCTGCAGG | 60 |
| CATGCAAGCT TCCGATCTAC ATACACCTTG GTTGACACGA GTATATAAGT CATGTTATAC | 120 |
| TGTTGAATAA AAAGCCTTCC ATTTTCTATT TTCTATTTTG ATTTGTAGAA AACTAGTGTG | 180 |
| CTTGGGAGTC CCTGATGATT AAATAAACCA AGATTTTACC ATGAGGGAAG CGGTGATCGC | 240 |
| CGAAGTATCG ACTCAACTAT CAGAGGTAGT TGGCGTCATC GAGCGCCATC TCGAACCGAC | 300 |
| GTTGCTGGCC GTACATTTGT ACGGCTCCGC AGTGGATGGC GGCCTGAAGC CACACAGTGA | 360 |
| TATTGATTTG CTGGTTACGG TGACCGTAAG GCTTGATGAA ACAACGCGGC GAGCTTTGAT | 420 |
| CAACGACCTT TTGGAAACTT CGGCTTCCCC TGGAGAGAGC GAGATTCTCC GCGCTGTAGA | 480 |
| AGTCACCATT GTTGTGCACG ACGACATCAT TCCGTGGCGT TATCCAGCTA AGCGCGAACT | 540 |
| GCAATTTGGA GAATGGCAGC GCAATGACAT TCTTGCAGGT ATCTTCGAGC CAGCCACGAT | 600 |
| CGACATTGAT CTGGCTATCT TGCTGACAAA AGCAAGAGAA CATAGCGTTG CCTTGGTAGG | 660 |
| TCCAGCGGCG GAGGAACTCT TTGATCCGGT TCTTGAACAG GATCTATTTG AGGCGCTAAA | 720 |
| TGAAACCTTA ACGCTATGGA ACTCGCCGCC CGACTGGGCT GGCGATGAGC GAAATGTAGT | 780 |
| GCTTACGTTG TCCCGCATTT GGTACAGCGC AGTAACCGGC AAAATCGCGC CGAAGGATGT | 840 |
| CGCTGCCGAC TGGGCAATGG AGCGCCTGCC GGCCCAGTAT CAGCCCGTCA TACTTGAAGC | 900 |
| TAGACAGGCT TATCTTGGAC AAGAAGAAGA TCGCTTGGCC TCGCGCGCAG ATCAGTTGGA | 960 |
| AGAATTTGTC CACTACGTGA AAGGCGAGAT CACCAAGGTA GTCGGCAAAT AATGTCTAGC | 1020 |

```
TAGAGCGATC CTGGCCTAGT CTATAGGAGG TTTTGAAAAG AAAGGAGCAA TAATCATTTT      1080

CTTGTTCTAT CAAGAGGGTG CTATTGCTCC TTTCTTTTTT TCTTTTTATT TATTTACTAG      1140

TATTTTACTT ACATAGACTT TTTTGTTTAC ATTATAGAAA AAGAAGGAGA GGTTATTTTC      1200

TTGCATTTAT TCATGGGGGA TCACTTTAAC TG                                    1232
```

(2) INFORMATION FOR SEQ ID NO:10:

(i) SEQUENCE CHARACTERISTICS:
        (A) LENGTH: 1134 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

```
TTGTCAAAGT AGCTTGAATT AATTCAATGG AAGCAATGAT AAAAAAATAC AAATAGAAAA        60

GGAAAGGGAG GAAATACAAA AAAATAGAAG AGAAAAGTCA TACAAAGTTA TATACAAATG       120

ACTACCCCCC TTTTTGTATT TCCTTAATTT ATTTCCTTAA TTGAATTTCT CTAGCTAGAC       180

ATTATTTGCC GACTACCTTG GTGATCTCGC CTTTCACGTA GTGGACAAAT TCTTCCAACT       240

GATCTGCGCG CGAGGCCAAG CGATCTTCTT CTTGTCCAAG ATAAGCCTGT CTAGCTTCAA       300

GTATGACGGG CTGATACTGG GCCGGCAGGC GCTCCATTGC CCAGTCGGCA GCGACATCCT       360

TCGGCGCGAT TTTGCCGGTT ACTGCGCTGT ACCAAATGCG GGACAACGTA AGCACTACAT       420

TTCGCTCATC GCCAGCCCAG TCGGGCGGCG AGTTCCATAG CGTTAAGGTT TCATTTAGCG       480

CCTCAAATAG ATCCTGTTCA AGAACCGGAT CAAAGAGTTC CTCCGCCGCT GGACCTACCA       540

AGGCAACGCT ATGTTCTCTT GCTTTTGTCA GCAAGATAGC CAGATCAATG TCGATCGTGG       600

CTGGCTCGAA GATACCTGCA AGAATGTCAT TGCGCTGCCA TTCTCCAAAT TGCAGTTCGC       660

GCTTAGCTGG ATAACGCCAC GGAATGATGT CGTCGTGCAC AACAATGGTG ACTTCTACAG       720

CGCGGAGAAT CTCGCTCTCT CCAGGGGAAG CCGAAGTTTC CAAAAGGTCG TTGATCAAAG       780

CTCGCCGCGT TGTTTCATCA AGCCTTACGG TCACCGTAAC CAGCAAATCA ATATCACTGT       840

GTGGCTTCAG GCCGCCATCC ACTGCGGAGC CGTACAAATG TACGGCCAGC AACGTCGGTT       900

CGAGATGGCG CCGCTTCTGC CATAAATCCC TCCCTACAAC TGTATCCAAG CGCTTCGTAT       960

TCGCCCGGAG TTCGCTCCCA GAAATATAGC CATCCCTGCC CCCTCACGTC AATCCCACGA      1020

GCCTCTTATC CATTCTCATT GAACGACGGC GGGGGAGCTT TGGGAATTCG AGCTCGGTAC      1080

CCGGGGATCC TCTAGAGTCG ACCTGCAGGC ATGCAAGCTT CGAGACTTTA ACTG           1134
```

(2) INFORMATION FOR SEQ ID NO:11:

(i) SEQUENCE CHARACTERISTICS:
        (A) LENGTH: 1448 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

```
TTGTCAAAGT AGCTTGAATT AATTCAATGG AAGCAATGAT AAAAAAATAC AAATAGAAAA      60

GGAAAGGGAG GAAATACAAA AAAATAGAAG AGAAAAGTCA TACAAAGTTA TATACAAATG     120

ACTACCCCCC TTTTTGTATT TCCTTAATTT ATTTCCTTAA TTGAATTTCT CTAGCTAGAC     180

ATTATTTGCC GACTACCTTG GTGATCTCGC CTTTCACGTA GTGGACAAAT TCTTCCAACT     240

GATCTGCGCG CGAGGCCAAG CGATCTTCTT CTTGTCCAAG ATAAGCCTGT CTAGCTTCAA     300

GTATGACGGG CTGATACTGG GCCGGCAGGC GCTCCATTGC CCAGTCGGCA GCGACATCCT     360

TCGGCGCGAT TTTGCCGGTT ACTGCGCTGT ACCAAATGCG GGACAACGTA AGCACTACAT     420

TTCGCTCATC GCCAGCCCAG TCGGGCGGCG AGTTCCATAG CGTTAAGGTT TCATTTAGCG     480

CCTCAAATAG ATCCTGTTCA AGAACCGGAT CAAAGAGTTC CTCCGCCGCT GGACCTACCA     540

AGGCAACGCT ATGTTCTCTT GCTTTTGTCA GCAAGATAGC CAGATCAATG TCGATCGTGG     600

CTGGCTCGAA GATACCTGCA AGAATGTCAT TGCGCTGCCA TTCTCCAAAT TGCAGTTCGC     660

GCTTAGCTGG ATAACGCCAC GGAATGATGT CGTCGTGCAC AACAATGGTG ACTTCTACAG     720

CGCGGAGAAT CTCGCTCTCT CCAGGGGAAG CCGAAGTTTC CAAAAGGTCG TTGATCAAAG     780

CTCGCCGCGT TGTTTCATCA AGCCTTACGG TCACCGTAAC CAGCAAATCA ATATCACTGT     840

GTGGCTTCAG GCCGCCATCC ACTGCGGAGC CGTACAAATG TACGGCCAGC AACGTCGGTT     900

CGAGATGGCG CCGCTTCCCC CATGGCATTC CTCTAAGAAC CGGTCTGGAA TTGATTCAAT     960

TATGGAATCA TGAATAGTCA TTGGTTGGGC TGATGTATAA ACACCATAAT CTATACTTTG    1020

TTCTATATCT ATATACTATA GAGATAGGTG GATAAATATT TTTCTTTAGT AAGACCCCAT    1080

CGCTAATATT AATTTATCTA ACATATTAAT TAATATTTAA TATATAAATA TATATAGAAA    1140

TAATAATAAA TAAGAATAAT AATAAATAAG ACGAATAAAT GAGTTCTTTT TGATTCTGCA    1200

TCTTCACGTG ACTCAATAGG AGAGATTGAC CTATTTCAGA CTTCTTCAAA TAGCAAAGAT    1260

TCCGCTTATA AGGAATGATT AAAACTATTT ATATTTCTAA ATTTAGAAAG TTCCCTTTTC    1320

GACATCATTA TTTGAAGAAA ATTTGATAGT TAAAGATCAC TTTTGATCCC GAATTGGGAA    1380

TTCGAGCTCG GTACCCGGGG ATCCTCTAGA GTCGACCTGC AGGCATGCAA GCTTCGAGAC    1440

TTTAACTG                                                             1448

(2) INFORMATION FOR SEQ ID NO:12:

(i) SEQUENCE CHARACTERISTICS:
        (A) LENGTH: 139 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

CGAAAGGTTA GAAATCAACA AAAGAAAAAG TAAGTGGACC TGACCTATTG AATCATGACT      60

ATATCCGCTA TTCTGATATT AAAATTCGAT AGAGATGAAA TTGGAGCTCT AGAATTCAGT     120

TGTAGGGAGG GATCCATGG                                                  139

(2) INFORMATION FOR SEQ ID NO:13:

(i) SEQUENCE CHARACTERISTICS:
        (A) LENGTH: 254 base pairs
```

(B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:13:

GAATTCGAGC TCGGTACCCG GGCAACCCAC TAGCATATCG AAATTCTAAT TTTCTGTAGA      60

GAAGTCCGTA TTTTTCCAAT CAACTTCATT AAAAATTTGA ATAGATCTAC ATACACCTTG     120

GTTGACACGA GTATATAAGT CATGTTATAC TGTTGAATAA AAAGCCTTCC ATTTTCTATT     180

TTCTATTTTG ATTTGTAGAA AACTAGTGTG CTTGGGAGTC CCTGATGATT AAATAAACCA     240

AGATTTTACC ATGG                                                      254

(2) INFORMATION FOR SEQ ID NO:14:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:14:

GAATTCGAGC TCGGTACCCG ATCTACATAC ACCTTGGTTG ACACGAGTAT ATAAGTCATG      60

TTATACTGTT GAATAAAAAG CCTTCCATTT TCTATTTTCT ATTTTGATTT GTAGAAAACT     120

AGTGTGCTTG GGAGTCCCTG ATGATTAAAT AAACCAAGAT TTTACCATGG                170

(2) INFORMATION FOR SEQ ID NO:15:

(i) SEQUENCE CHARACTERISTICS:
        (A) LENGTH: 278 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

GTCGACTAGT CAGGTATTTC CATTTCAAAA AAAAAAAAG TAAAAAAGAA AAATTGGGTT       60

GCGCTATATA TATGAAAGAG TATACAATAA TGATGTATTT GGCAAATCAA ATACCATGGT     120

CTAATAATCA AACATTCTGA TTAGTTGATA ATATTAGTAT TAGTTGGAAA TTTTGTGAAA     180

GATTCCTATG AAAAGTTTCA TTAACACGGA ATTCGTGTCG AGTAGACCTT GTTGTTGTGA     240

GAATTCTTAA TTCATGAGTT GTAGGGAGGG ATCCATGG                             278

(2) INFORMATION FOR SEQ ID NO:16:

(i) SEQUENCE CHARACTERISTICS:
        (A) LENGTH: 457 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:16:

```
GAATTCGGGA TCAAAAGTGA TCTTTAACTA TCAAATTTTC TTCAAATAAT GATGTCGAAA      60
AGGGAACTTT CTAAATTTAG AAATATAAAT AGTTTTAATC ATTCCTTATA AGCGGAATCT     120
TTGCTATTTG AAGAAGTCTG AAATAGGTCA ATCTCTCCTA TTGAGTCACG TGAAGATGCA     180
GAATCAAAAA GAACTCATTT ATTCGTCTTA TTTATTATTA TTCTTATTTA TTATTATTTC     240
TATATATATT TATATATTAA ATATTAATTA ATATGTTAGA TAAATTAATA TTAGCGATGG     300
GGTCTTACTA AAGAAAAATA TTTATCCACC TATCTCTATA GTATATAGAT ATAGAACAAA     360
GTATAGATTA TGGTGTTTAT ACATCAGCCC AACCAATGAC TATTCATGAT TCCATAATTG     420
AATCAATTCC AGACCGGTTC TTAGAGGAAT GCCATGG                              457
```

(2) INFORMATION FOR SEQ ID NO:17:

(i) SEQUENCE CHARACTERISTICS:
        (A) LENGTH: 185 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

```
GAATTCGAGC TCGGTAACTT TGACAATTGA ATCCGATTTT GACCATTATT TTCATATCCG      60
TAATAGTGCG AAAAGAAGGC CCGGCTCCAA GTTGTTCAAG AATAGTGGCG TTGAGTTTCT     120
CGACCCTTTG ACTTAGGATT AGTCAGTTCT ATTTCTCGAA TACAGTTGTA GGGAGGGATC     180
CATGG                                                                 185
```

(2) INFORMATION FOR SEQ ID NO:18:

(i) SEQUENCE CHARACTERISTICS:
        (A) LENGTH: 161 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

```
GAATTCGAGC TCGGTACCCA AAGCTCCCCC GCCGTCGTTC AATGAGAATG GATAAGAGGC      60
TCGTGGGATT GACGTGAGGG GGCAGGGATG GCTATATTTC TGGGAGCGAA CTCCGGGCGA     120
ATACGAAGCG CTTGGATACA GTTGTAGGGA GGGATCCATG G                         161
```

(2) INFORMATION FOR SEQ ID NO:19:

(i) SEQUENCE CHARACTERISTICS:
        (A) LENGTH: 140 base pairs (B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

```
GAGCTCGGTA CCCAAAGCTC CCCCGCCGTC GTTCAATGAG AATGGATAAG AGGCTCGTGG      60
GATTGACGTG AGGGGGCAGG GATGGCTATA TTTCTGGGAG CGAACTCCGG GCGAATTCAG     120
TTGTAGGGAG GGATCCATGG                                                  140
```

(2) INFORMATION FOR SEQ ID NO:20:

(i) SEQUENCE CHARACTERISTICS:
(A) LENGTH: 420 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

```
TCTAGAGCGA TCCTGGCCTA GTCTATAGGA GGTTTTGAAA AGAAAGGAGC AATAATCATT      60
TTCTTGTTCT ATCAAGAGGG TGCTATTGCT CCTTTCTTTT TTTCTTTTTA TTTATTTACT     120
AGTATTTTAC TTACATAGAC TTTTTTGTTT ACATTATAGA AAAGAAGGA GAGGTTATTT     180
TCTTGCATTT ATTCATGATT GAGTATTCTA TTTTGATTTT GTATTTGTTT AAATTGTGAA     240
ATAGAACTTG TTTCTCTTCT TGCTAATGTT ACTATATCTT TTTGATTTTT TTTTTCCAAA     300
AAAAAAATCA AATTTTGACT TCTTCTTATC TCTTATCTTT GAATATCTCT TATCTTTGAA     360
ATAATAATAT CATTGAAATA AGAAAGAAGA GCTATATTCG ACCTGCAGGC ATGCAAGCTT     420
```

(2) INFORMATION FOR SEQ ID NO:21:

(i) SEQUENCE CHARACTERISTICS:
(A) LENGTH: 235 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:21:

```
TCTAGAGCGA TCCTGGCCTA GTCTATAGGA GGTTTTGAAA AGAAAGGAGC AATAATCATT      60
TTCTTGTTCT ATCAAGAGGG TGCTATTGCT CCTTTCTTTT TTTCTTTTTA TTTATTTACT     120
AGTATTTTAC TTACATAGAC TTTTTTGTTT ACATTATAGA AAAGAAGGA GAGGTTATTT     180
TCTTGCATTT ATTCATGGGG GATCCTCTAG AGTCGACCTG CAGGCATGCA AGCTT          235
```

(2) INFORMATION FOR SEQ ID NO:22:

(i) SEQUENCE CHARACTERISTICS:
(A) LENGTH: 226 base pairs (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:22:

```
TCTAGAGTAG ACATTAGCAG ATAAATTAGC AGGAAATAAA GAAGGATAAG GAGAAAGAAC      60

TCAAGTAATT ATCCTTCGTT CTCTTAATTG AATTGCAATT AAACTCGGCC CAATCTTTTA     120

CTAAAAGGAT TGAGCCGAAT ACAACAAAGA TTCTATTGCA TATATTTTGA CTAAGTATAT     180

ACTTACCTAG ATATACAAGA TTTGAAATAC AAAATCTAGC AAGCTT                    226
```

(2) INFORMATION FOR SEQ ID NO:23:

(i) SEQUENCE CHARACTERISTICS:
        (A) LENGTH: 166 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:23:

```
TCTAGAGAAA TTCAATTAAG GAAATAAATT AAGGAAATAC AAAAAGGGGG GTAGTCATTT      60

GTATATAACT TTGTATGACT TTTCTCTTCT ATTTTTTGT ATTTCCTCCC TTTCCTTTTC      120

TATTTGTATT TTTTTATCAT TGCTTCCATT GAATTAATTC AAGCTT                    166
```

(2) INFORMATION FOR SEQ ID NO:24:

(i) SEQUENCE CHARACTERISTICS:
        (A) LENGTH: 258 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:24:

```
GAGCTCGGTA CCCAAAGCTC CCCCGCCGTC GTTCAATGAG AATGGATAAG AGGCTCGTGG      60

GATTGACGTG AGGGGGCAGG GATGGCTATA TTTCTGGGAG CGAACTCCGG GCGAATTATA     120

GAATTTTTAT CTTCGAAACC CATTGCAAAG GGCAGTGCAA GAGAAATCAT ACAAAAATGA     180

TCGAATCTTC GGACGCCCCG AAAAAGATAT GAGGTGCTCG GAAATGGTCG AAGTAGTTGA     240

ATAGGAGGAT CACCATGG                                                   258
```

(2) INFORMATION FOR SEQ ID NO:25:

(i) SEQUENCE CHARACTERISTICS:
        (A) LENGTH: 129 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:25:

CCAAAGCTCC CCCGCCGTCG TTCAATGAGA ATGGATAAGA GGCTCGTGGG ATTGACGTGA      60

GGGGGCAGGG ATGGCTATAT TTCTGGGAGC GAACTCCGGG CGAATTCACT TCTAGGGAGG     120

CATCCATGG                                                            129

(2) INFORMATION FOR SEQ ID NO:26:

(i) SEQUENCE CHARACTERISTICS:
            (A) LENGTH: 164 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:26:

CCAAAGCTCC CCCGCCGTCG TTCAATGAGA ATGGATAAGA GGCTCGTGGG ATTGACGTGA      60

GGGGGCAGGG ATGGCTATAT TTCTGGGAGC GAACTCCGGG CGAATTCAAG ATCTAGTGTG     120

CTTGGGAGTC CCTGATGATT AAATAAACCA AGATTTTACC ATGG                     164

(2) INFORMATION FOR SEQ ID NO:27:

(i) SEQUENCE CHARACTERISTICS:
            (A) LENGTH: 1416 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:27:

GAATTCGAGC TCGGTACCAA AGCTCCCCCG CCGTCGTTCA ATGAGAATGG ATAAGAGGCT      60

CGTGGGATTG ACGTGAGGGG GCAGGGATGG CTATATTTCT GGGAGCGAAC TCCGGGCGAA     120

TACGAAGCGC TTGGATACAG TTGTAGGGAG GGATTTATGT CACCACAAAC AGAGGGGATT     180

GAACAAGATG GATTGCACGC AGGTTCTCCG GCCGCTTGGG TGGAGAGGCT ATTCGGCTAT     240

GACTGGGCAC AACAGACAAT CGGCTGCTCT GATGCCGCCG TGTTCCGGCT GTCAGCGCAG     300

GGGCGCCCGG TTCTTTTTGT CAAGACCGAC CTGTCCGGTG CCCTGAATGA ACTCCAGGAC     360

GAGGCAGCGC GGCTATCGTG GCTGGCCACG ACGGGCGTTC CTTGCGCAGC TGTGCTCGAC     420

GTTGTCACTG AAGCGGGAAG GGACTGGCTG CTATTGGGCG AAGTGCCGGG GCAGGATCTC     480

CTGTCATCTC ACCTTGCTCC TGCCGAGAAA GTATCCATCA TGGCTGATGC AATGCGGCGG     540

CTGCATACGC TTGATCCGGC TACCTGCCCA TTCGACCACC AAGCGAAACA TCGCATCGAG     600

CGAGCACGTA CTCGGATGGA AGCCGGTCTT GTCGATCAGG ATGATCTGGA CGAAGAGCAT     660

CAGGGGCTCG CGCCAGCCGA ACTGTTCGCC AGGCTCAAGG CGCGCATGCC CGACGGCGAG     720

GATCTCGTCG TGACACATGG CGATGCCTGC TTGCCGAATA TCATGGTGGA AAATGGCCGC     780

```
TTTTCTGGAT TCATCGACTG TGGCCGGCTG GGTGTGGCGG ACCGCTATCA GGACATAGCG      840

TTGGCTACCC GTGATATTGC TGAAGAGCTT GGCGGCGAAT GGGCTGACCG CTTCCTCGTG      900

CTTTACGGTA TCGCCGCTCC CGATTCGCAG CGCATCGCCT TCTATCGCCT TCTTGACGAG      960

TTCTTCTGAG CGGGACTCTG GGGTTCGGAT CGATCCTCTA GAGCGATCCT GGCCTAGTCT     1020

ATAGGAGGTT TTGAAAAGAA AGGAGCAATA ATCATTTTCT TGTTCTATCA AGAGGGTGCT     1080

ATTGCTCCTT TCTTTTTTTC TTTTTATTTA TTTACTAGTA TTTTACTTAC ATAGACTTTT     1140

TTGTTTACAT TATAGAAAAA GAAGGAGAGG TTATTTTCTT GCATTTATTC ATGATTGAGT     1200

ATTCTATTTT GATTTTGTAT TTGTTTAAAT TGTGAAATAG AACTTGTTTC TCTTCTTGCT     1260

AATGTTACTA TATCTTTTTG ATTTTTTTTT TCCAAAAAAA AAATCAAATT TTGACTTCTT     1320

CTTATCTCTT ATCTTTGAAT ATCTCTTATC TTTGAAATAA TAATATCATT GAAATAAGAA     1380

AGAAGAGCTA TATTCGACCT GCAGGCATGC AAGCTT                              1416

(2) INFORMATION FOR SEQ ID NO:28:

(i) SEQUENCE CHARACTERISTICS:
         (A) LENGTH: 1208 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:28:

GAATTCGAGC TCGGTACCCA AAGCTCCCCC GCCGTCGTTC AATGAGAATG GATAAGAGGC       60

TCGTGGGATT GACGTGAGGG GGCAGGGATG CTATATTTC TGGGAGCGAA CTCCGGGCGA      120

ATACGAAGCG CTTGGATACA GTTGTAGGGA GGGATCCATG GGGATTGAAC AAGATGGATT      180

GCACGCAGGT TCTCCGGCCG CTTGGGTGGA GAGGCTATTC GGCTATGACT GGGCACAACA      240

GACAATCGGC TGCTCTGATG CCGCCGTGTT CCGGCTGTCA GCGCAGGGGC GCCCGGTTCT      300

TTTTGTCAAG ACCGACCTGT CCGGTGCCCT GAATGAACTC CAGGACGAGG CAGCGCGGCT      360

ATCGTGGCTG GCCACGACGG GCGTTCCTTG CGCAGCTGTG CTCGACGTTG TCACTGAAGC      420

GGGAAGGGAC TGGCTGCTAT TGGGCGAAGT GCCGGGGCAG GATCTCCTGT CATCTCACCT      480

TGCTCCTGCC GAGAAAGTAT CCATCATGGC TGATGCAATG CGGCGGCTGC ATACGCTTGA      540

TCCGGCTACC TGCCCATTCG ACCACCAAGC GAAACATCGC ATCGAGCGAG CACGTACTCG      600

GATGGAAGCC GGTCTTGTCG ATCAGGATGA TCTGGACGAA GAGCATCAGG GGCTCGCGCC      660

AGCCGAACTG TTCGCCAGGC TCAAGGCGCG CATGCCCGAC GGCGAGGATC TCGTCGTGAC      720

ACATGGCGAT GCCTGCTTGC CGAATATCAT GGTGGAAAAT GGCCGCTTTT CTGGATTCAT      780

CGACTGTGGC CGGCTGGGTG TGGCGGACCG CTATCAGGAC ATAGCGTTGG CTACCCGTGA      840

TATTGCTGAA GAGCTTGGCG GCGAATGGGC TGACCGCTTC CTCGTGCTTT ACGGTATCGC      900

CGCTCCCGAT TCGCAGCGCA TCGCCTTCTA TCGCCTTCTT GACGAGTTCT TCTGAGCGGG      960

ACTCTGGGGT TCGGATCGAT CCTCTAGAGT AGACATTAGC AGATAAATTA GCAGGAAATA     1020

AAGAAGGATA AGGAGAAAGA ACTCAAGTAA TTATCCTTCG TTCTCTTAAT TGAATTGCAA     1080

TTAAACTCGG CCCAATCTTT TACTAAAAGG ATTGAGCCGA ATACAACAAA GATTCTATTG     1140

CATATATTTT GACTAAGTAT ATACTTACCT AGATATACAA GATTTGAAAT ACAAAATCTA     1200
```

```
GCAAGCTT                                                             1208
```

(2) INFORMATION FOR SEQ ID NO:29:

(i) SEQUENCE CHARACTERISTICS:
        (A) LENGTH: 293 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:29:

```
TAAAAACAGT AGACATTAGC AGATAAATTA GCAGGAAATA AAGAAGGATA AGGAGAAAGA      60

ACTCAAGTAA TTATCCTTCG TTCTCTTAAT TGAATTGCAA TTAAACTCGG CCCAATCTTT     120

TACTAAAAGG ATTGAGCCGA ATACAACAAA GATTCTATTG CATATATTTT GACTAAGTAT     180

ATACTTACCT AGATATACAA GATTTGAAAT ACAAAATCTA GAAAACTAAA TCAAAATCTA     240

AGACTCAAAT CTTTCTATTG TTGTCTTGGA TCCCGAATTG GGATCCGAAT TCG           293
```

(2) INFORMATION FOR SEQ ID NO:30:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:30:

```
CTTGTATCCA TGCGCTTCGA ATTCGCCCGG AGTTCG                               36
```

(2) INFORMATION FOR SEQ ID NO:31:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:31:

```
AATTCGAAGC GCTTGGATAC AGTTGTAGGG AGGGATC                              37
```

(2) INFORMATION FOR SEQ ID NO:32:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:32:

CATGGATCCC TCCCTACAAC TGTATCCAAG CGCTTCG        37

(2) INFORMATION FOR SEQ ID NO:33:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:33:

GTATCCAAGC GCTTCGTATT CGCCCGGAG        29

(2) INFORMATION FOR SEQ ID NO:34:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:34:

GGCGATCACC GCTTCTGCCA TAAATCCCTC CCTAC        35

(2) INFORMATION FOR SEQ ID NO:35:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:35:

CCATCTTGTT CAATCCCCTC TGTTTGTGGT GACATAAATC CCTCCCTACA AC        52

(2) INFORMATION FOR SEQ ID NO:36:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:36:

GCAGGCATCG CCATGTGTCA CGACGAGATC CTC                                33

(2) INFORMATION FOR SEQ ID NO:37:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:37:

GCAATCCATC TTGTTCAATC CCCATGGTCA TGGGCCGGAT CTG                     43

(2) INFORMATION FOR SEQ ID NO:38:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:38:

GCCTCGTCCT GGAGTTCATT CAGGGC                                        26

(2) INFORMATION FOR SEQ ID NO:39:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:39:

GCTCTAGAGC                                                          10

(2) INFORMATION FOR SEQ ID NO:40:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:40:

CGAGGCCTCG                                                              10

(2) INFORMATION FOR SEQ ID NO:41:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:41:

AAGCTTGCAT GCCTGCAGGT CGACGCTAGA GGATCCCCGG GTACCGAGCT CGAATTC        57

(2) INFORMATION FOR SEQ ID NO:42:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:42:

CCAAGAGCTC CGAAAGGTTA GAAATCAAC                                         29

(2) INFORMATION FOR SEQ ID NO:43:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:43:

CGATAGAGAT GAAATTGGAG CTCTAGACGG                                        30

(2) INFORMATION FOR SEQ ID NO:44:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:44:

GAGCTCTAGA ATTCAGTTGT AGGGAGGGAT CCATGG                                 36

-continued (2) INFORMATION FOR SEQ ID NO:45:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:45:

CCCTCTAGAA TTTTTATCTT CGAAACCC                        28

(2) INFORMATION FOR SEQ ID NO:46:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:46:

CCCCAACGTT CCATGGTGAT CCTCCTATTC AAC                33

(2) INFORMATION FOR SEQ ID NO:47:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:47:

TTTTACCATG GCTGCAAT                                  18